(12) United States Patent
Abdou

(10) Patent No.: US 8,764,806 B2
(45) Date of Patent: Jul. 1, 2014

(54) DEVICES AND METHODS FOR MINIMALLY INVASIVE SPINAL STABILIZATION AND INSTRUMENTATION

(71) Applicant: Samy Abdou, San Diego, CA (US)

(72) Inventor: Samy Abdou, San Diego, CA (US)

(*) Notice: Subject to any disclaimer, the term of this patent is extended or adjusted under 35 U.S.C. 154(b) by 0 days.

(21) Appl. No.: 13/875,228

(22) Filed: May 1, 2013

(65) Prior Publication Data
US 2013/0310942 A1 Nov. 21, 2013

Related U.S. Application Data

(63) Continuation of application No. 12/962,534, filed on Dec. 7, 2010, now abandoned.

(60) Provisional application No. 61/283,745, filed on Dec. 7, 2009.

(51) Int. Cl.
A61B 17/88 (2006.01)
A61F 2/44 (2006.01)

(52) U.S. Cl.
USPC .................................. 606/279; 623/17.16

(58) Field of Classification Search
USPC .................................. 606/279; 623/17.16
See application file for complete search history.

(56) References Cited

U.S. PATENT DOCUMENTS

| 4,254,763 | A | 3/1981 | McCready et al. |
| 5,795,291 | A | 8/1998 | Koros et al. |
| 5,908,382 | A | 6/1999 | Koros |
| 6,248,105 | B1 | 6/2001 | Schlapfer et al. |
| 6,302,843 | B1 | 10/2001 | Lees et al. |
| RE37,665 | E | 4/2002 | Ralph et al. |
| 6,371,957 | B1 | 4/2002 | Amrein et al. |
| 6,565,565 | B1 | 5/2003 | Yuan et al. |
| 6,582,433 | B2 | 6/2003 | Yun |
| 6,641,586 | B2 | 11/2003 | Varieur |
| 6,709,389 | B2 | 3/2004 | Farascioni |
| 7,014,608 | B2 | 3/2006 | Larson et al. |
| 7,048,736 | B2 | 5/2006 | Robinson et al. |
| 7,156,806 | B2 | 1/2007 | Dobrovolny |
| 7,704,271 | B2 | 4/2010 | Abdou |
| 7,738,968 | B2 | 6/2010 | Bleich |
| 7,763,074 | B2 | 7/2010 | Altarac et al. |

(Continued)

OTHER PUBLICATIONS

Denis, F., *The Three Column Spine and Its Significance in the Classification of Acute Thoracolumbar Spinal Injuries*, Spine Nov.-Dec. 1983; 8(8):817-831.

(Continued)

*Primary Examiner* — Ellen C Hammond
(74) *Attorney, Agent, or Firm* — Gazdzinski & Associates, PC

(57) ABSTRACT

Described herein are devices and methods for fusion of adjacent vertebral bones using distractor platforms for exposure and resection of at least a portion of the facet joint, such as in performance of a TLiF procedure. In one embodiment, the distractor platform contains at least a first receptacle and/or extension adapted to couple to the implanted screw/bone marker and the method includes advancing a threaded segment of a bone fastener assembly into the identified first pedicle of the first vertebral bone, the first bone fastener assembly further comprises a second segment adapted to couple with a distraction platform adapted to concurrently attach onto at least one tissue retention blade and adapted to retain the tissue retention blade in the displaced position. Stabilization of a spinal segment is also provided by advancing a substantially concave orthopedic implant through an opening made in at posterior aspect of a disc space.

18 Claims, 63 Drawing Sheets

(56) References Cited

U.S. PATENT DOCUMENTS

| | | |
|---|---|---|
| 7,819,801 B2 | 10/2010 | Miles et al. |
| 7,918,792 B2 | 4/2011 | Drzyzga et al. |
| 8,062,337 B2 | 11/2011 | Bruneau et al. |
| 2005/0021040 A1 | 1/2005 | Bertagnoli |
| 2006/0149278 A1 | 7/2006 | Abdou |
| 2007/0225726 A1 | 9/2007 | Dye et al. |
| 2007/0270840 A1 | 11/2007 | Chin et al. |
| 2008/0065219 A1* | 3/2008 | Dye .......................... 623/17.16 |
| 2008/0183211 A1 | 7/2008 | Lamborne et al. |
| 2009/0171394 A1 | 7/2009 | Abdou |
| 2011/0288594 A1* | 11/2011 | Woolley et al. ............... 606/279 |

OTHER PUBLICATIONS

Holland, NR., *Intraoperative electromyography during thoracolumbar spinal surgery*, Spine Sep. 1998 1:23 (17):1915-1922.

Moskowitz, A., *Transforaminal Lumbar Interbody Fusion*, OrthopClin N Am 33 (2002) 359-366.

Wood, MJ, et al., *Improving accuracy and reducing radiation exposure in minimally invasive lumbar interbody fusion*, J Neurosurg Spine. May 2010: 12(5): 533-539.

* cited by examiner

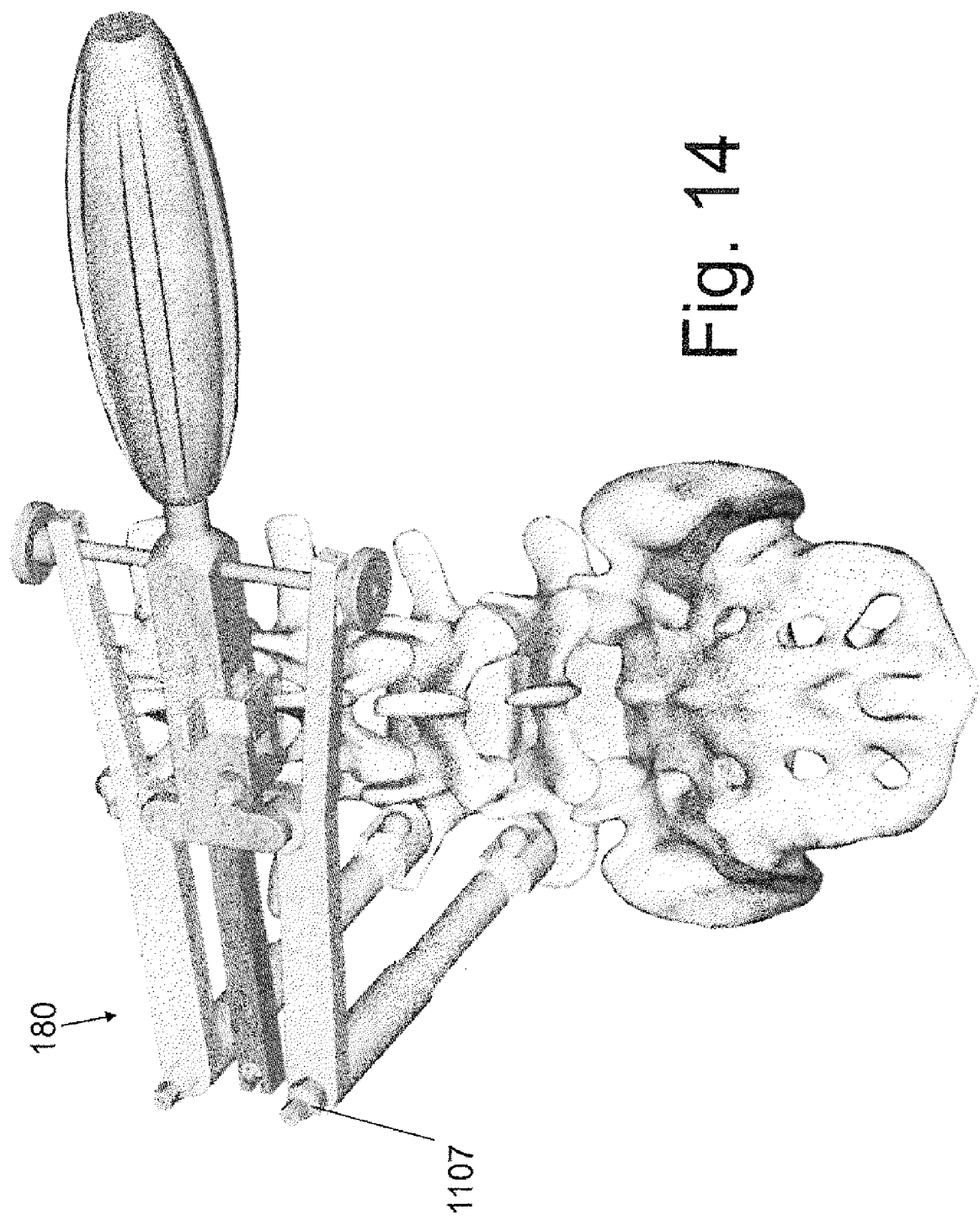

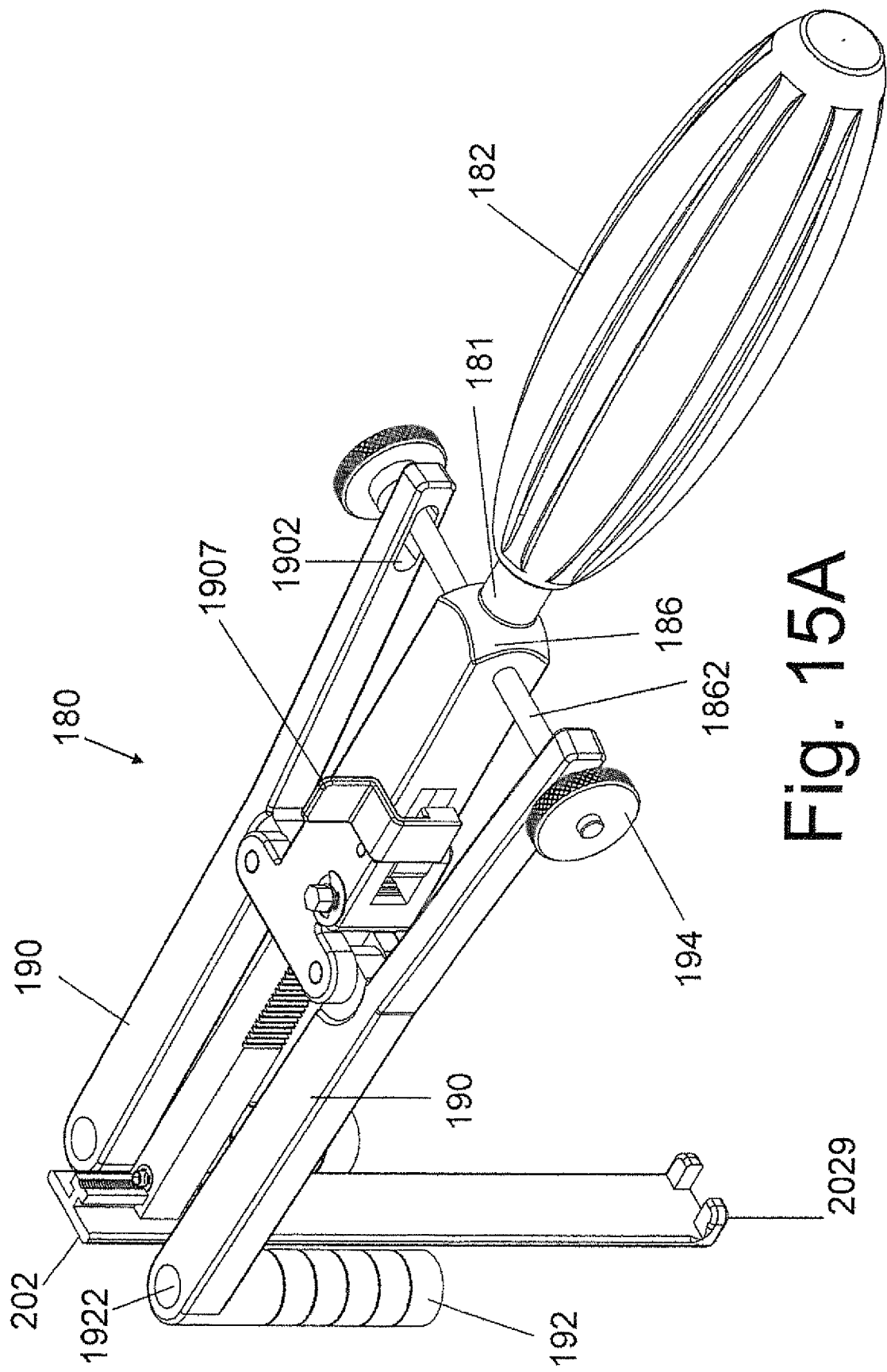

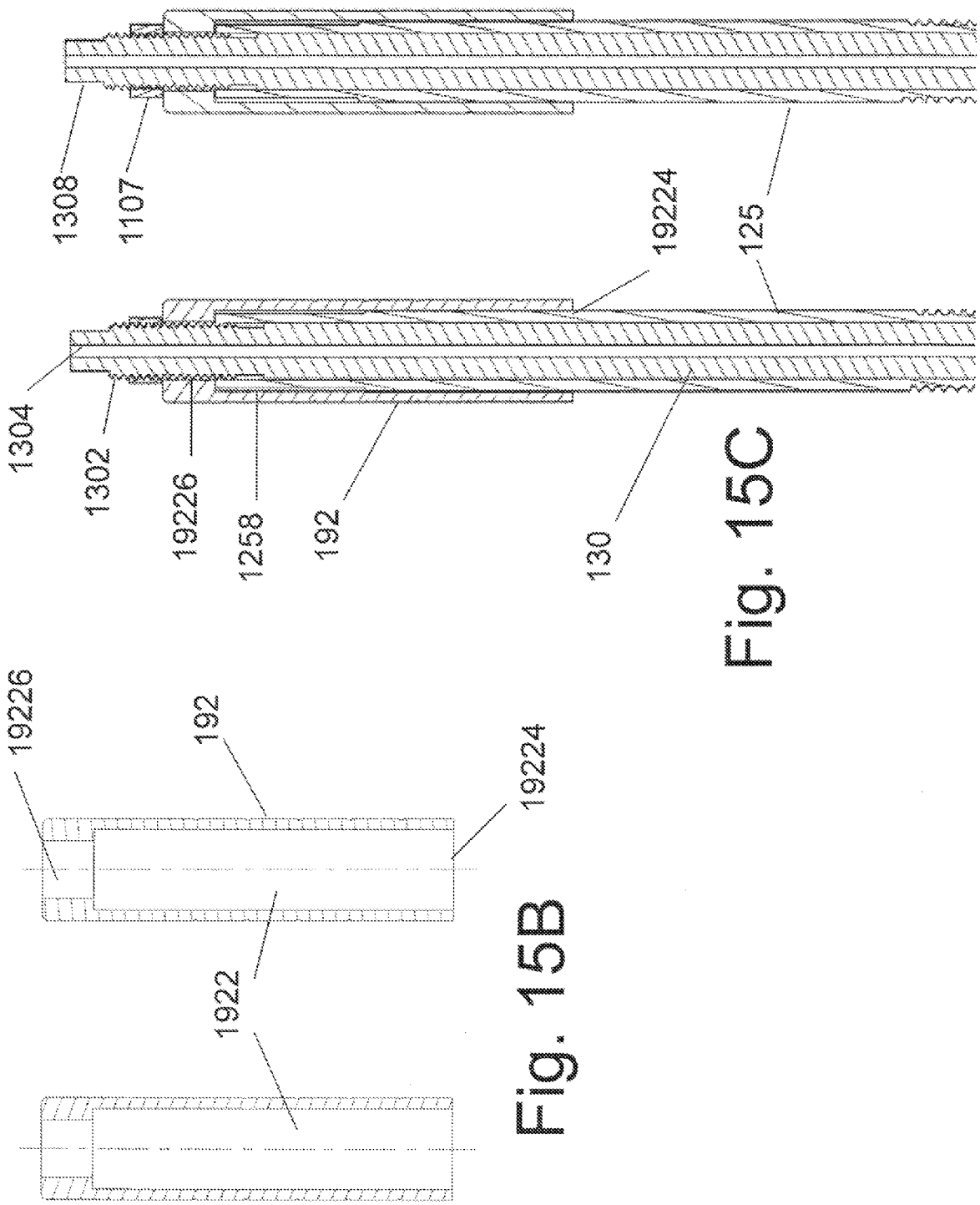

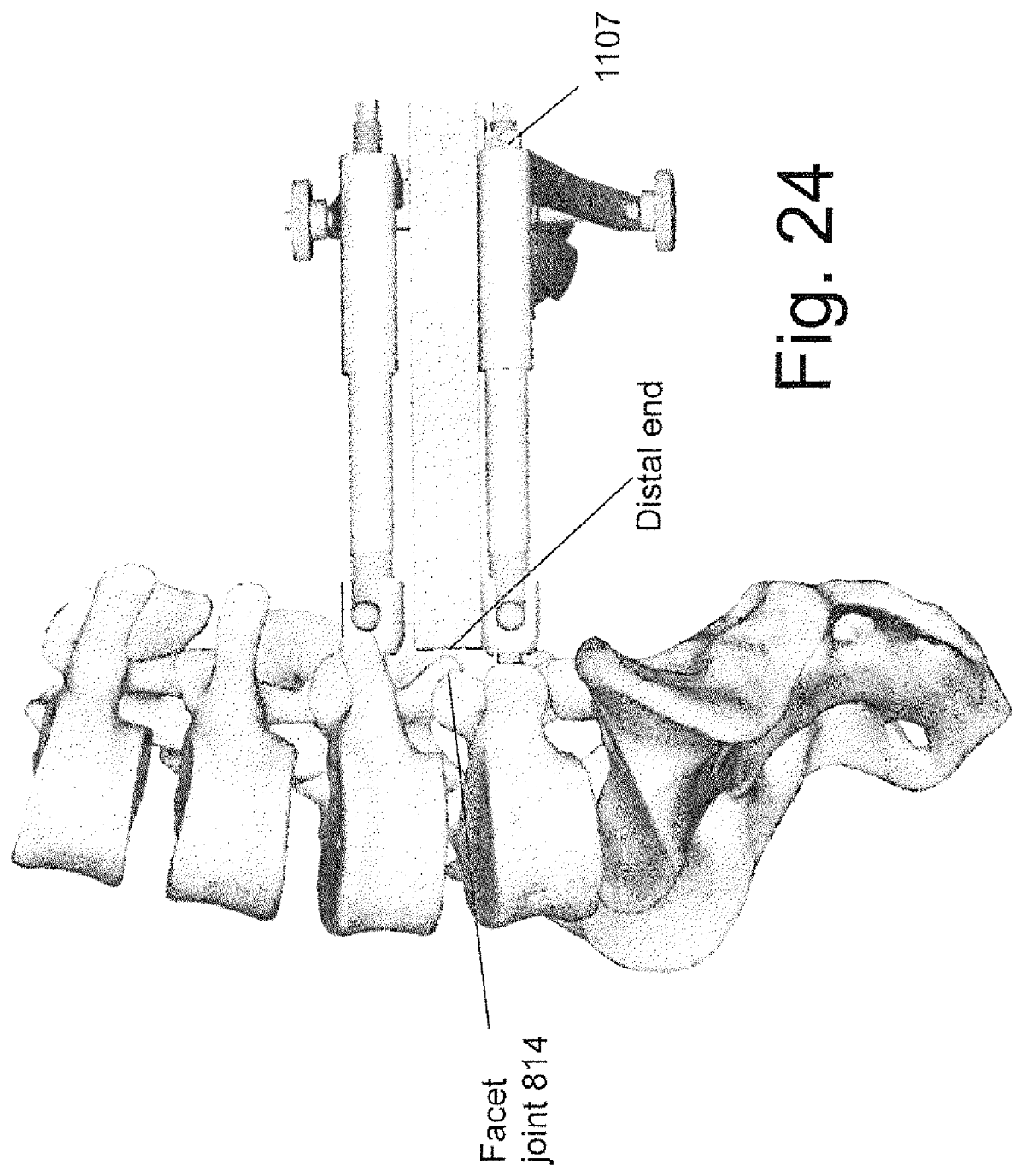

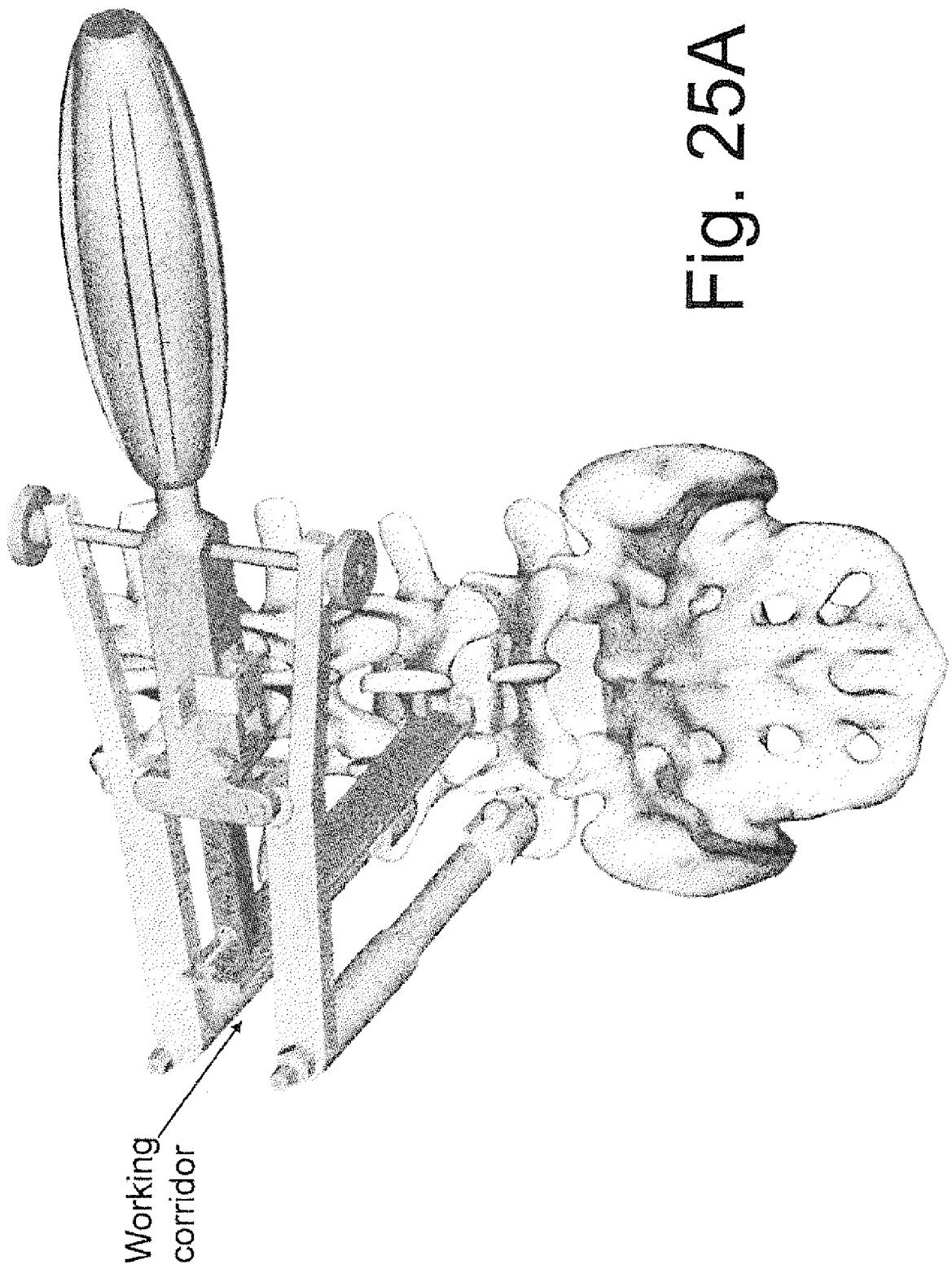

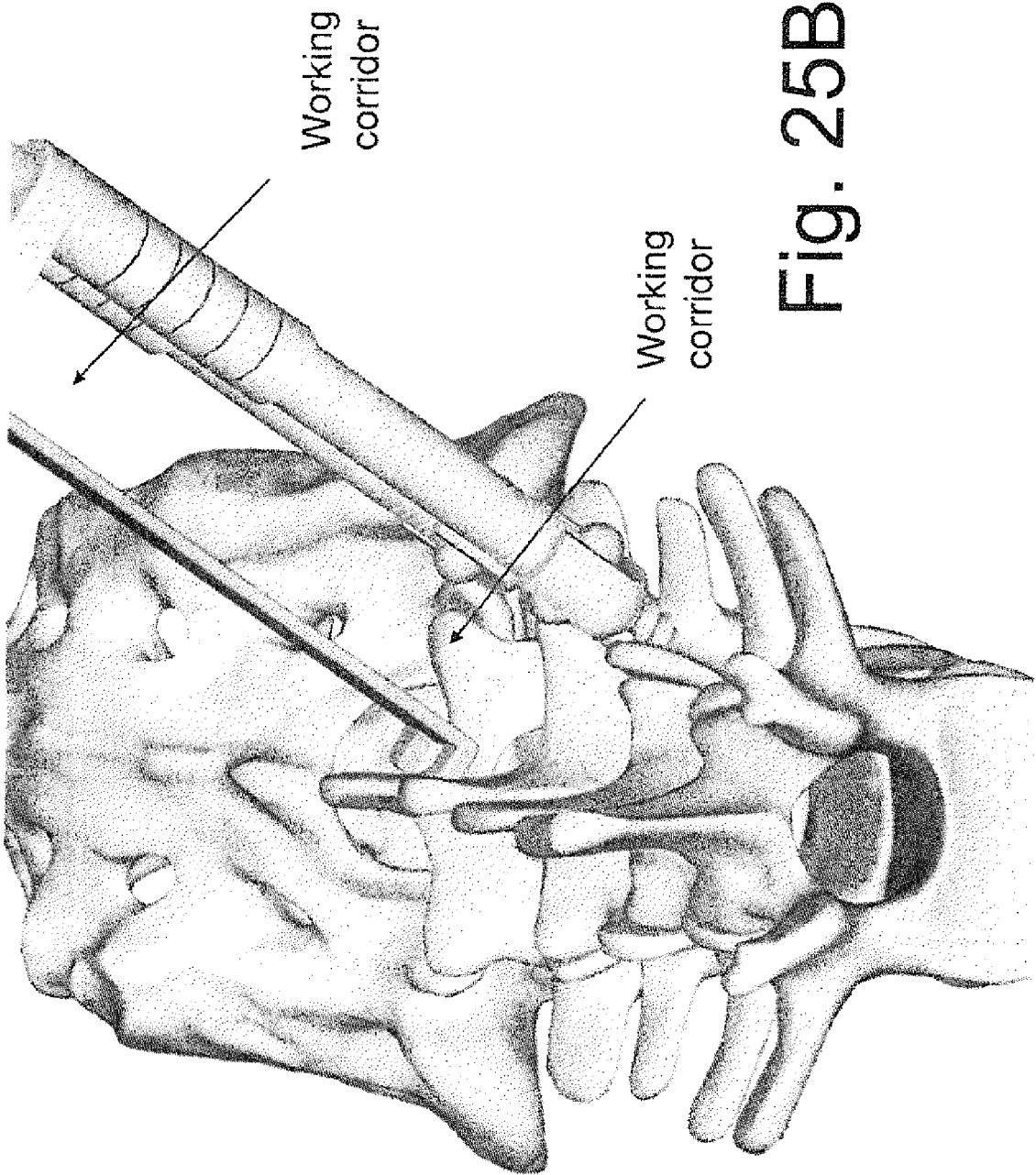

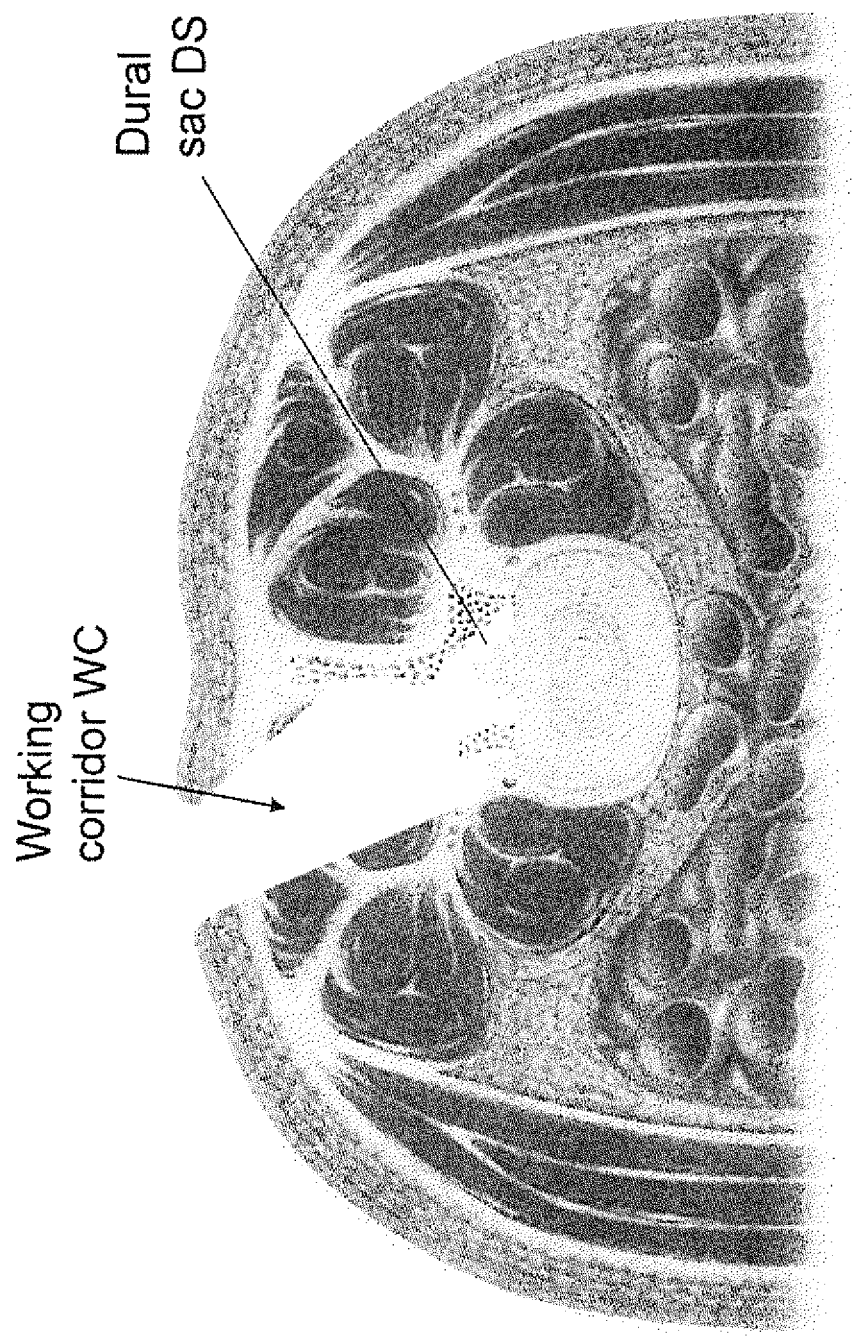

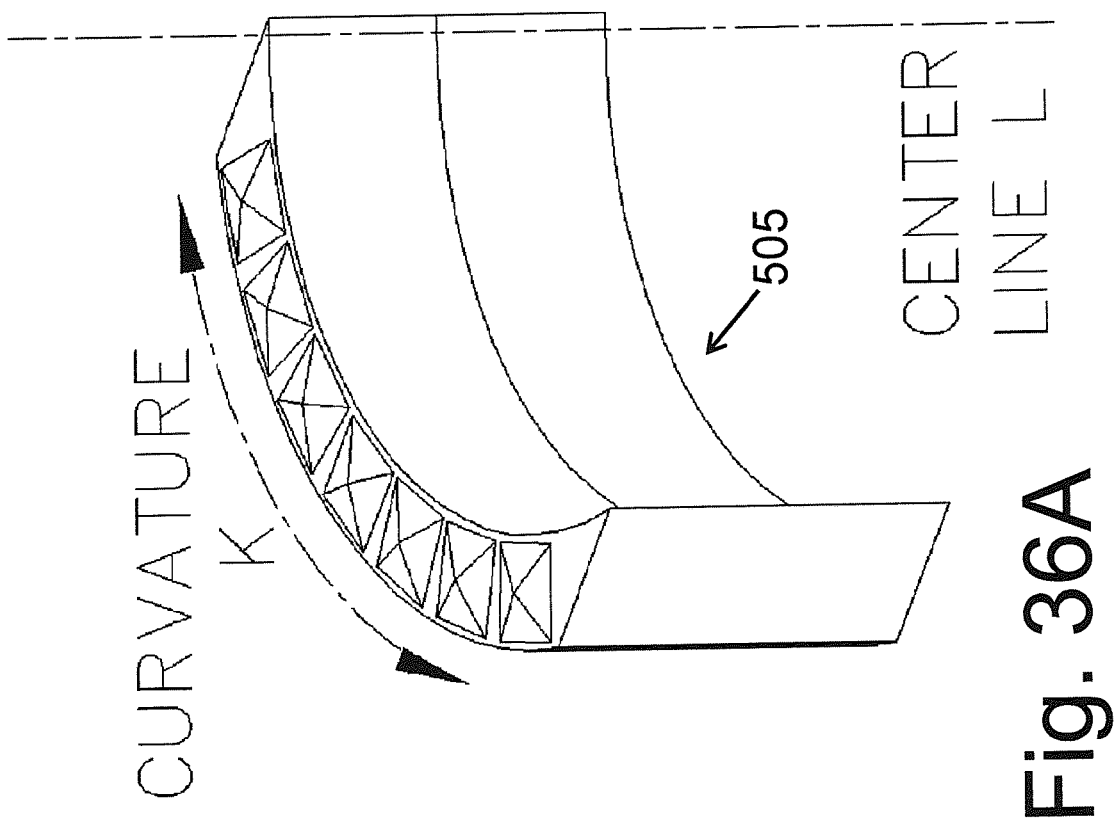
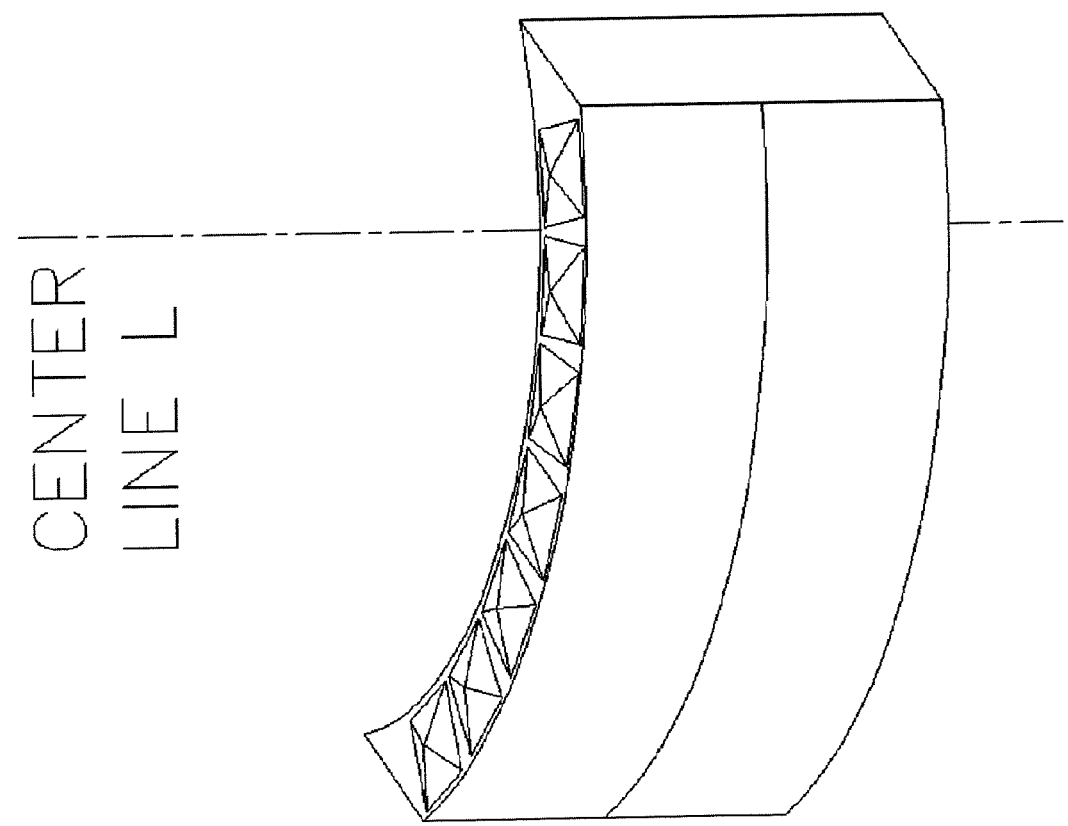
Fig. 36A

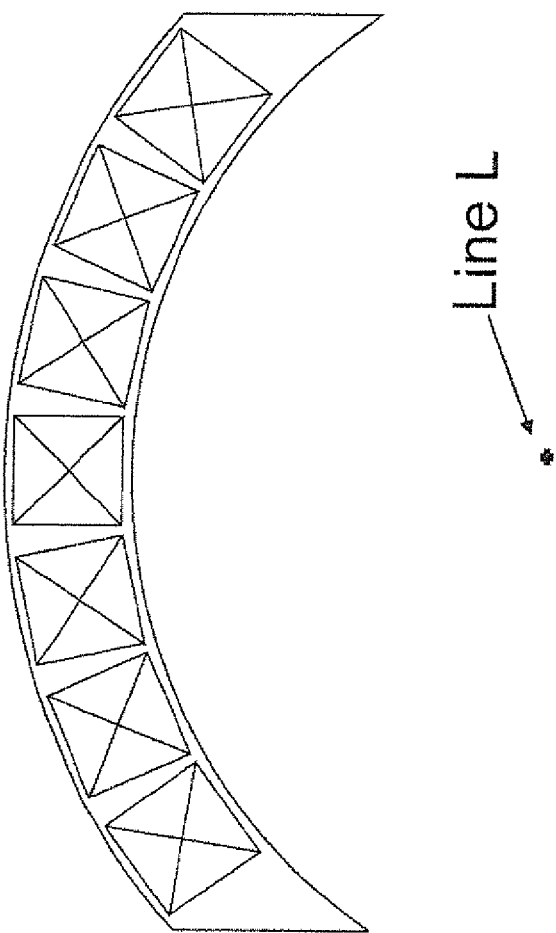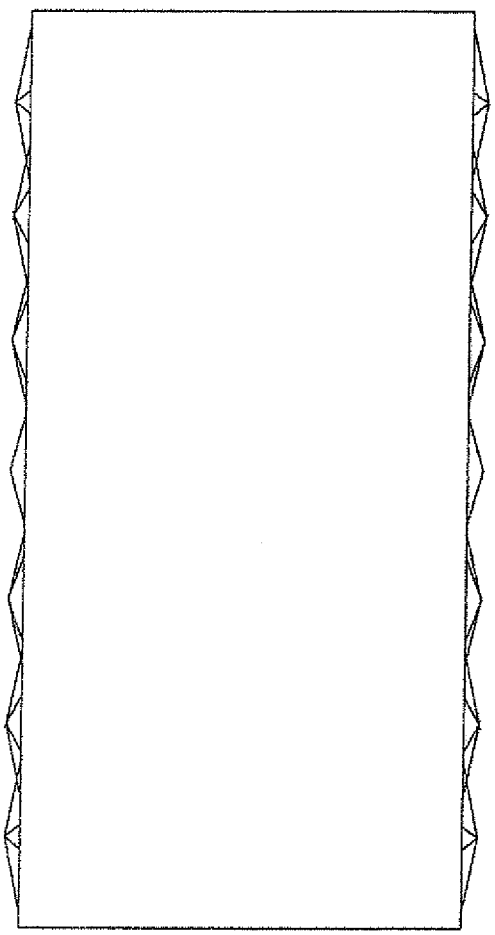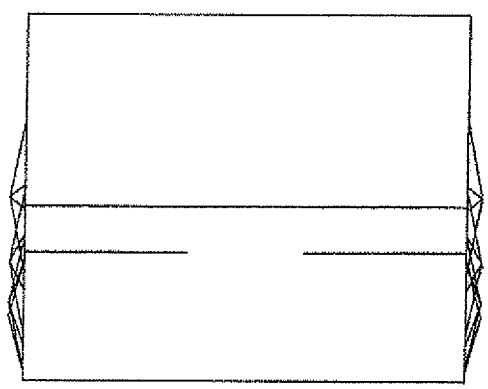
Fig. 36B

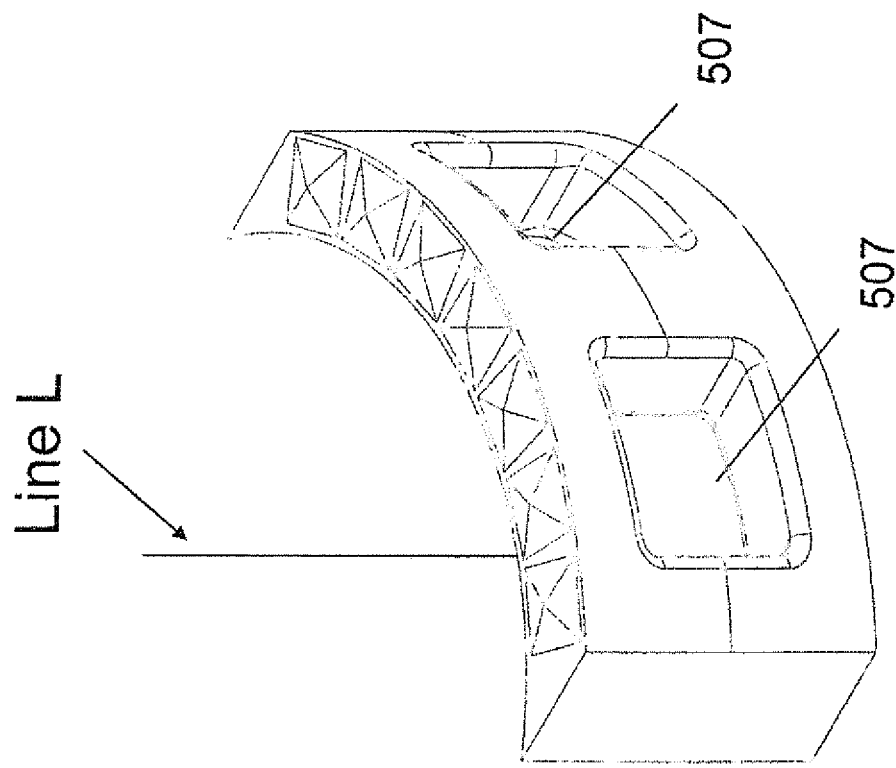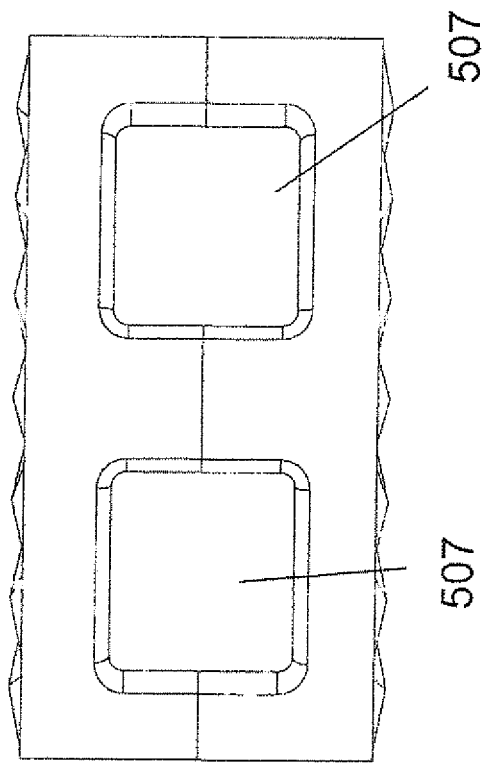
Fig. 37

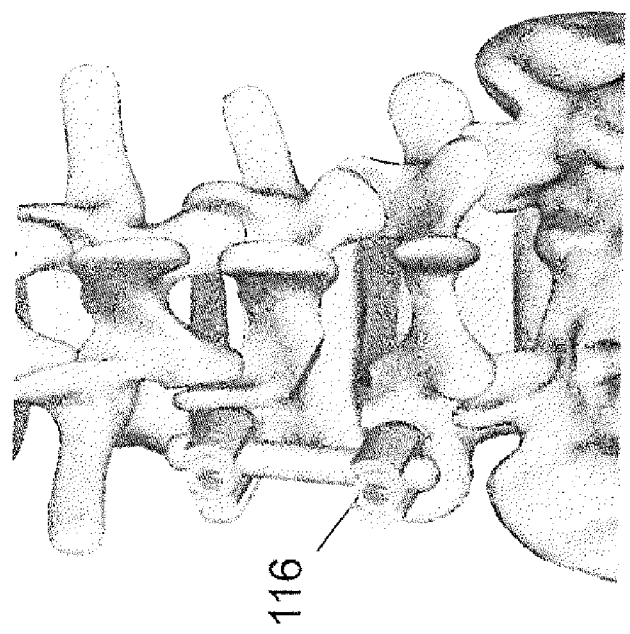
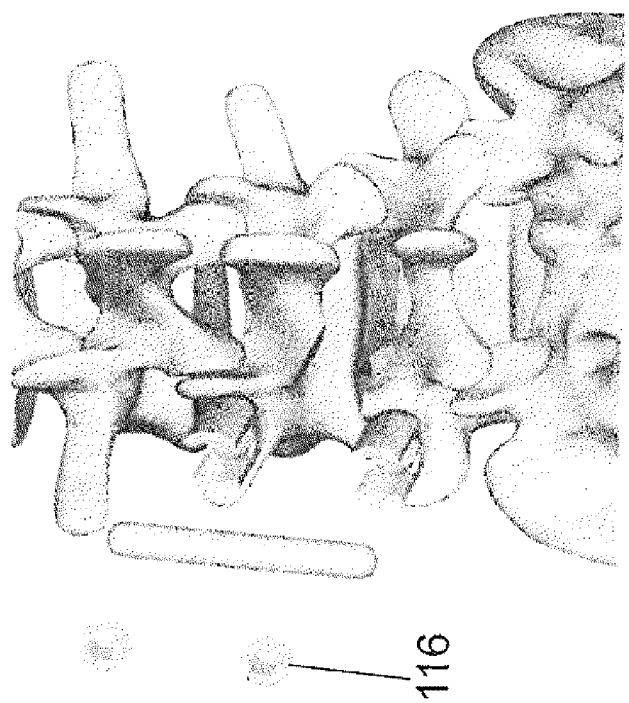

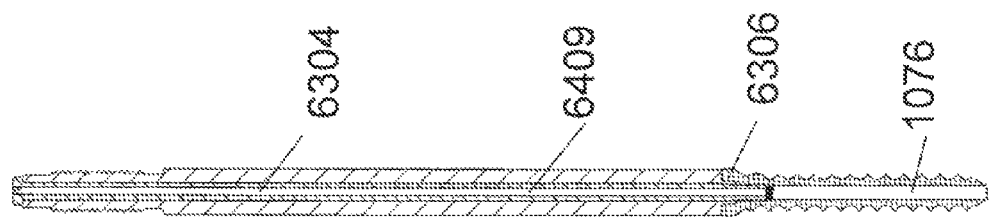
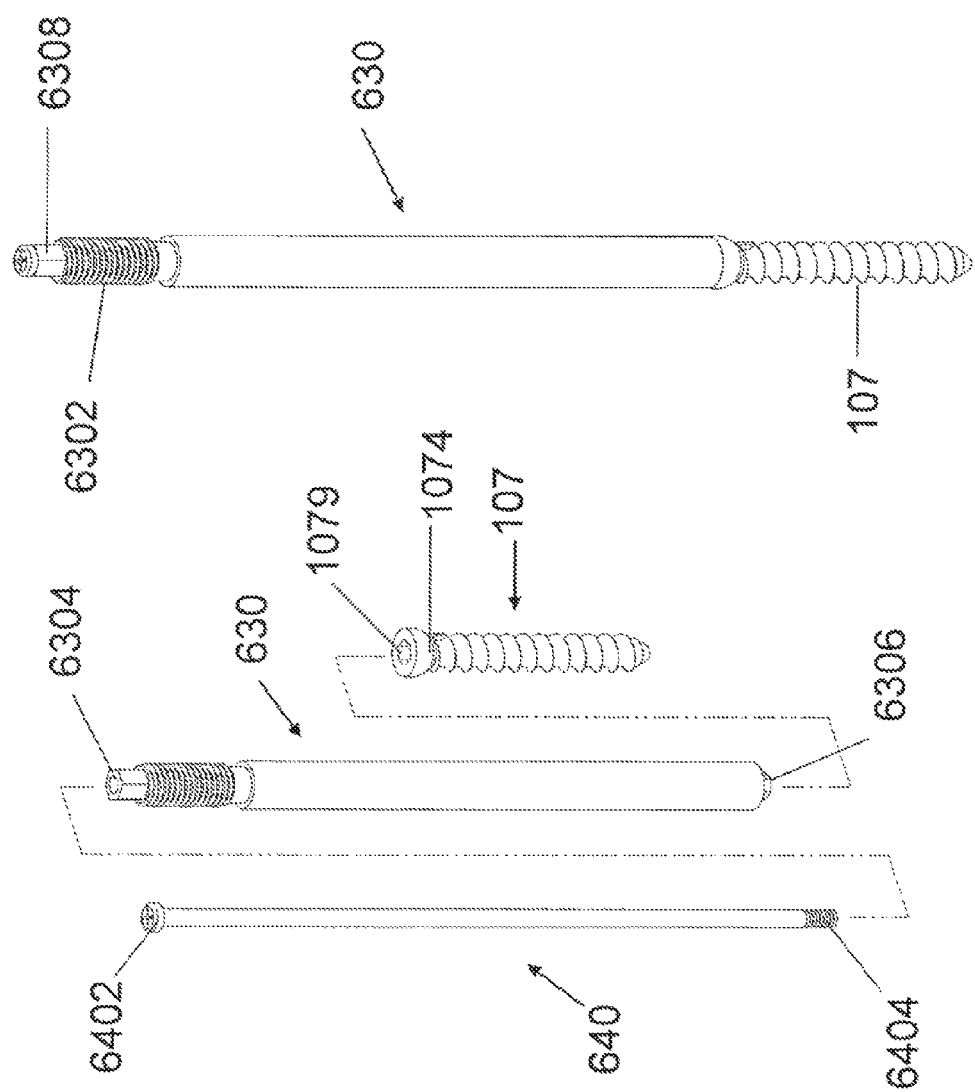
Fig. 43C
Fig. 43B
Fig. 43A

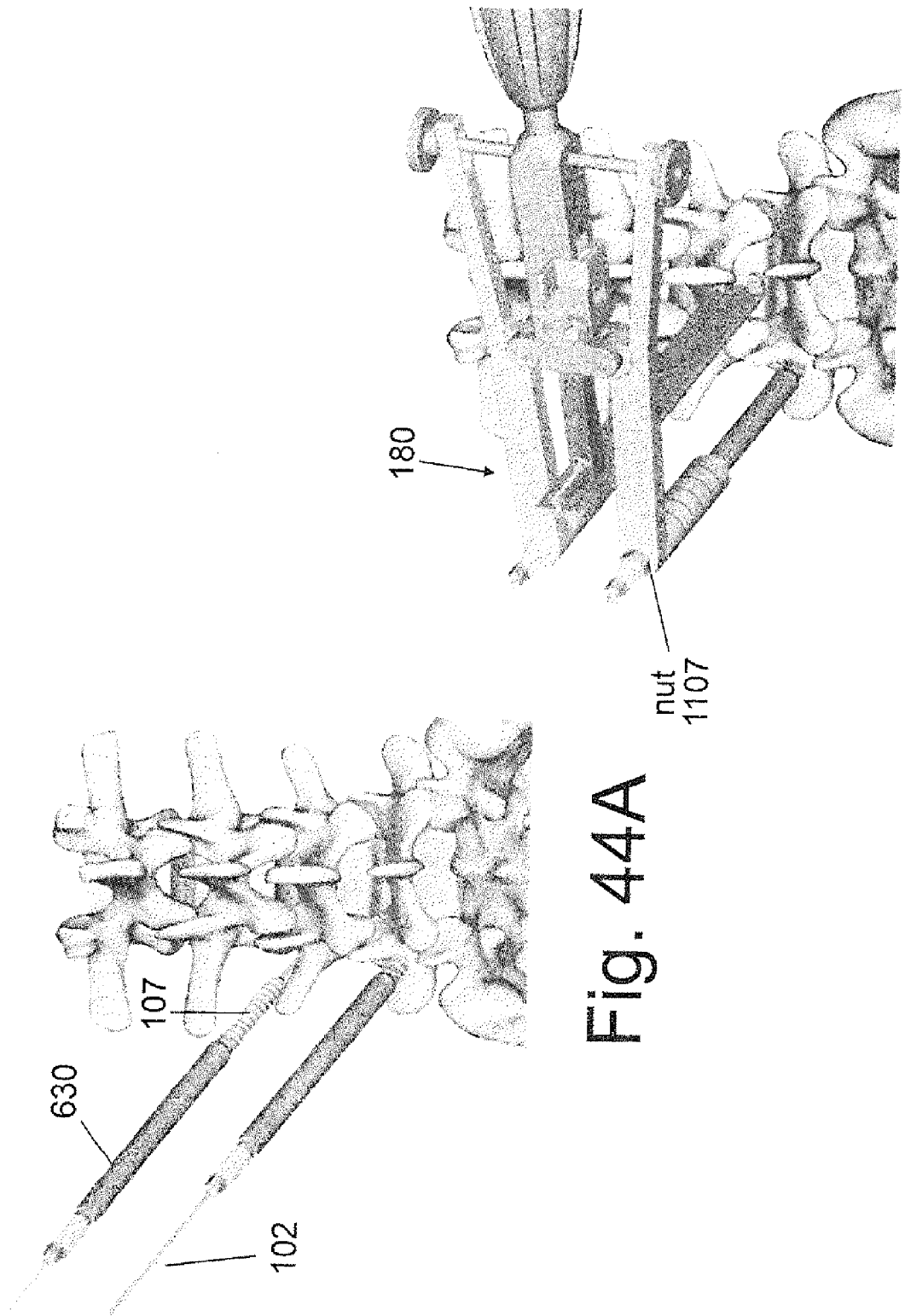

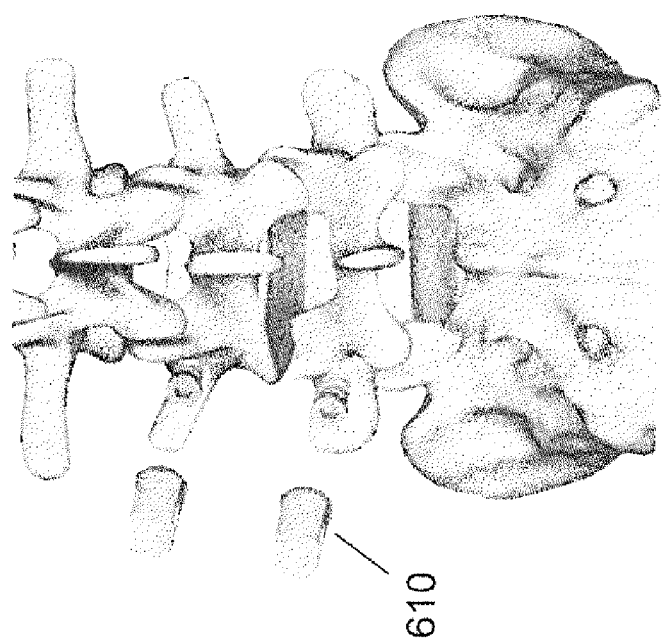
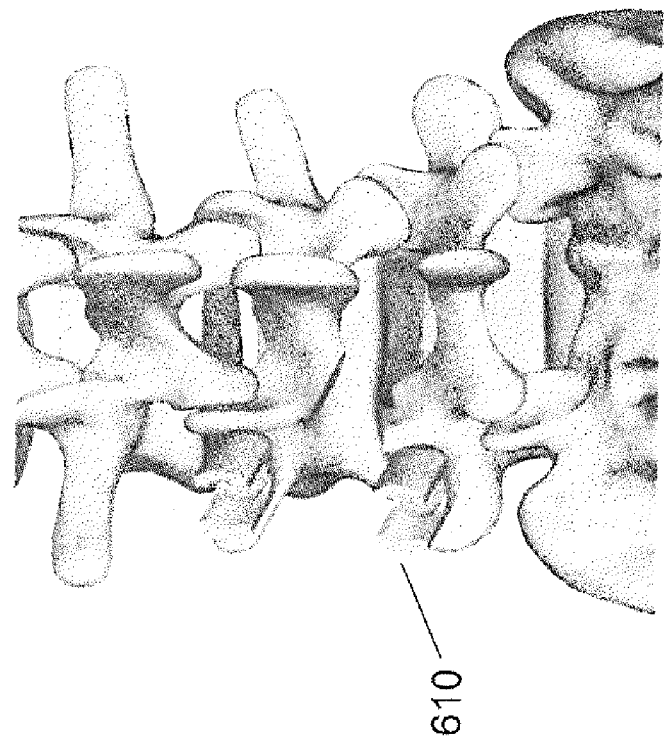
Fig. 45A
Fig. 45B

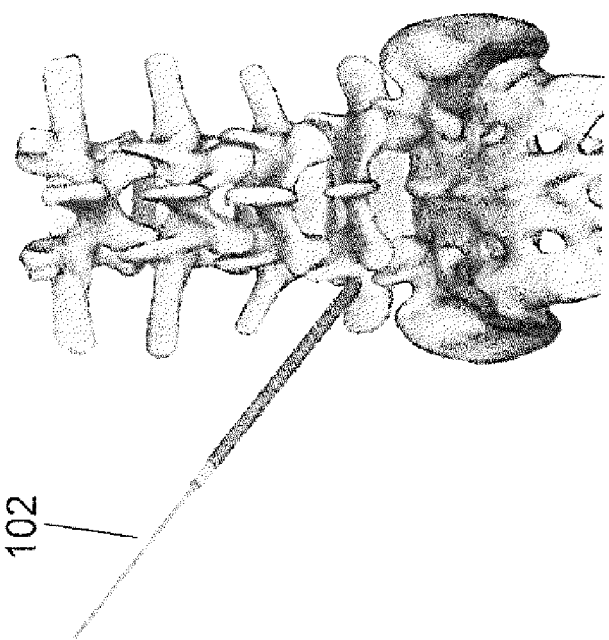
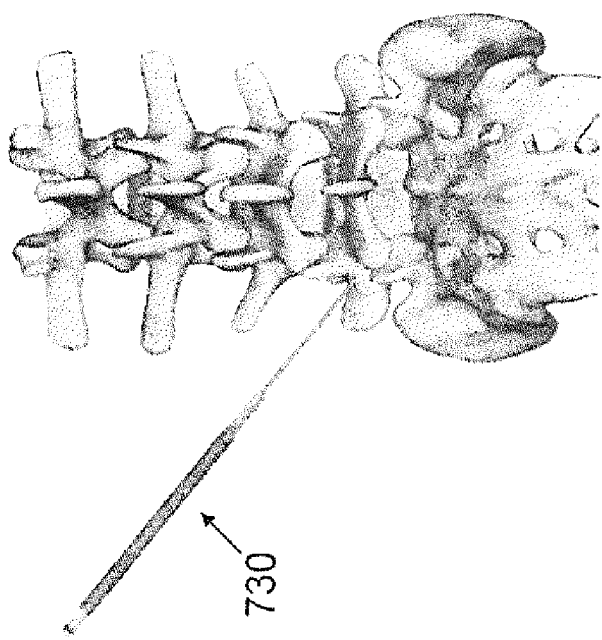

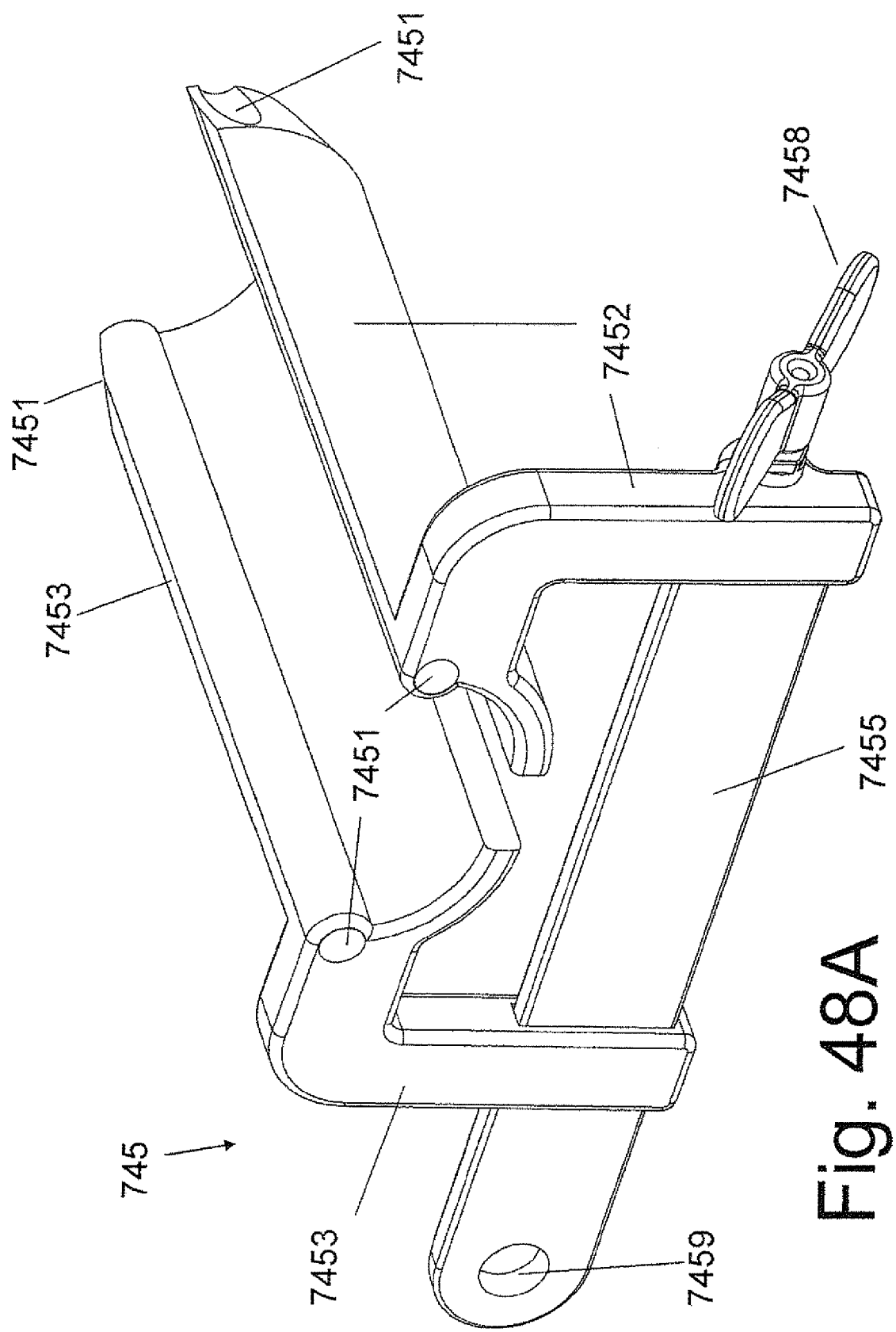

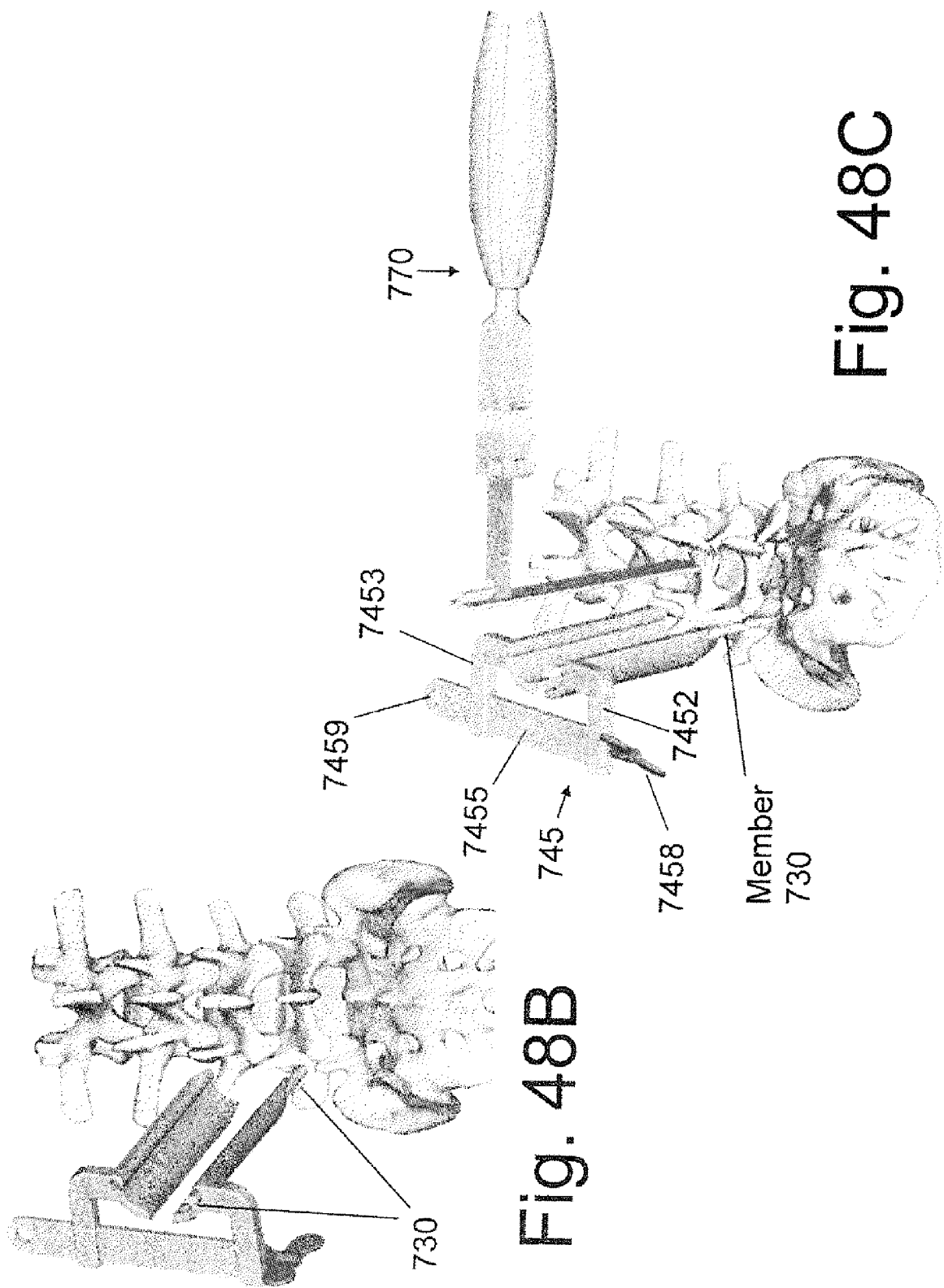

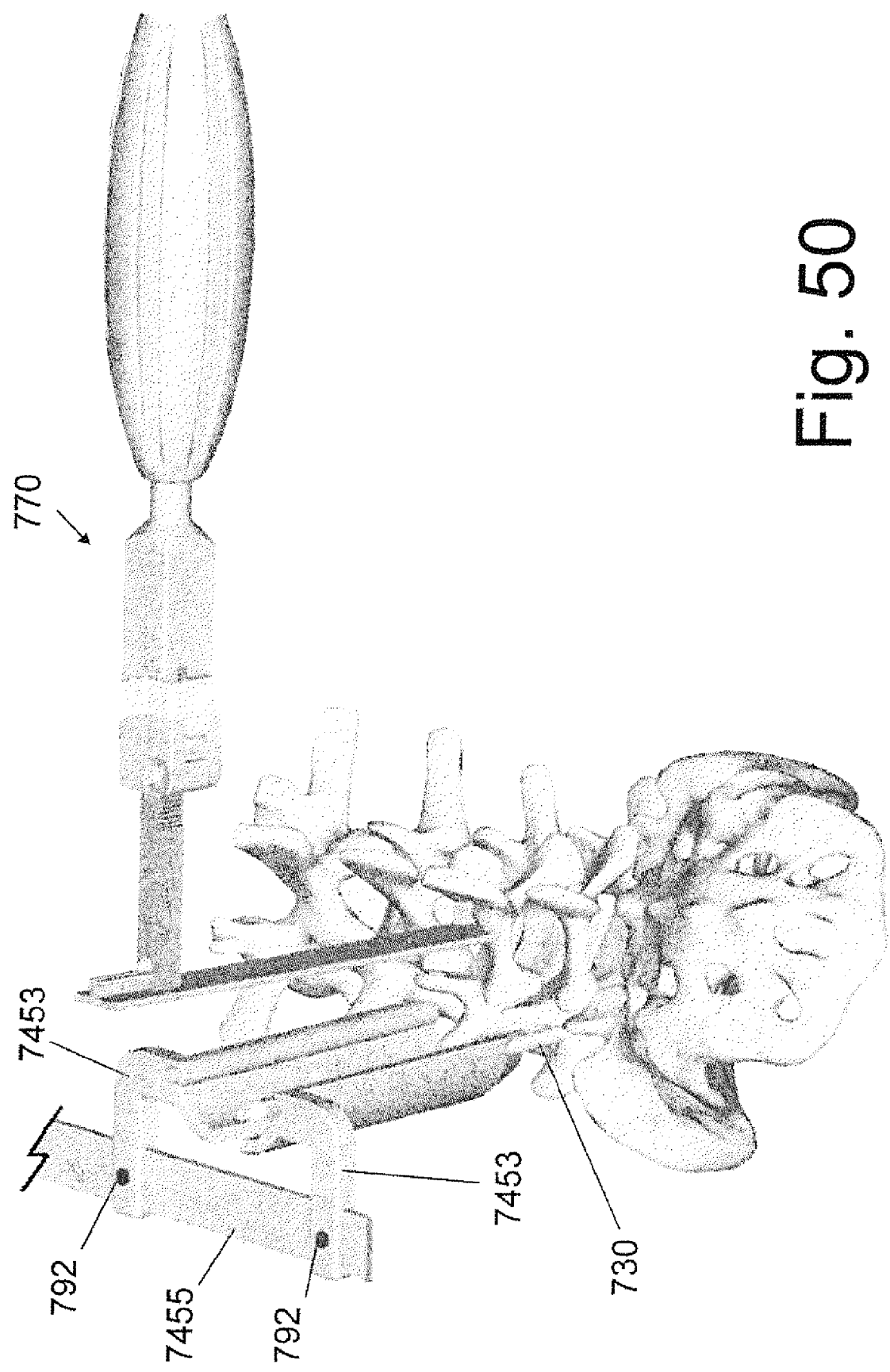

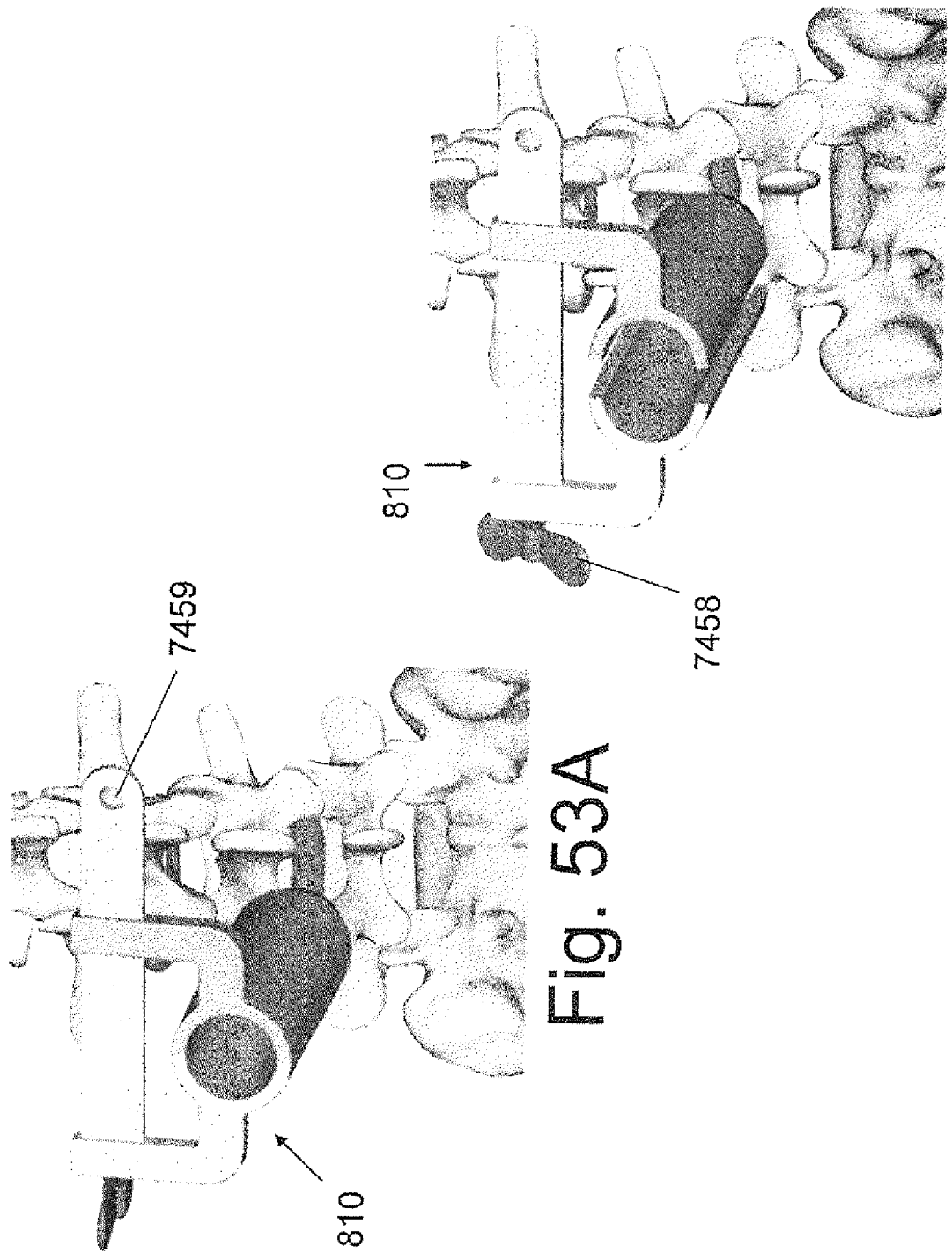

DEVICES AND METHODS FOR MINIMALLY INVASIVE SPINAL STABILIZATION AND INSTRUMENTATION

CROSS-REFERENCE TO PRIORITY DOCUMENT

This application is a continuation of and claims priority to co-pending U.S. patent application Ser. No. 12/962,534 filed on Dec. 7, 2010 of the same title, which is hereby incorporated by reference in its entirety, and which claims priority of co-pending U.S. Provisional Patent Application Ser. No. 61/283,745, entitled "Devices and Methods for Minimally Invasive Spinal Stabilization and Instrumentation", filed Dec. 7, 2009. Priority of the aforementioned filing date is hereby claimed and the disclosure of the provisional patent application is hereby incorporated by reference in its entirety.

BACKGROUND

Disclosed herein are devices, systems and methods of stabilization of the bony elements of the skeleton. These devices will permit adjustment and maintenance of the spatial relationship(s) between neighboring bones. Depending on the specifics of the design, the motion between skeletal segments may be immobilized completely or preserved.

Surgical reconstructions of the bony skeleton are common procedures in current medical practice. Regardless of the anatomical region or the specifics of the reconstructive procedure, many surgeons employ an implantable device that can adjust, align and maintain the spatial relationship(s) between adjacent bones.

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The current surgical treatment of abnormal vertebral motion is the complete immobilization and bony fusion of the involved spinal segment. An extensive array of surgical techniques and implantable devices have been formulated to accomplish this goal.

Vertebral fusion may be accomplished by using an anterior, lateral or posterior approach and each has particular advantages and draw backs. Frequently, circumferential fusion of the unstable level with fixation of both the anterior and posterior aspect of the spine is desired. This requires that patients undergo a combination of the aforementioned approaches. The anterior or lateral approaches are used to insert the bone graft into the disc space between the adjacent vertebras while the posterior approach is used to place bone screws or similar fasteners that are used to immobilize the vertebral bodies.

A Trans-foraminal Lumbar Interbody Fusion (TLIF) is known in the art to permit circumferential fusion of the spine through a single surgical approach. (The procedure is described in several literature citations, including: Transforaminal Lumbar Interbody Fusion by Alan Moskowitz, Orthop Clin N Am 33 (2002) 359-366. The article is hereby incorporated by reference in its entirety.)

The procedure requires an oblique approach to the posterior aspect of the spine. Unfortunately, an oblique operative corridor is less familiar to surgeons and contains fewer recognizable anatomical landmarks—leading to a higher rate of intra-operative confusion and loss of direction among operating surgeons. This difficulty is compounded when the procedure is performed using minimally invasive or percutaneous surgical technique, wherein the extent of tissue exposure is purposefully minimized. With the lack of surgical landmarks, the probability of intra-operative misdirection and the consequent development of surgical complications are necessarily increased.

In the current execution of the trans-foraminal lumbar interbody fusion (TLIF), the surgeon makes a skin incision posterior to the spinal level that is to be fused, develops a dissection corridor through the soft tissues adjacent to the spine and arrives at a facet joint of the spinal level to be fused. The facet joint is then at least partially removed in order to provide access to the posterior surface of the disc space which is positioned immediately anterior to the facet joint. The disc space is entered, prepared to accept fusion (preparation of the disc space is a well known procedure in the art and will not be described in detail here) and then implanted with the desired implant and material. After disc space implantation, the surgeon frequently, but not necessarily, desires to add supplemental orthopedic instrumentation to rigidly fixate the operative level while the bony fusion matures. Most commonly, the supplemental fixation involves placement of bone anchors (usually screws) that are interconnected with an interconnecting members (usually one or more rods).

In the current execution of the trans-foraminal lumbar interbody fusion (TLIF), it is the development of a dissection corridor through the soft tissues from the skin incision to the facet joint that is most likely to create disorientation and confusion. The surgeon often arrives at a bony prominence of the underlying vertebral bones but may be unclear as to which segment of the bone it is or the precise orientation of the soft tissue corridor relative to the vertebral bones that must be fused. The lack of reliable surgical landmarks during development of the oblique soft tissue corridor adds to the uncertainly and this difficulty is compounded when the procedure is performed using minimally invasive or percutaneous surgical technique, wherein the extent of tissue exposure is purposefully minimized.

SUMMARY

Provided herein are devices and methods for the safe and reproducible placement of an orthopedic implant into the disc space of a desired spinal segment. The disclosed procedure is especially well adapted for performing minimally invasive or percutaneous trans-foraminal lumbar interbody fusion (TLIF) procedures. However, while described for a posterior fusion technique of the lumbar spine, it is nevertheless understood that the devices and methods described herein may be used with any other applicable surgical approach to any applicable spinal level. Further, the devices and method may be used to implant non-fusion implants (such as artificial discs, replacement nucleus pulposis, and the like) into a targeted disc space.

The disclosed devices and methods include identifying and targeting a portion of a vertebral bone adjacent to the disc space to be implanted in the initial operative steps. A marker is advanced into the identified bony segment and the marker is used as a reference to orient the surgical corridor and to correctly identify the segments of bone and disc to be removed and/or manipulated. In a preferred embodiment that is illustrated in a TLIF procedure, the pedicle portion of the vertebral bone is the targeted segment of bone that is identified and marked. Preferably the pedicle is marked with a bone screw that is anchored into it and the pedicle and screw are then used to define and orient the subsequent operative steps. In another embodiment that is illustrated in the performance of a TLIF procedure, the facet joint is the targeted segment that is identified and marker. Preferably, the facet joint is marked with a bone screw that is anchored into it and the screw is then used to define and orient the subsequent operative steps.

Disclosed is a method wherein a segment of bone of at least one vertebra that borders the disc space to be implanted is identified intra-operatively by imaging techniques (X-rays, CT, MRI and the like). A marker, such as a bone screw, is placed into the identified bone segment and the attached marker forms a readily identifiable surgical land mark for the surgeon during formation of the surgical corridor. When illustrated in the performance of a TLIF procedure, the marker is preferably positioned into the pedicle or facet portion of the vertebral bone. The marker is coupled to bone prior to resection of the facet joint. The marker is used to define the exposure and orient the surgeon during the subsequent bony manipulation.

In the preferred embodiment, it is the pedicle portion of the vertebral bone that is localized and marked. The devices and methods described herein are illustrated in the performance of a minimally invasive trans-foraminal lumbar interbody fusion (TLIF) procedure, wherein a bone screw is placed into the identified pedicle and the bone screw forms a readily identifiable surgical land mark for the surgeon during formation of the surgical corridor to the facet joint and its subsequent removal.

Disclosed are distractor platforms and methods of use for the exposure and resection of at least a portion of the facet joint in performance of a TLIF procedure. In an embodiment, the distractor platform contains at least a first receptacle and/or extension that are adapted to couple to the implanted screw/bone marker. Preferably, the distractor platform also contains at least one retractor blade that is adapted to retract and retain the soft tissues that rest posterior to the facet joint so as to expose the posterior aspect of the joint. The tissue retractor blade may be reversibly detachable from the distractor platform and, preferably, the distance from tissue-retracting blade tip to the distractor platform may be varied so that the distractor blade is, in effect, of variable in length.

Provided herein are instruments and methods for the unambiguous introduction of surgical landmarks and corridors for placement of an orthopedic implant into the disc space of a spinal segment. Described herein are instruments and methods for placement of an orthopedic implant into the disc space of spinal segment using a trans-foraminal lumbar interbody fusion (TLIF) procedure, wherein the TLIF procedure is preferably performed in a minimally invasive or percutaneous manner. While illustrated in the TLIF approach, it is understood that the illustrated embodiments are not restrictive and the instruments and methods may be used with any other applicable surgical approach and at any applicable spinal level.

In one aspect provided is a method for fusion of a first vertebral bone and a second adjacent vertebral bone of a subject. The method includes identifying a first pedicle of the first vertebral bone on radiographic imaging; identifying the second adjacent vertebral bone on radiographic imaging and a first facet joint. The first facet joint forms an articulation between the first vertebral bone and the second adjacent vertebral bone. The first facet joint resides on the same side of the vertebral midline as the identified first pedicle of the first vertebral bone. The method also includes advancing a first threaded segment of a first bone fastener assembly into the identified first pedicle of the first vertebral bone. The first bone fastener assembly further includes a second segment that is adapted to couple with a distraction platform. The method also includes coupling the distraction platform with the second segment of the first bone fastener assembly. The distraction platform is adapted to concurrently attach onto at least one tissue retention blade. The method further includes positioning the tissue retention blade in proximity to the first bone fastener assembly that is anchored to the pedicle of the first vertebral bone; exposing the first facet joint by applying a force to displace the tissue retention blade away from the first bone fastener assembly and towards the vertebral midline. The distraction platform is adapted to retain the tissue retention blade in the displaced position. The method also includes removing at least a segment of the first facet joint and exposing a posterior surface of an intervertebral disc space. The exposed disc space is positioned between the first and second vertebral bones. At least a portion of exposed disc surface is immediately anterior to the removed portion of the first facet joint. The method also includes entering the posterior aspect of the disc space through a trans-foraminal corridor and removing the distraction platform. The entry point of the posterior disc is at least partially in between the nerve root that exits the spinal canal beneath the pedicle of the superior vertebral bone and the pedicle of the inferior vertebral bone; positioning an implant into the disc space. The implant can bear at least some of the load transmitted across the disc space and maintain the superior and inferior vertebral bones separated by a desired distance.

In another aspect, there is disclosed a method for the fusion of a first vertebral bone and a second adjacent vertebral bone of a subject. The method includes identifying the first vertebral bone on radiographic imaging and a first facet joint, wherein the first facet joint forms an articulation between the first and second adjacent vertebral bones; advancing a first threaded segment of a first bone fastener into the identified first facet joint under radiographic guidance, wherein the bone fastener is threadedly anchored onto the first facet joint; using the anchored first bone fastener to guide and position a retraction platform; advancing a distraction platform over the anchored first bone fastener and onto the facet joint, wherein the distraction platform is coupled to at least two tissue retention extensions; detaching the first bone fastener from the facet joint in order to form a corridor between the tissue retention extensions of the distraction platform, wherein the corridor permits direct access to the posterior aspect of the first facet joint; identifying visually the first facet joint at the distal end of the corridor between the tissue retention extensions of the distraction platform; removing at least a segment of the first facet joint and exposing a posterior surface of an intervertebral disc space, wherein the exposed disc space is positioned between the first and second vertebral bones, wherein at least a portion of exposed disc surface is immediately anterior to the removed portion of the first facet joint; entering the posterior aspect of the disc space through a trans-foraminal corridor, wherein the entry point of the posterior disc is at least partially in between the nerve root that exits the spinal canal beneath the pedicle of the superior vertebral bone and the pedicle of the inferior vertebral bone; positioning an implant into the disc space, wherein the implant can bear at least some of the load transmitted across the disc space and maintain the superior and inferior vertebral bones separated by a desired distance; and removing the distraction platform.

In another aspect, a method for stabilization of a spinal segment having a first vertebral bone, a second vertebral bone, and an intervening intervertebral disc space is disclosed. In one embodiment, the method comprises: (i) approaching a posterior aspect of the intervertebral disc space, (ii) creating an opening in a posterior aspect of an annulus fibrosis of the intervertebral disc space, (iii) advancing an anterior surface of an orthopedic implant through the opening in the annulus fibrosis, the orthopedic implant configured to extend from the anterior surface to a posterior surface along an at least partially curvilinear axis, the orthopedic implant further comprising a first side surface and a second side surface each configured to extend along a curvilinear trajectory having a center of rotation positioned ipsilateral to the first side surface, and (iv) advancing a remainder of the orthopedic implant into the intervertebral disc space, the advancement following a circular trajectory centered at an axis of rotation positioned ipsilateral to the first side surface.

In another embodiment, the method comprises: (i) creating an opening in a posterior aspect of an annulus fibrosis of an intervertebral disc space of the living subject, (ii) advancing a first portion of a curvilinear orthopedic implant through the opening, and (iii) rotating the curvilinear orthopedic implant about an axis of rotation ipsilateral to an ipsilateral side surface of the curvilinear orthopedic implant. The rotation of the curvilinear orthopedic implant causes the implant to be positioned within the intervertebral disc space of the living subject.

In yet another aspect, an orthopedic implant is disclosed. In one embodiment, the implant comprises: a curvilinear body member comprising at least a first ipsilateral side surface and an opposing contra-lateral side surface. The curvilinear body is configured to extend along a curvilinear trajectory having a center of rotation positioned ipsilateral to the first ipsilateral side surface. The curvilinear shape of the body member is such that the first ipsilateral side surface is substantially concave relative to the center of rotation. The curvilinear body is configured to be advanced into an intervertebral disc space of a subject via rotation thereof about a circular trajectory centered at the center of rotation.

Other features and advantages should be apparent from the following description of various embodiments, which illustrate, by way of example, the principles of the disclosed instruments and methods.

BRIEF DESCRIPTION OF THE DRAWINGS

FIG. 14 shows an embodiment of a distraction platform.

FIGS. 15A-15C show various views of the platform.

FIGS. 23-24 show distraction arms positioned within the incision between each of the fastener coupler members.

FIG. 25A-25D show various perspectives of the working corridor.

FIG. 35 shows schematic view of the dural sac and contained nerve element decompressed on the posterior and lateral aspects.

FIGS. 36A-36B show an embodiment of a disc implant.

FIG. 37 shows an implant having at least one cavity that pet communication from one side of the implant body to the other.

FIGS. 41A-41B show schematic sequence of inter-connecting member used to interconnect fasteners.

FIGS. 43A-43C show an example of a device adapted to perform the method.

FIGS. 44A-44B show steps in the assembly onto the distractor platform.

FIGS. 45A-45B show schematically the housing members attached to the bone screws.

FIGS. 47A-47B show another embodiment of threaded screw member used to anchor distraction platform to pedicle portion of vertebral bone.

FIGS. 48A-48C show a retractor platform.

FIG. 50 shows another embodiment of a retractor.

FIGS. 53A-53B show tube removed leaving a working corridor within the central aspect of the semi-cylindrical retractor blades.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the invention is thereby intended. Any such alterations and further modifications in the illustrated embodiments, and any such further applications of the principles of the invention as illustrated herein are contemplated as would normally occur to one of ordinary skill in the art.

Figure 1:
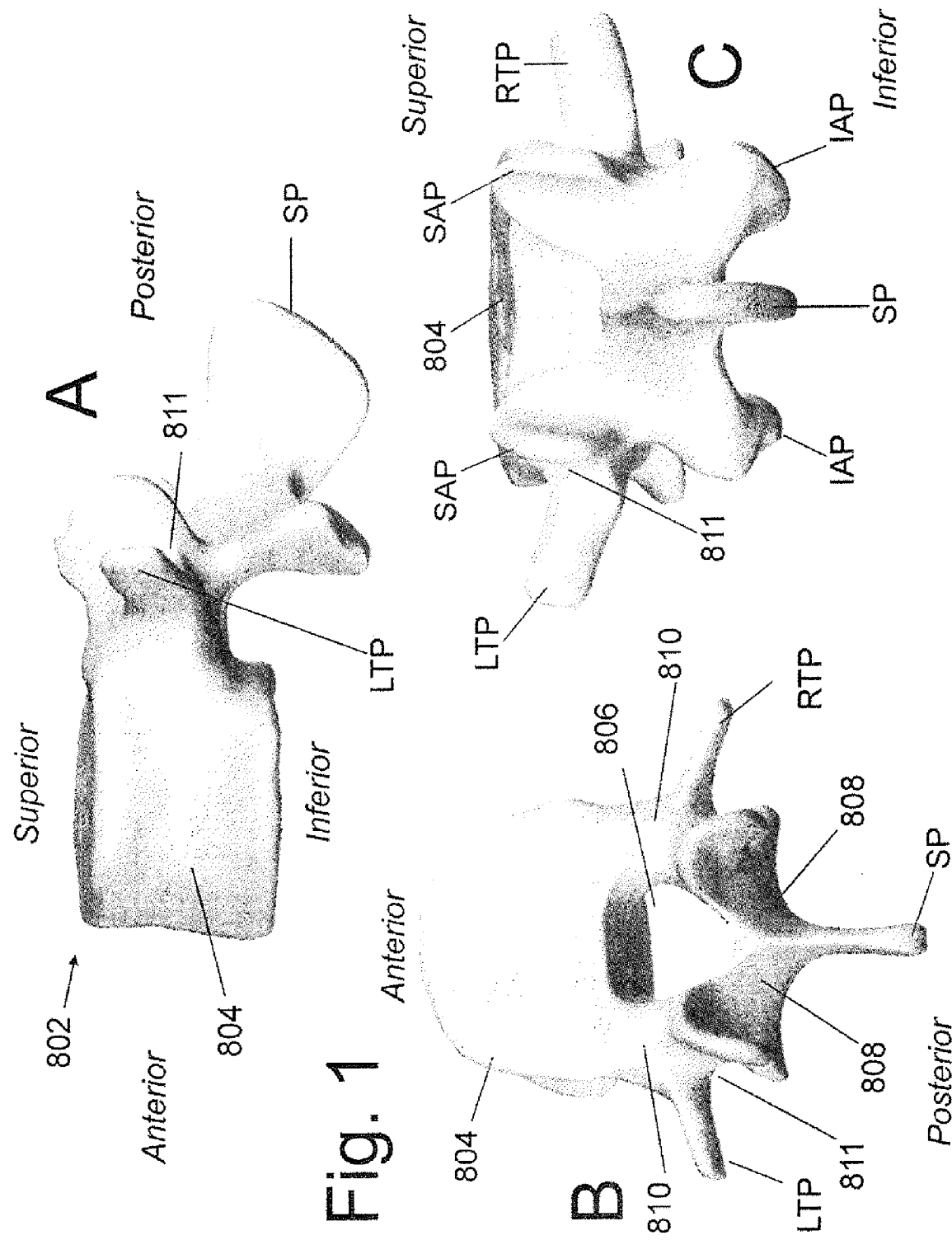
FIGS. 1A-1C show diagrammatic representations of a spinal vertebral bone in multiple views.

FIG. 1 shows a diagrammatic representation of a spinal vertebral bone 802 in multiple views. For clarity of illustration, the vertebral bone of FIG. 1 and those of other illustrations presented in this application are represented schematically and those skilled in the art will appreciate that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. Thus, the disclosed devices and methods may be applied at any applicable spinal level.

Vertebral bone 802 contains an anteriorly-placed vertebral body 804, a centrally placed spinal canal and 806 and posteriorly-placed lamina 808. The pedicle (810) segments of vertebral bone 802 form the lateral aspect of the spinal canal and connect the laminas 808 to the vertebral body 804. The spinal canal contains neural structures such as the spinal cord and/or nerves. A midline protrusion termed the spinous process (SP) extends posteriorly from the medial aspect of laminas 808. A protrusion extends laterally from each side of the posterior aspect of the vertebral bone and is termed the transverse process (TP). A right transverse process (RTP) extends to the right and a left transverse process (LTP) extends to the left. A superior protrusion extends superiorly above the lamina on each side of the vertebral midline and is termed the superior articulating process (SAP). An inferior protrusion extends inferiorly below the lamina on each side of the vertebral midline and is termed the inferior articulating process (IAP). Note that the posterior aspect of the pedicle can be accessed at an indentation 811 in the vertebral bone between the lateral aspect of the SAP and the medial aspect of the transverse process (TP). In surgery, it is common practice to anchor a bone fastener into the pedicle portion of a vertebral bone by inserting the fastener through indentation 811 and into the underlying pedicle.

Figure 2:
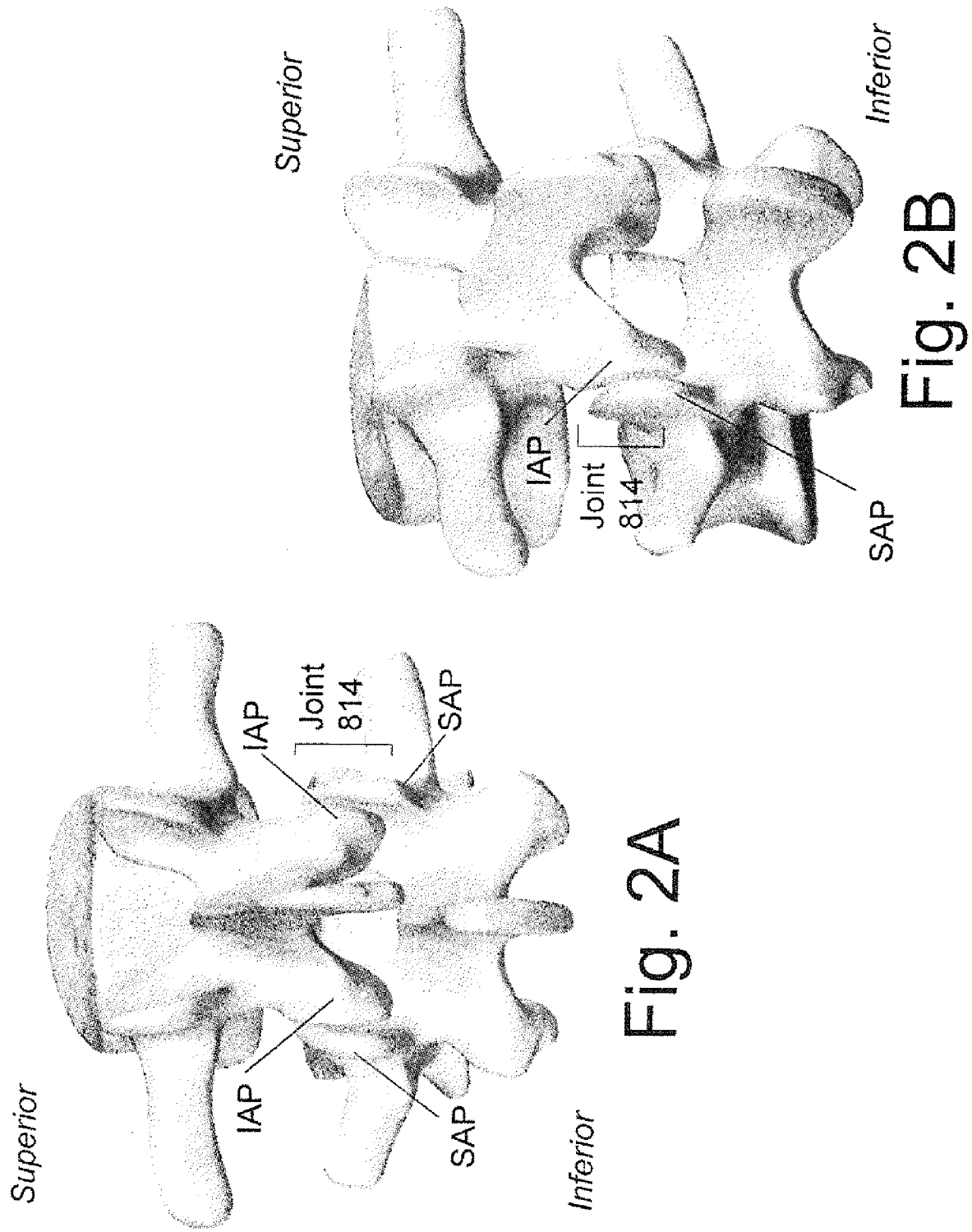
FIGS. 2A and 2B illustrate a functional spinal unit (FSU), which includes two adjacent vertebrae and the intervertebral disc between them.

FIGS. 2A and 2B illustrate a functional spinal unit (FSU), which includes two adjacent vertebrae and the intervertebral disc between them. The intervertebral disc resides between the inferior surface of the upper vertebral body and the superior surface of the lower vertebral body. (Note that a space is shown in FIGS. 2A and 2B where intervertebral disc would reside.) FIG. 2A shows the posterior surface of the adjacent vertebrae and the articulations between them while FIG. 2B shows an oblique view. Note that the FSU contains a three joint complex between the two vertebral bones, with the intervertebral disc comprising the anterior joint. The posterior joints include a facet joint 814 on each side of the midline, wherein the facet joint contains the articulation between the IAP of the superior vertebral bone and the SAP of the inferior bone.

The preceding illustrations and definitions of anatomical structures are known to those of ordinary skill in the art. They are described in more detail in *Atlas of Human Anatomy*, by Frank Netter, third edition, Icon Learning Systems, Teterboro, N.J. The text is hereby incorporated by reference in its entirety.

Illustrated are methods and devices that permit a surgeon to access the anterior column of the spine from a posterior skin incision through a transforaminal surgical approach. The "anterior column" is used here to designate that portion of the vertebral body and/or FSU that is situated anterior to the posterior longitudinal ligament (PLL)—and may include the PLL. Thus, its use in this application encompasses both the anterior and middle column of Denis. (See *The three column spine and its significance in the classification of acute thoracolumbar spinal injuries*. By Denis, F. *Spine* 1983 November-December; 8(8):817-31. The article is incorporated by reference in its entirety.)

It is a purpose of the present invention to provide instruments and methods for the unambiguous introduction of surgical landmarks and corridors for placement of an orthopedic implant into the disc space of a spinal segment. It is a purpose of the present invention to specifically illustrate the instruments and methods for placement of an orthopedic implant into the disc space of spinal segment using a trans-foraminal lumbar interbody fusion (TLIF) procedure, wherein the TLIF procedure is preferably performed in a minimally invasive or percutaneous manner. While illustrated in the TLIF approach, it is understood that the illustrated embodiments are not restrictive and the instruments and methods may be applied at other spinal segments and to methods of implant placement other than TLIF.

For a functional spinal unit (FSU) that has been targeted for placement of an orthopedic implant into the intervening disc space, the trans-foraminal lumbar interbody fusion (TLIF) procedure requires removal of at least a portion of the IAP and SAP of a facet joint 814 that is immediately posterior to the disc space to be implanted. The facet joint removal may be performed on one side of the vertebral midline, the opposite side of the vertebral midline or on both sides of the vertebral midline. In the existing art, a TLIF procedure is started with development of an oblique soft tissue corridor from the skin incision site (which is posterior to the spine) to the facet joint that must be removed. Unfortunately, the soft tissue corridor lacks adequate surgical landmarks and its development can cause intra-operative confusion, misdirection and deviation into unintended structures. This difficulty is compounded when the procedure is performed using minimally invasive or percutaneous surgical technique.

It is a goal of the current invention to obviate any intra-operative confusion by placing bone markers and/or fasteners in at least one prescribed location of the vertebral bones of the targeted FSU. In a preferred embodiment, the pedicle portion of the upper and/or lower vertebral bones that border the disc space targeted for implantation are identified and localized on imaging (such as X-rays, CT, MRI and the like). Bone screws and/or other fasteners are then advanced in a percutaneous manner and under image guidance (such as X-rays, CT, MRI and the like) into the pedicle portion of the localized vertebrae through small skin incisions. Alternatively, a small posterior skin incision can be made overlying the posterior aspect of the disc space targeted for implantation. The bone screws and/or fasteners can then be advanced through the small incision, in a minimally invasive way, onto the bone insertion region 811 and into the underlying the pedicle. In another embodiment, the bone fasteners may be placed at the bone insertion site 811 with conventional surgical technique and a larger skin incision. The bone screws and/or fasteners are then used to guide the formation of the surgical corridor to the facet joint.

Placement of the bone fasteners before resection of the facet joint differs from the method of current art, wherein the facet joint is accessed/resected and an implant is positioned into the disc space without prior placement of the bone screws and/or fasteners. That is, in the current invention, bone markers are positioned to define the surgical corridor without prior resection of facet joint. In contrast, the current art does not use fasteners to define the surgical corridor to the facet joint nor are they used to guide implant placement.

After bone screw and/or fastener (hereinafter the terms are used interchangeably) placement, a distraction platform is used to couple and/or attach onto at least one of the bone screw assemblies. In a preferred embodiment, the distraction platform has at least one additional distraction arm that is adapted to retract soft tissues (skin, fat, muscle, etc). In specific, the distraction platform is coupled to each of the bone screws that have been advanced into the pedicle of the superior and inferior vertebral bones of the targeted FSU. Another arm member that is attached to the distraction platform is used to retract medially the soft tissues between the pedicle bone screws and the spinous process of the vertebrae of the targeted FSU. In this way, the facet joint 814 that lies immediately medial and between the two implanted pedicle bone screws is exposed. Using the bone screws as a coupling point for the distractor platform permits the pedicles and the anchored screws to be used as a surgical landmark in development of soft tissue corridor to the targeted facet joint. Use of another arm member that is coupled to the distraction platform to retract the soft tissues medially insures that the facet joint is readily and reproducibly exposed. It also obviates the possibility of intra-operative confusion by the surgeon.

The soft tissue retractor arm of the distraction is preferably, but not necessarily, removable. That is, the soft tissue retraction arm can be completely de-coupled and removed from the distraction platform. This provides maximal degree of versatility for the surgeon. After exposure of the facet joint 814 that is ipsilateral to the implanted bone screws, at least a portion of that facet joint is then removed. This is preferably, but not necessarily, performed by at least a combination of drill/burr removal and rongeur cutting of the bone so as to form a corridor within the facet joint that permits direct access of the segment of the disc space that is anterior to the removed joint. In an embodiment, the combination drilling and cutting of the facet joint may be performed by a single instrument. For example, the instrument may be adapted to permit bone removal by advancing a drill or burr through a central port of the instrument. The instrument may be further adapted to cut bone with sharpened edges—as would a bone rongeur.

After removal of the facet bone, the posterior disc space is accessed through a transforaminal corridor. The trans-foraminal corridor extends in the superior-inferior direction for a distance D1. Distance D1 extends from the inferior aspect of the nerve root that exits the spinal canal beneath the pedicle of the superior vertebral bone and the superior aspect of the pedicle of the inferior vertebral bone of the targeted FSU. The trans-foraminal corridor is bordered medially by the lateral aspect of the nerve root that exits the spinal canal beneath the pedicle of the inferior vertebral bone of the targeted FSU. A segment of the posterior aspect of the disc space that is exposed after facet resection is positioned immediately anterior to the trans-foraminal corridor. While described for completeness, the trans-foraminal corridor is known to those of ordinary skill in the art and may contain anatomical features that are not recounted here.

The posterior aspect of the disc space that is immediately anterior to the trans-foraminal corridor is entered by creation of a defect in the Annulus Fibrosis. At least partial removal of the disc material is performed and the bony endplate of each of the inferior surface of the superior vertebral bone and superior surface of the inferior vertebral bone are striped of cartilage material and then decorticated. Bone graft or bone graft substitute (hereafter collectively referred to as bone forming material) is then implanted into the evacuated disc space. Preferably, but not necessarily, an implant is concurrently implanted into the disc space that can bear at least some of the load transmitted across the disc space and maintain the superior and inferior vertebral bones separated by a desired distance. In an embodiment, the implant may be solid or it may contain a cavity adapted to house bone graft material, wherein the graft material is adapted to fuse with one or both of the vertebral bones.

After advancement of the implant into the targeted disc space, the distraction platform is removed. An inter-connecting member that is preferably, but not necessarily, a rod, is used to interconnect each of the superior and inferior bone fasteners. A locking element of each bone fastener is then deployed so that each bone fastener is rigidly attached to the interconnecting member. In this way, the fasteners and inter-connecting rod member will rigidly interconnect and immobilize the superior and inferior vertebral bones that abut the implanted disc space. Additional immobilization may be produced by the implantation of fasteners/interconnecting member into the contra-lateral vertebral pedicles (i.e., on the contra-lateral side of the vertebral midline). A spinous process fastener that is adapted to rigidly affix to the spinous process of each of the superior and inferior vertebral bones and rigidly immobilize the FSU may be alternatively used instead of implantation of the contra-lateral pedicle bone screws and interconnecting rod. (spinous process fixation plates and fasteners are known in the art. Among others, U.S. Pat. Nos. 6,582,433, 7,048,736 and US patent application publication numbers US 2007/0270840 and US 2008/0183211 all disclose spinous process fixation implants that may be applicable. Each of these patents/applications is hereby incorporated by reference in its entirety.)

The preferred embodiment is now described in detail and reference is made to the accompanying drawings. While the disclosed devices may be positioned in an appropriate spinal level/segment using any appropriate surgical method and/or surgical corridor, the following disclosure illustrates implant placement into a disc space of a functional spinal unit (FSU) using a posterior skin incision (posterior to spine) and a transforaminal lumbar interbody fusion (TLIF) technique.

Figure 3:
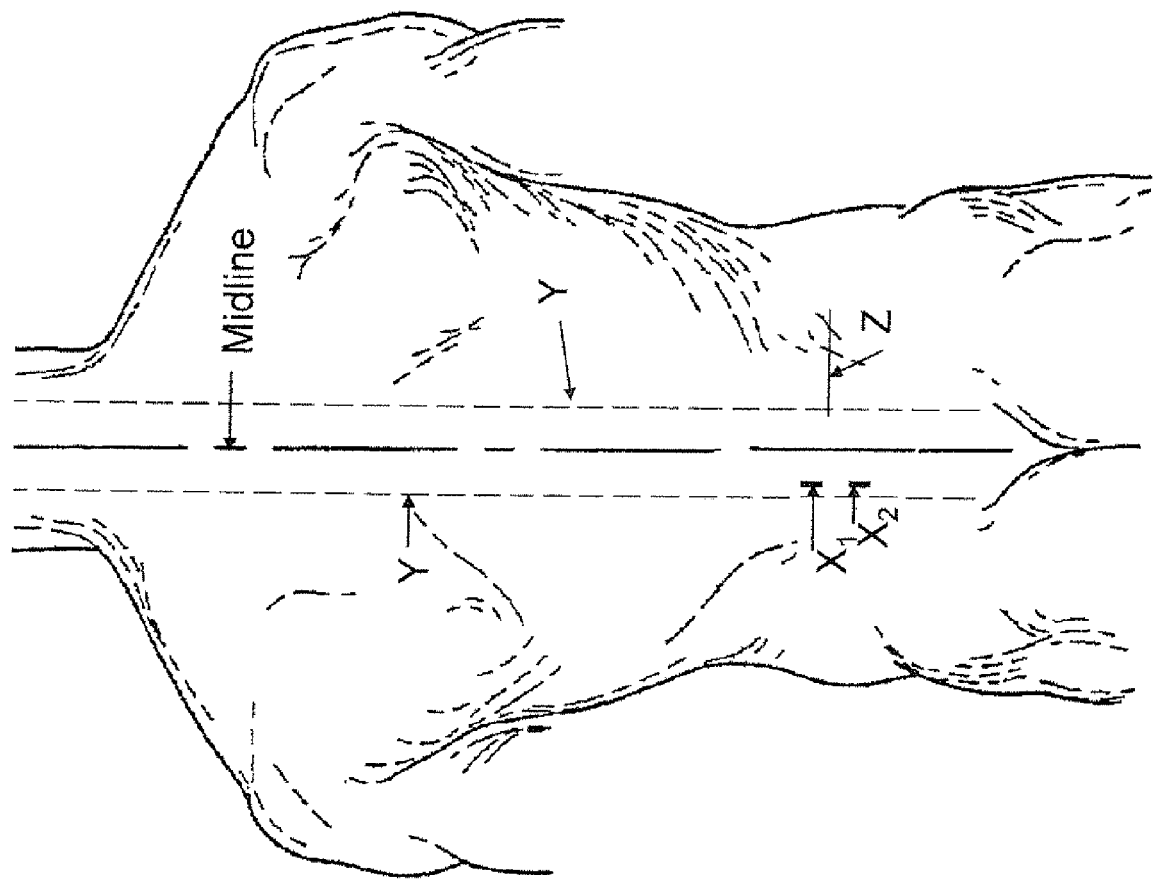
FIG. 3 shows a schematic representation of the posterior aspect of a patient who is positioned prone.

In preparation for the minimally invasive placement of the implant into a targeted spinal level, the patient is preferably, but not necessarily, placed in a prone position or in a lateral decubitus position. The level of the spine that is to be implanted is localized by imaging techniques (X-rays, CT, MRI and the like) in at least one plane. After the customary sterile preparation of the operative site, the surgeon localizes the incision points on the skin that are substantially lateral to vertebral midline and overlying the approximate spinal segment that will be implanted. FIG. 3 shows a schematic representation of the posterior aspect of a patient who is positioned prone. The skin overlying the back is shown. Lines Y illustrate a region that is approximately lateral to the midline and medial to the lateral extent of the transverse processes of the spinal column. Assuming that the spinal disc space to be accessed is skin line Z, the surgeon will access skin region $X_1$ that approximately overlies indentation 811 of the superior vertebral bone and skin region $X_2$ that approximately overlies indentation 811 of the inferior vertebral bone of the FSU that contains the targeted disc space. However, it is understood that one or more skin incisions of any sufficient length may be alternatively used.

Figure 4:
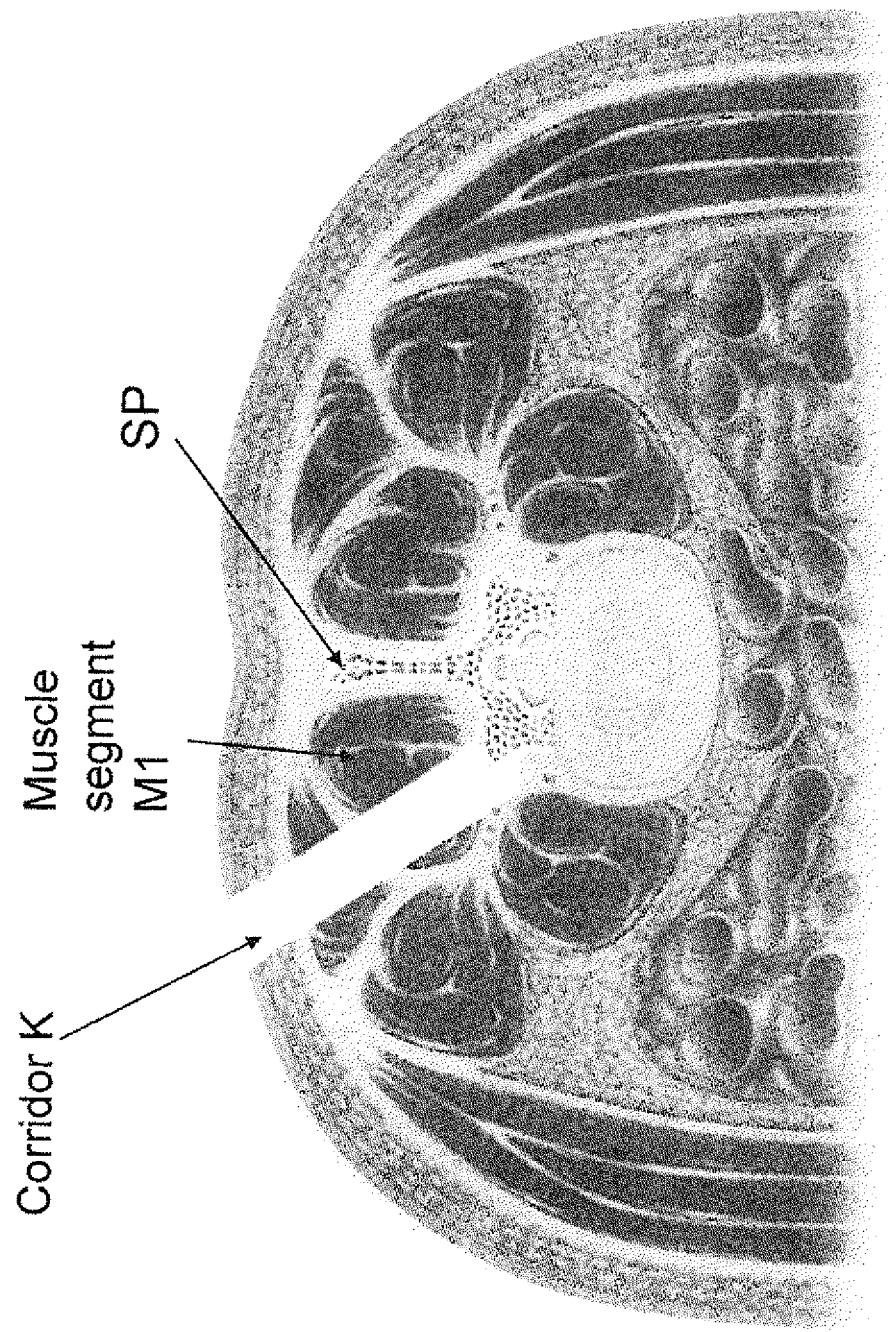
FIG. 4 illustrates a cross sectional view of the torso at the level of a targeted disc space in the lumbar spine.

Bone screws are placed into the pedicle portion of each of the superior and inferior vertebral bones by penetrating the bony surface at approximately indentation 811. In the preferred embodiment, the bone screw placement is performed in a percutaneous manner and under image guidance (such as X-ray, CT or MRI guidance and the like). Alternatively, the bone fasteners may be placed using a larger incision and minimally invasive surgery or full open (conventional) surgical technique. In general, each fastener follows an oblique corridor through the soft tissues between the skin entry site (wherein the skin entry site is posterior to the spine) and the bone entry point of indentation 811. An approximation of the soft tissue corridor K taken by the fasteners is shown in FIG. 4. FIG. 4 illustrates a cross sectional view of the torso at the level of a targeted disc space in the lumbar spine. For clarity of illustration, the contents are represented schematically and those skilled in the art will appreciate that an actual cross section of the human torso may include anatomical details not shown in FIG. 4.

Figure 6:
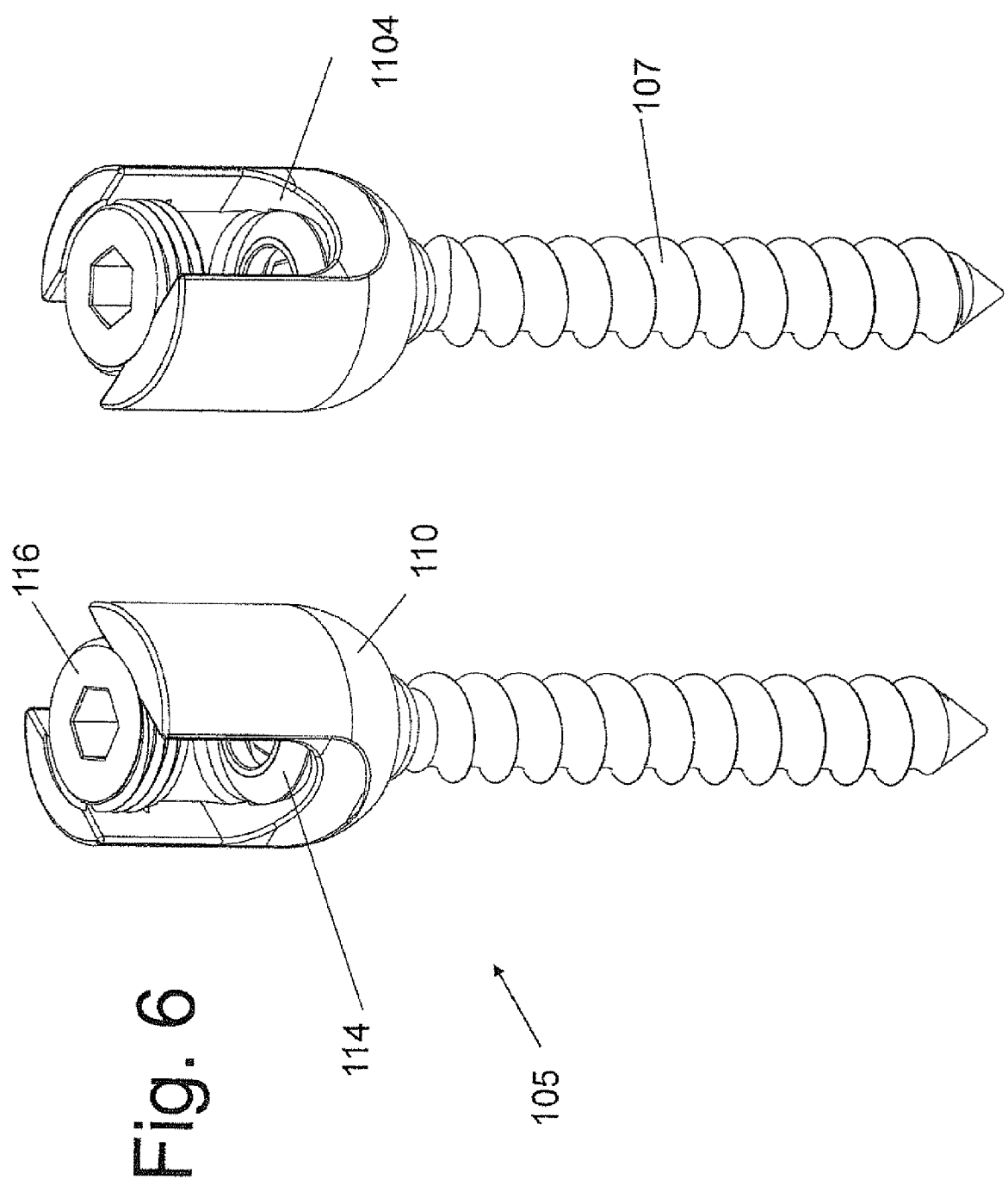
FIG. 6 shows perspective views of bone fastener.
Figure 7:
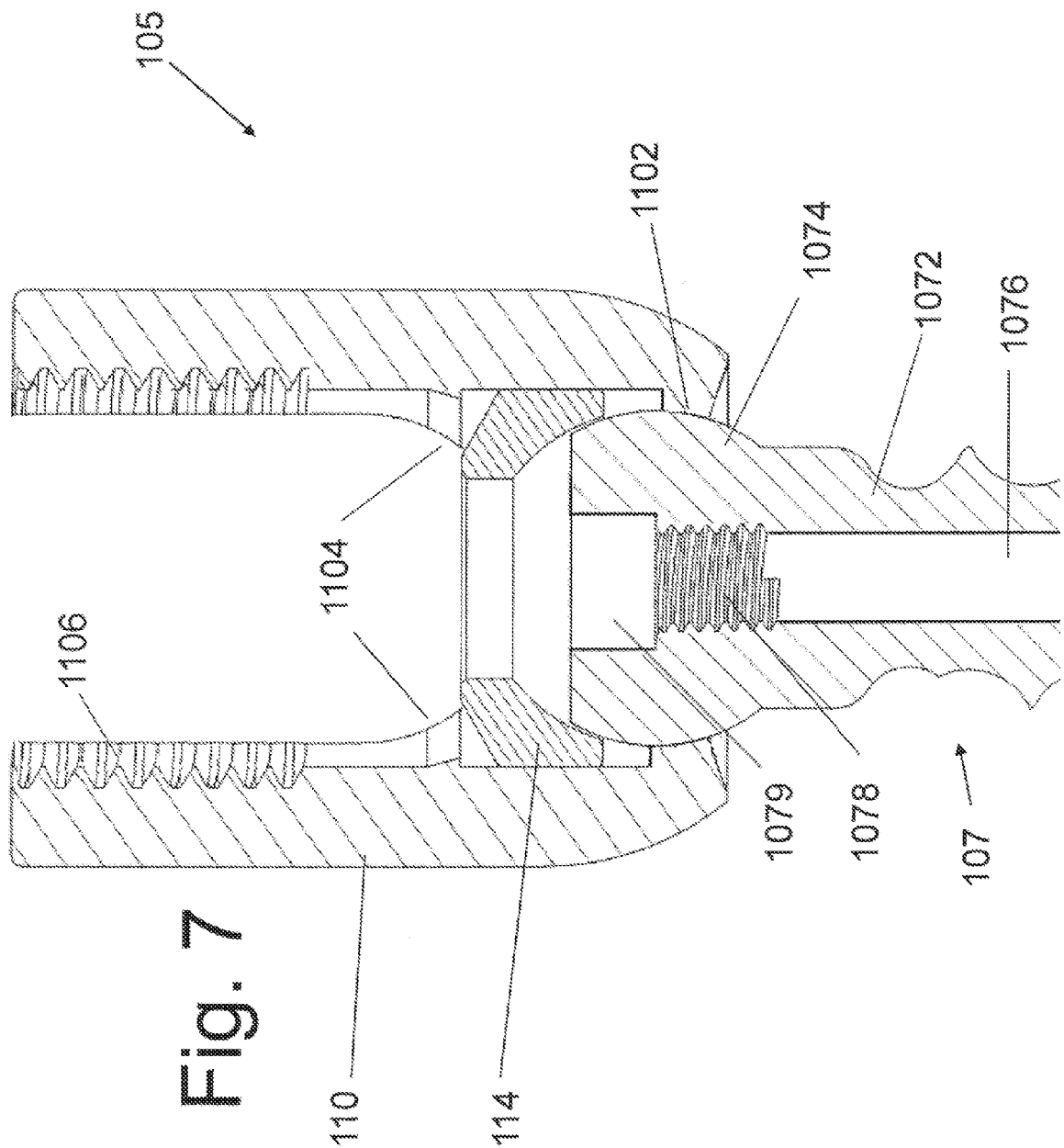
FIG. 7 shows a close-up section view of the fastener of FIG. 6.

FIGS. 5*a* and *b* show a representative bone screw assembly 105 and coupling device 125 and 130. FIG. 6 shows perspective views of bone fastener 105 while FIG. 7 shows a close-up section view of fastener 105. The bone fastener and coupling instruments are shown in additional detail in FIGS. 8 & 9. However, it should be appreciated that these embodiments are illustrative and there is known in the art many bone fasteners and couplers that may be alternatively used in the method disclosed in this application. (For example, U.S. RE37665, U.S. Pat. No. 6,248,105, U.S. Pat. No. 6,371,957, U.S. Pat. No. 6,565,565 all discloses at least one bone screw assembly that may be used to accomplish the present method. Each citation is hereby incorporated by reference in its entirety.)

Assembly 105 contains a threaded bone screw 107 with threaded shaft 1072 and a spherical head 1074. An internal bore 1076 extends through out the internal aspect of the screw 107—extending from top of head 1074 to the tip of shaft 1072. The internal bore has a threaded portion 1078. A hex-shaped receptacle 1079 resides within head 1074. Receptacle 1079 is adapted to accept a screw driver (such as with a hex-shaped tip, or the like). wherein the driver can deliver a rotational force to screw 107 and drive the threaded shaft into bone.

An outer housing 110 has an internal seat 1102 that is adapt to seat head 1074 of screw 107. Housing 110 has an additional seat 1104 that is adapted to accept an inter-connecting member, such as a rod. Threads 1106 are adapted to compliment and accept threaded locking nut 116. A pusher member 114 rests between the two seat portions 1104 and 1102 of housing 110 and transmits the downward force of the locking nut 116 onto head 1074 (when an interconnecting rod is positioned between the locking nut and pusher member 114).

In use, an interconnecting member, such as a rod, is positioned within seat 1104 of housing 110. The housing 110 and screw 107 are moved into the desired relative spatial orientation. Locking nut 116 is positioned above the seated interconnecting member and then threadedly advanced relative to threads 1106 of housing 110. As locking nut 116 is advanced, the interconnecting rod member is forced onto pusher member 114. The pusher 116 is forced downward onto head 1074 of screw 1074 and trapping the head between the pusher 116 and seat 1102. In this way, full advancement of locking nut 116 produces rigid immobilization of the interconnecting member, the housing 110 and the screw 107 relative to one another. (It should be appreciated that screw assembly 105 is an example of bone screw assembly that may be used. It is understood that other bone screw assemblies may be alternatively used. Multiple such screw assemblies are known in the art. For example, U.S. RE37665, U.S. Pat. No. 6,248,105, U.S. Pat. No. 6,371,957, U.S. Pat. No. 6,565,565, U.S. Pat. No. 6,641,586, U.S. Pat. No. 7,704,271 all disclose at least one bone screw assembly that may be used to accomplish the present method. Each citation is hereby incorporated by reference in its entirety.)

Figure 5:
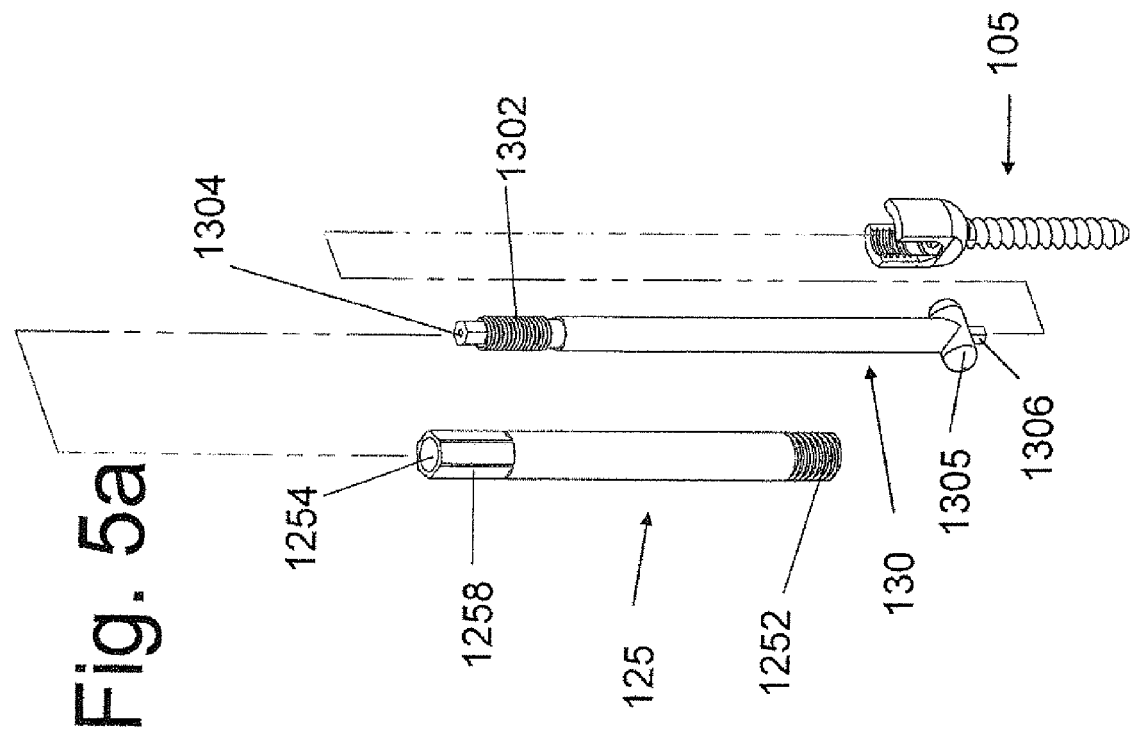
FIGS. 5A-B show representative bone screw assembly and coupling devices.

As shown in FIG. 5, the assembly 105 can be coupled to coupler member 125 and 130. FIG. 5*a* shows the devices in an exploded state while FIG. 5*b* illustrates the assembled state. Outer member 125 has threaded end 1252 that is adapted to threadedly engage threads 1106 of housing 110. Member 125 has an elongated body with a central bore 1254 that extends there through from the top to the bottom surface of member 125. Central bore 1254 is adapted to accept member 130 within. At the top aspect of member 125, a hex-shaped segment 1258 is present. The segment 1258 is adapted to accept a hex-shaped driver (driver not shown) on the outer aspect of the member 125, wherein the driver, when engaged, is adapted to apply a rotational force to member 125.

Internal member 130 has an elongated body with a threaded segment 1302. Internal member 130 has a central bore 1304 that extends there through from the top to the bottom surface of member 130. A "T" shaped protrusion 1305 has a hex-shaped protrusion 1306 beneath it, wherein hex-shaped protrusion 1306 is adapted to snuggly rest within hex-shaped cut out 1079 of screw 107 such that rotation of member 130 produces rotation of screw 107. Further T shaped protrusion 1305 is adapted to rest within seat 1104 of housing 110. An additional hex-shaped protrusion 1308 is located at the top of member 130

Figure 8:
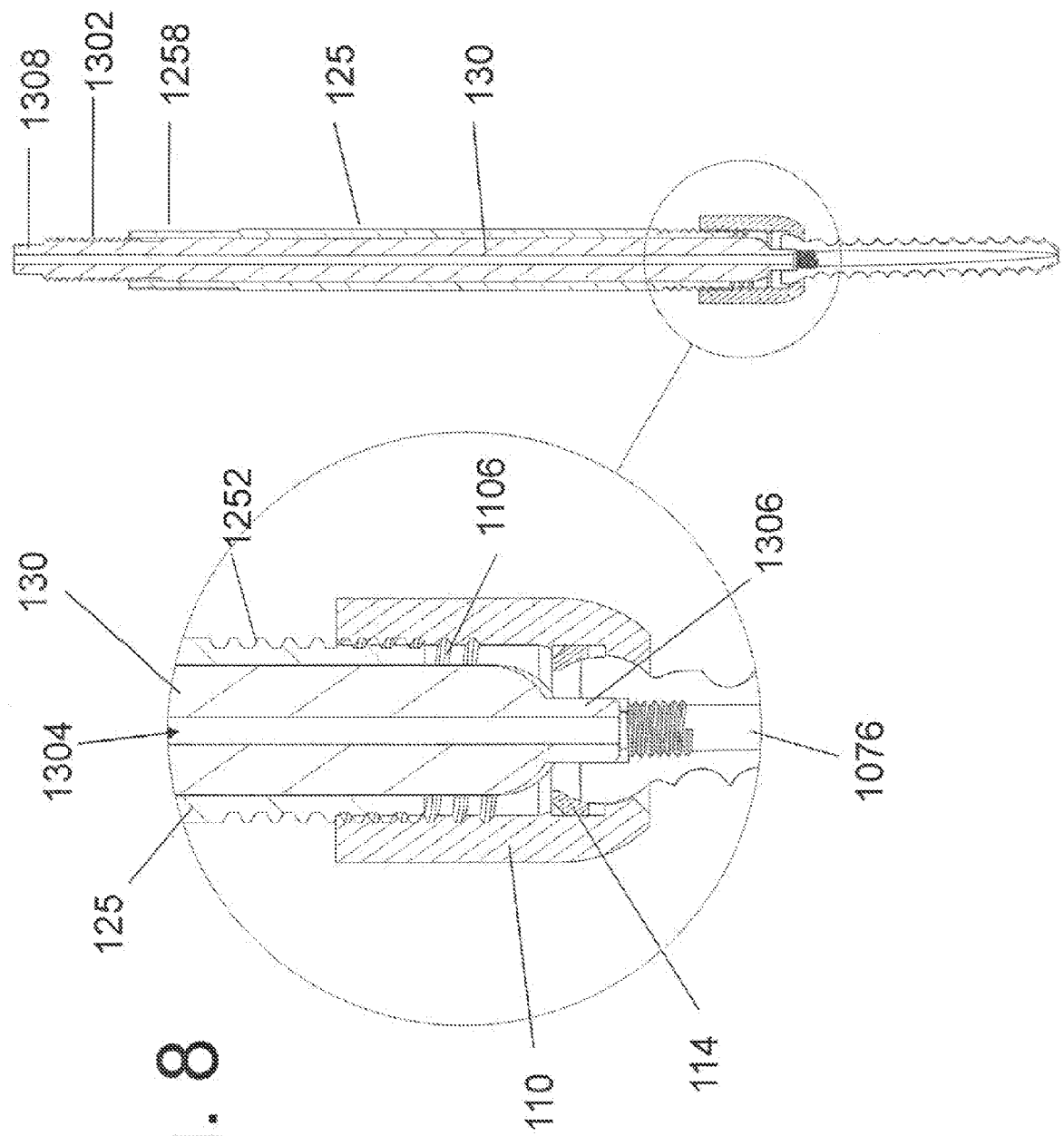
FIGS. 8 and 9 show section views through the device assembly of FIG. 5B.
Figure 9:
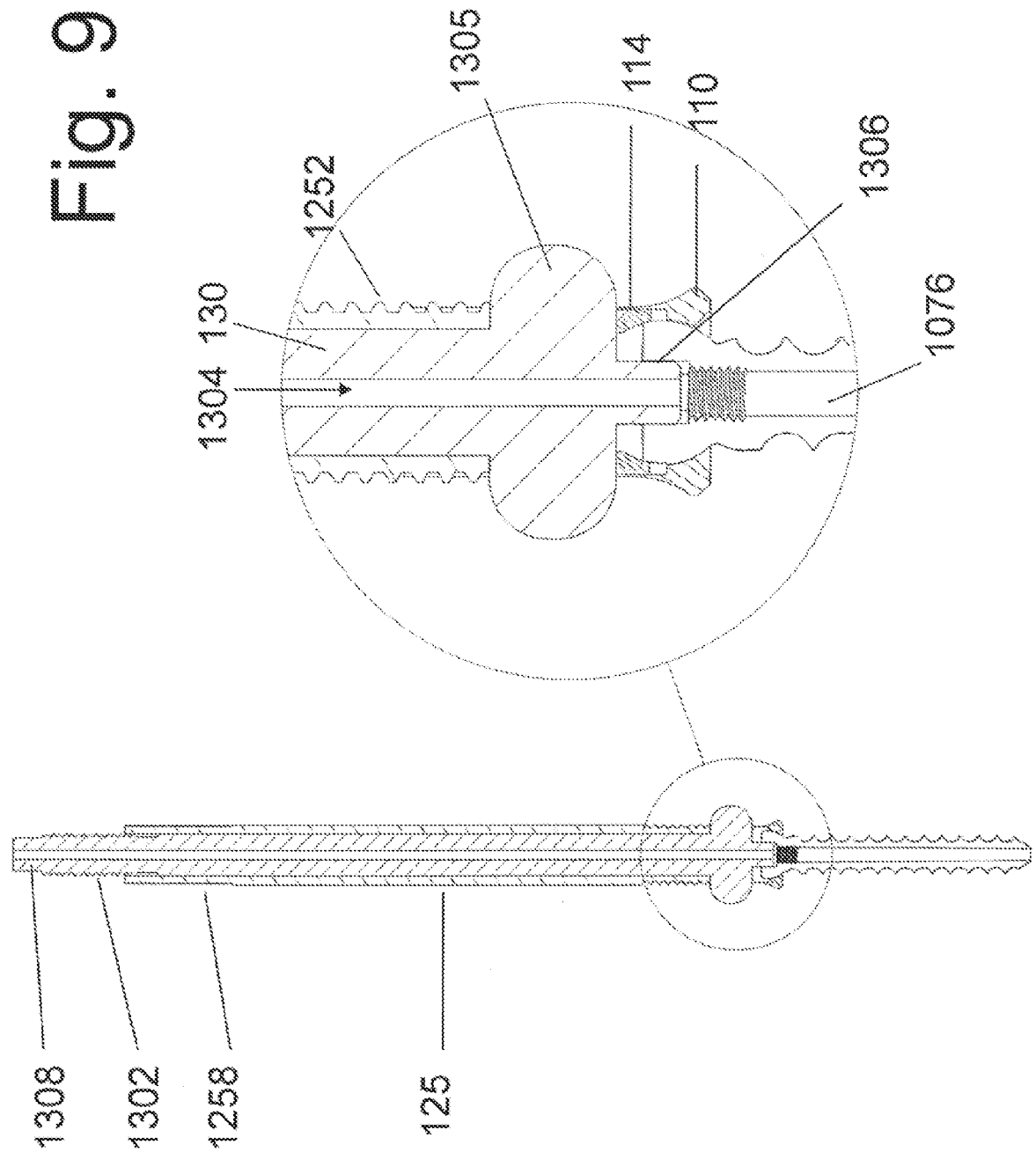

FIGS. 8 and 9 show section views through the device assembly of FIG. 5*b*. FIG. 8 shows a section view that is perpendicular to the "T" shaped protrusion 1305 of member 130. FIG. 9 illustrates a section view that is parallel to the "T" shaped protrusion 1305 of member 130. In FIGS. 8 and 9, member 130 is shown within bore 1254 of member 125. Protrusion 1306 rests within cut-out 1079, and aligns the long axis of screw 107 with that of housing 110, member 130 and member 125. Threads 1252 are driven into complimentary threads 1106 of housing 110 so that member 125 is threadedly locked to housing 110. In this way, member 110,107,130 and 125 are aligned and rigidly coupled to one another. Further, the application of a rotational force to hex-shaped protrusion 1308 (atop member 130), such as with a hex driver, caused rotation of the complete assembly and permits the advancement of threaded screw 107 into bone, Note that in the rigid assembly of FIG. 5*b*, bore 1304 of member 130 is aligned with bore 1076 of screw 107, thereby permitting passage of a guide needle from one end of the assembly through each of bore 1304 and bore 1076 and out the other end of the assembly.

Figure 10:
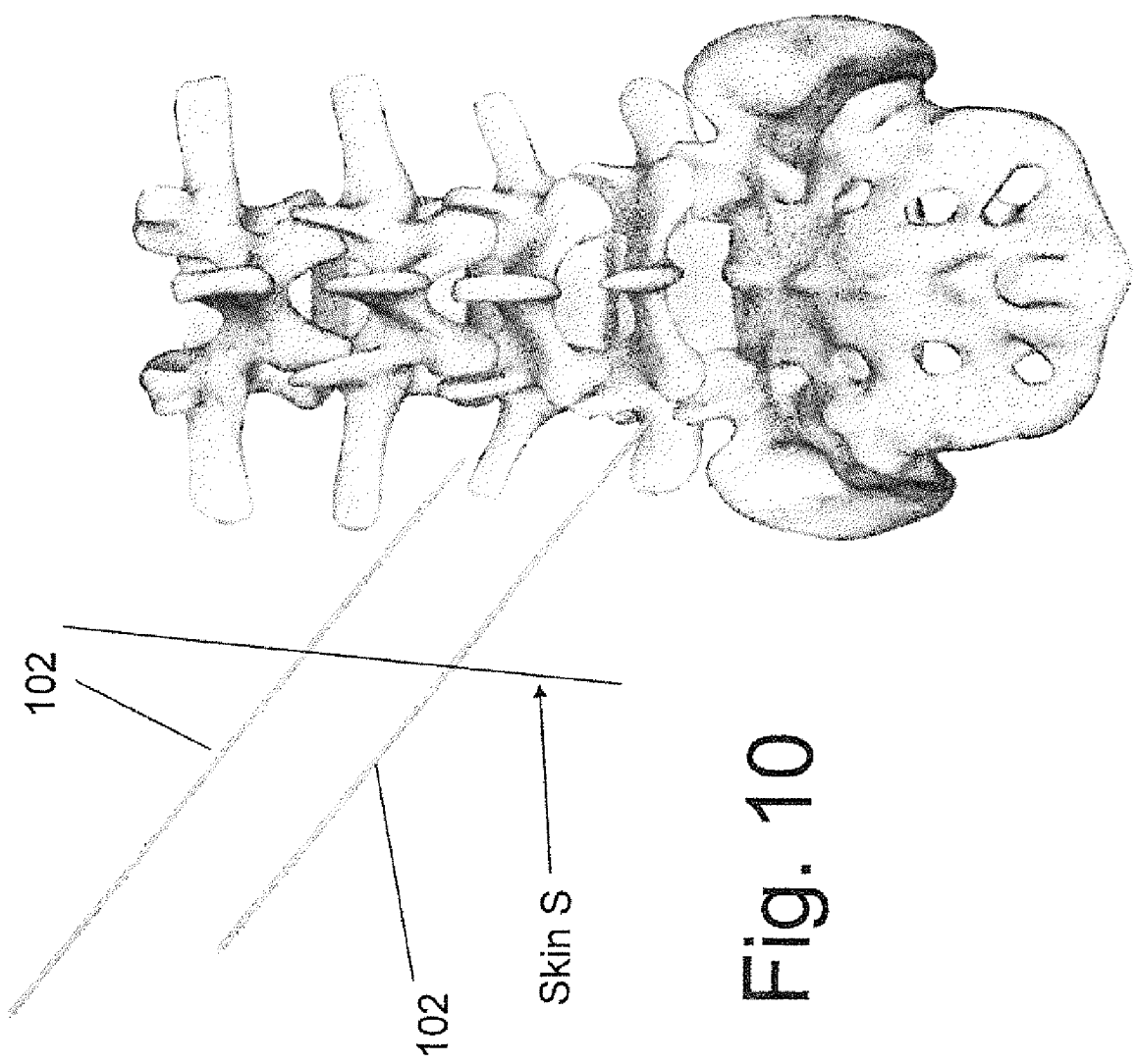
FIG. 10 shows schematically at least one wire advanced partially into the underlying pedicle of at least one vertebral bone.

An embodiment of the method of device use is now disclosed, The method illustration assumes that the L4 and L5 bones are to be fused and the L4/5 disc space is the target for implant placement. However, it is understood that the method may be alternatively used at any applicable spinal level. Under imaging guidance (X-ray, CT, MRI and the like), each of two guide wires 102 (substantially similar to elongated needles) is percutaneously passed through the skin (at or about skin region $X_1$ and $X_2$), and advanced to indentation 811 of each of the L4 and L5 vertebral bones. Each wire 102 preferably contains a threaded distal end with a sharpened tip. At least one wire 102 is then advanced (or threaded) at least partially into the underlying pedicle of at least one vertebral bone. This is schematically shown in FIG. 10 wherein the skin is schematically shown and labeled skin S. Those skilled in the art will appreciate that actual vertebral bodies may include anatomical details that are not shown in FIG. 10.

The skin entry site of and underlying soft tissue surrounding each wire is enlarged in preparation for bone screw placement. This can be performed using any applicable method but. in the preferred embodiment, serial cylindrical tubes of enlarging diameter are sequentially passed over the guide wire 102. This method of sequential tube dilatation of tissues over a guide wire is well known to those of ordinary skill in the art and will not be further detailed or illustrated. An assembly of bone fastener 105 and couplers 125/130 are assembled as shown in FIG. 5b and then advanced over a guide wire 102, wherein guide wire 102 extends through bores 1304 and 1076 of the assembly. The assembly is advanced until the threaded shank of screw 107 engages the vertebral bone at or about indentation 811. With rotation of protrusion 1308 (driver not shown) the bone screw is threadedly advanced into the pedicle portion of each vertebral bone. Preferably, the bone screw is advanced into the pedicle under radiographic visualization.

In actual use, a hole in the bone may need to be pre-formed with a tap instrument prior to screw placement. Further, the advancement of instruments (such as a tap or the bone screw) is preferably performed with the screw electrically connected to an electromyography (EMG) machine to minimize the possibility of nerve injury. (The technique is known in the art and is described in 1) *Intraoperative electromyography during thoracolumbar spinal surgery*. By Holland, NR. Spine 1998 Sep. 1: 23(17): 1915-22. and 2) *Improving accuracy and reducing radiation exposure in minimally invasive lumbar interbody fusion*. By Wood M J, Mannion R. T. J Neurosurg Spine. 2010 May; 12(5): 533-9. Each article is hereby incorporated by reference in its entirety.)

Figure 11:
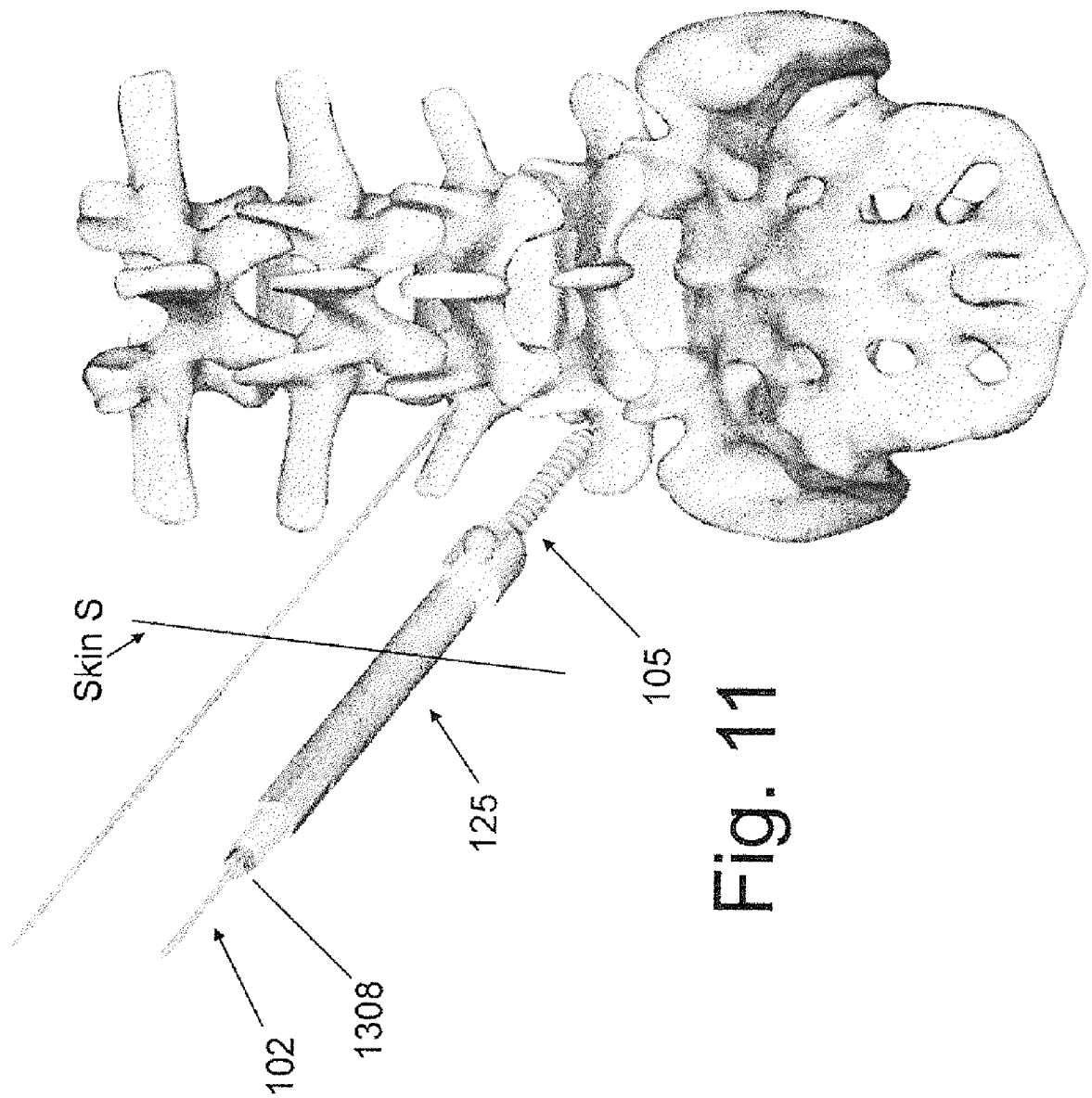
FIG. 11 shows a step in the advancement of fastener into the bone.
Figure 12:
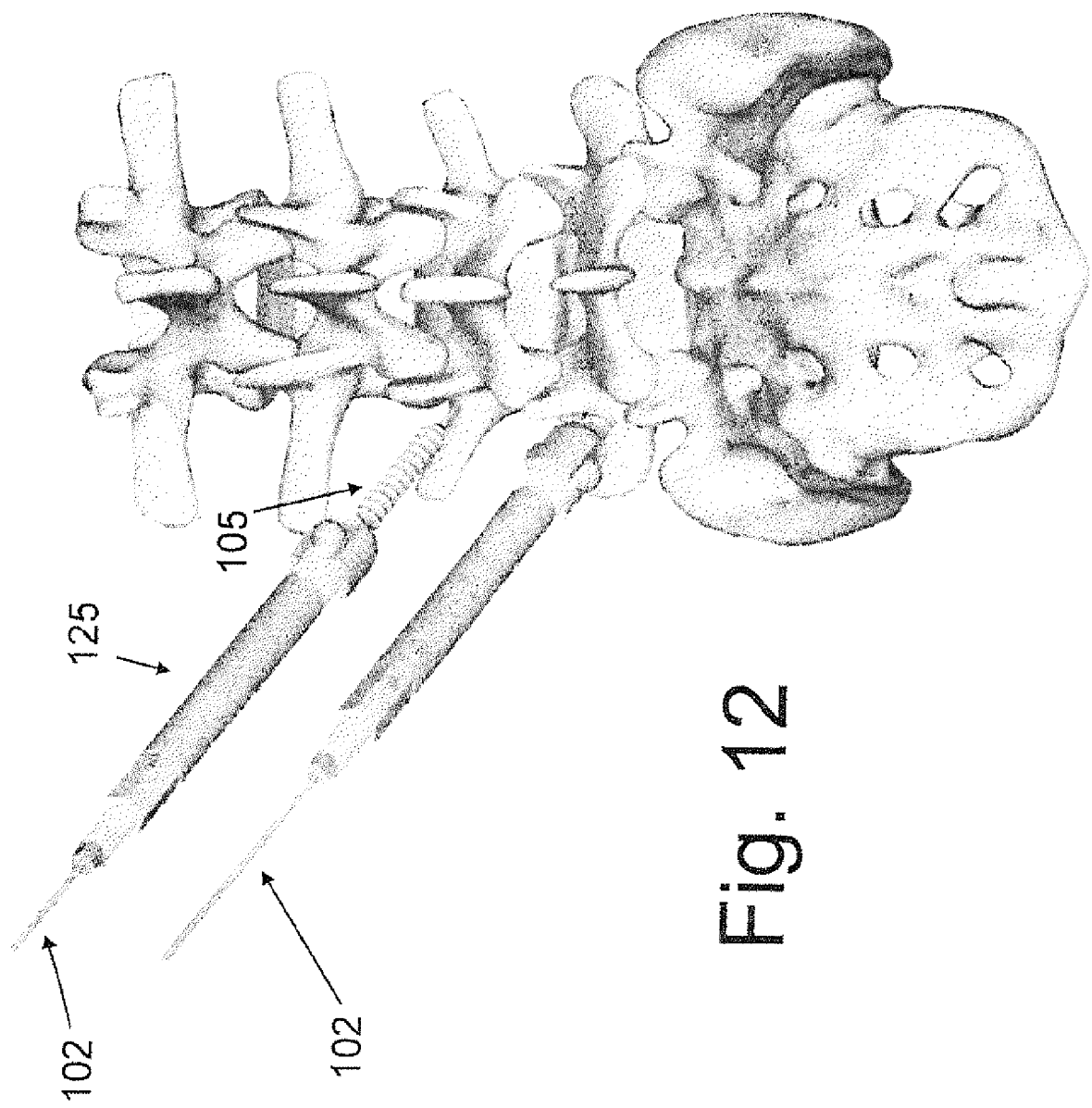
FIG. 12 shows a step in the advancement of fastener into the bone.
Figure 13:
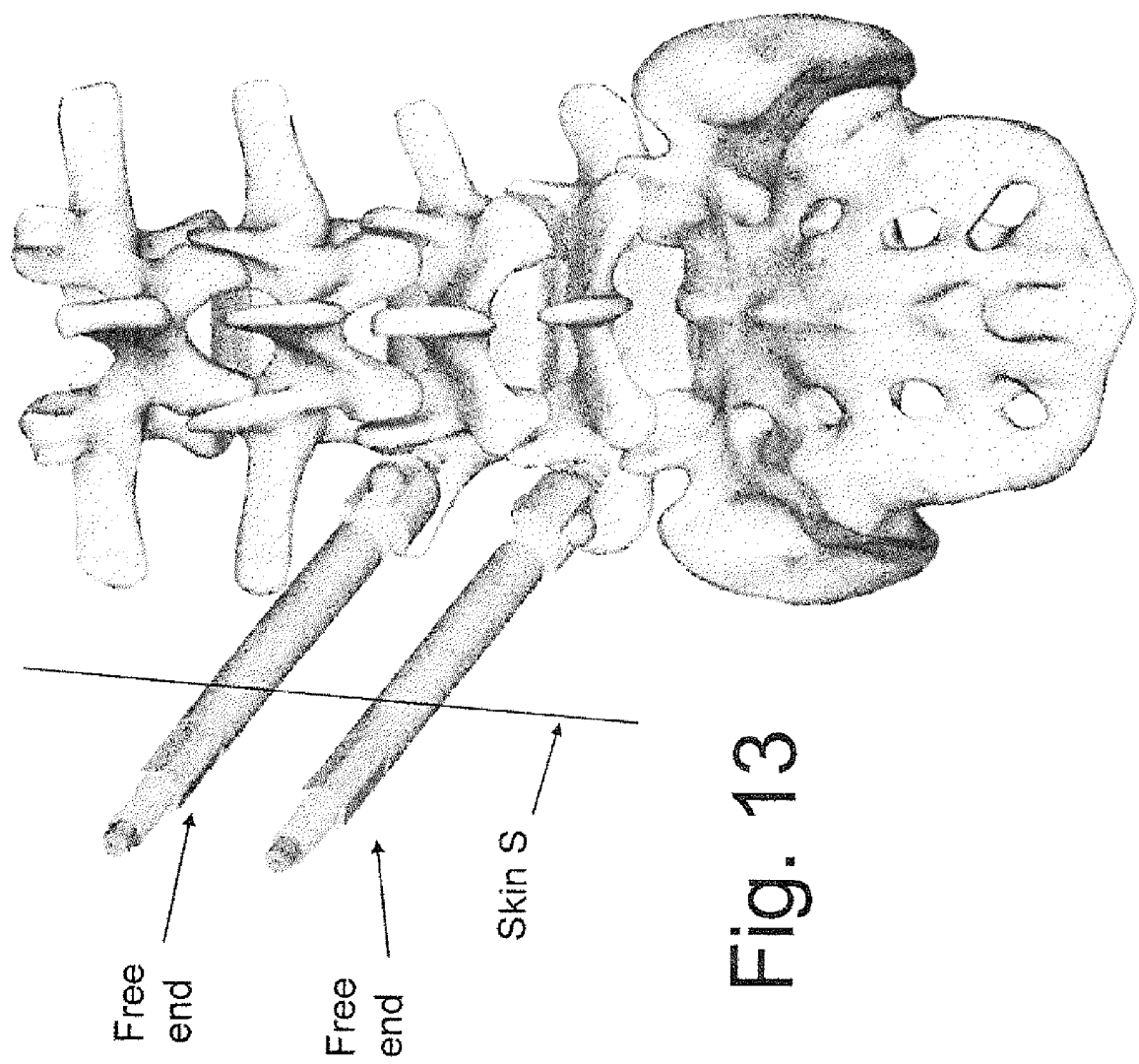
FIG. 13 shows a step in the advancement of fastener into the bone.

The sequence is shown in FIGS. 11 and 12. After the fasteners are fully advanced into the bone, the guide wires 102 are removed—leaving the implanted fasteners and couplers as shown in FIG. 13. (An alternative method is further contemplated wherein a guide wire is not employed to guide the bone screw assembly. In this embodiment, a larger diameter tube is forcibly advanced through the skin and the soft tissue until indentation 811 of a targeted vertebral bone is reached. A cannula is removed from within an internal bore of the tube and bone screw assembly is advanced to indentation 811 through the internal bore of the tube.)

Note that the free end of each coupler 125/130 extends beyond the skin S so that free end of each coupler is physically located outside of the patient's body. Each coupler penetrates the skin S at a small incision (preferably a small "stab" wound) that surrounds the coupler. The segment of skin between each of the skin penetration sites of each coupler can be connected with a scalpel or other cutting instrument, so that a single skin incision starts immediately inferior to the inferior coupler, extends between the couplers and ends immediately superior to the superior coupler. If desired, the step of connecting the skin incision sites so as to form one larger incision may be performed earlier in the implantation procedure (such as, for example, at the start of the procedure, wherein one larger incision is placed instead of two smaller ones. Alternatively, two small stab wounds may be used to advance the guide wired 102 onto the bone. The incision may be then enlarged after guide wire placement.)

The skin incision segment between the couplers is then extended anteriorly from the level of the posterior skin incision, through the soft tissues that are posterior to (i.e., in back of) the spinal column until the posterior aspect of the vertebral bones are reached. That is, a corridor is developed between the couplers from the skin surface to the posterior aspect of the vertebral bone, wherein, in a preferred embodiment, the corridor developed is similar to that of Corridor K, which is schematically shown in FIG. 4.

Figure 16:
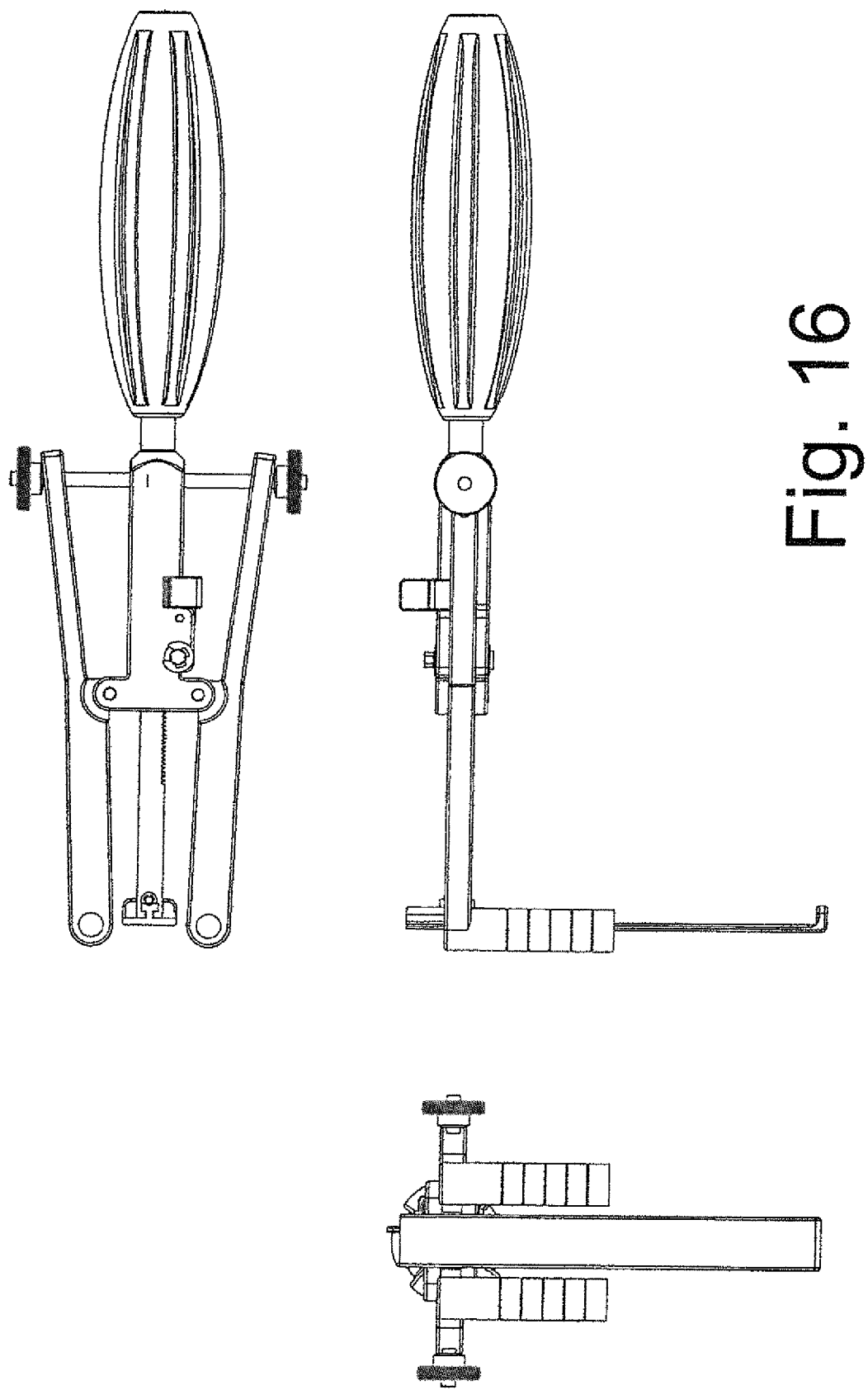
FIG. 16 show various view of the platform.
Figure 17:
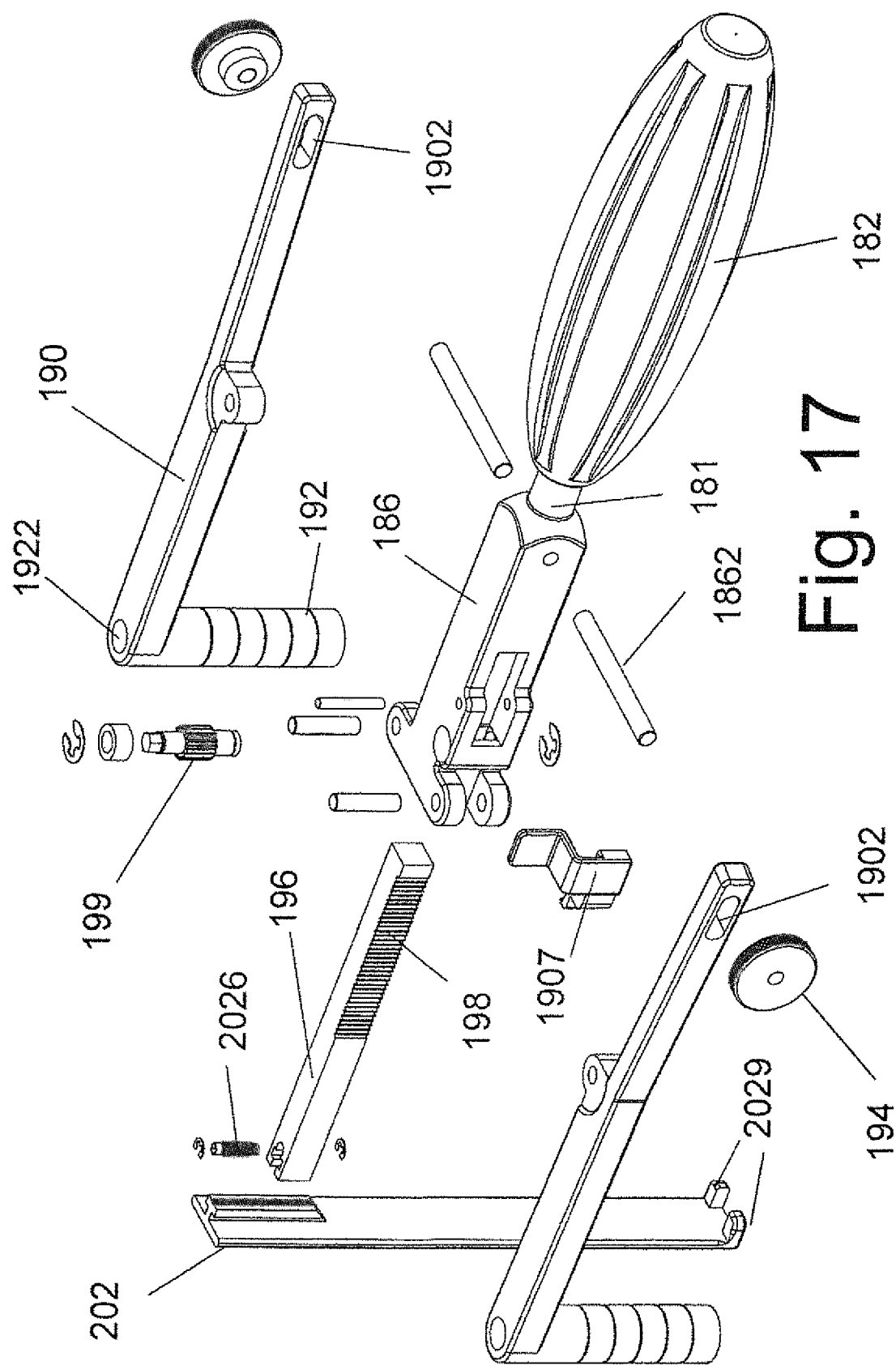
FIG. 17 shows an exploded view of the platform.
Figure 18:
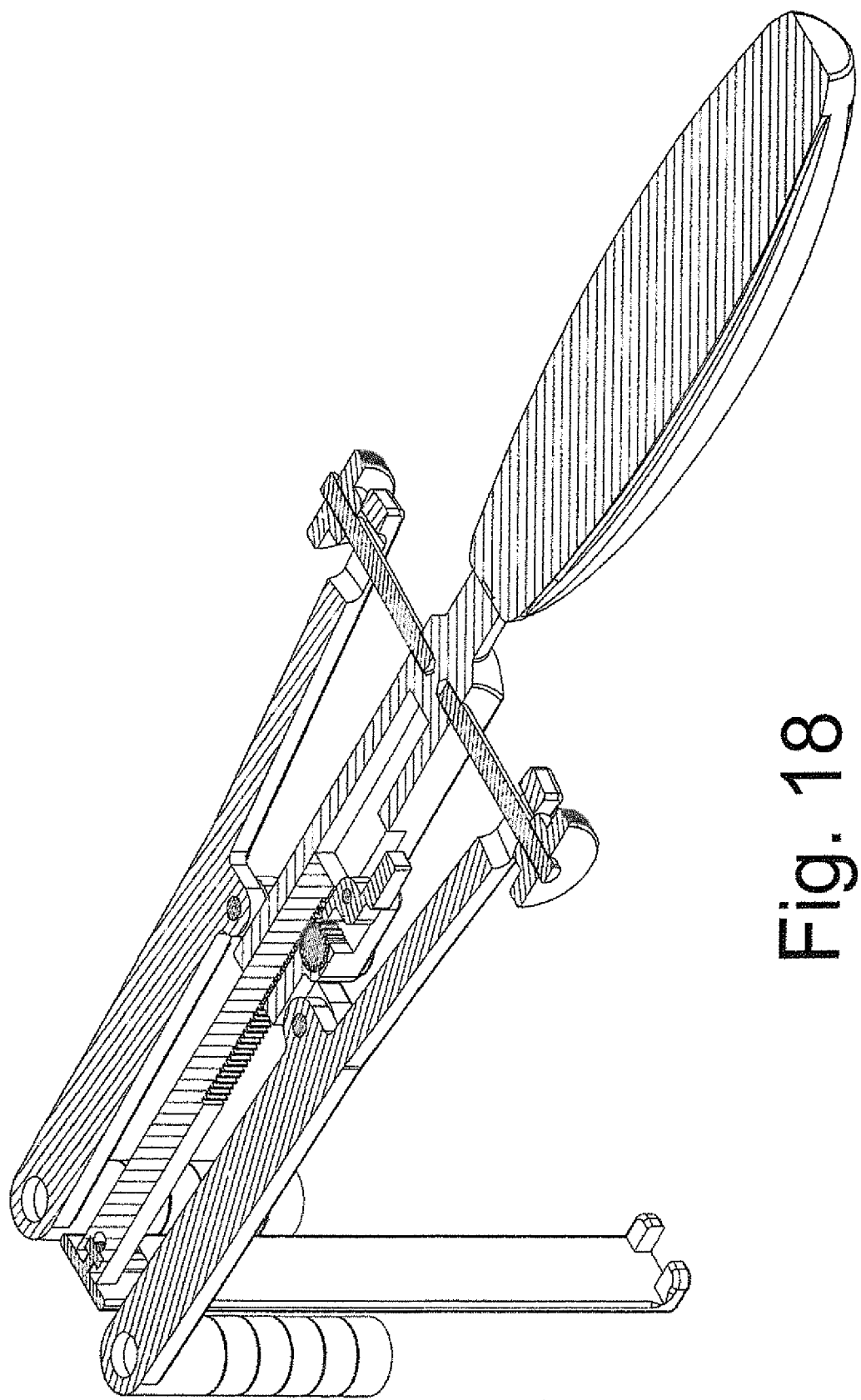
FIGS. 18 and 19 show cross section views of the platform.
Figure 19:
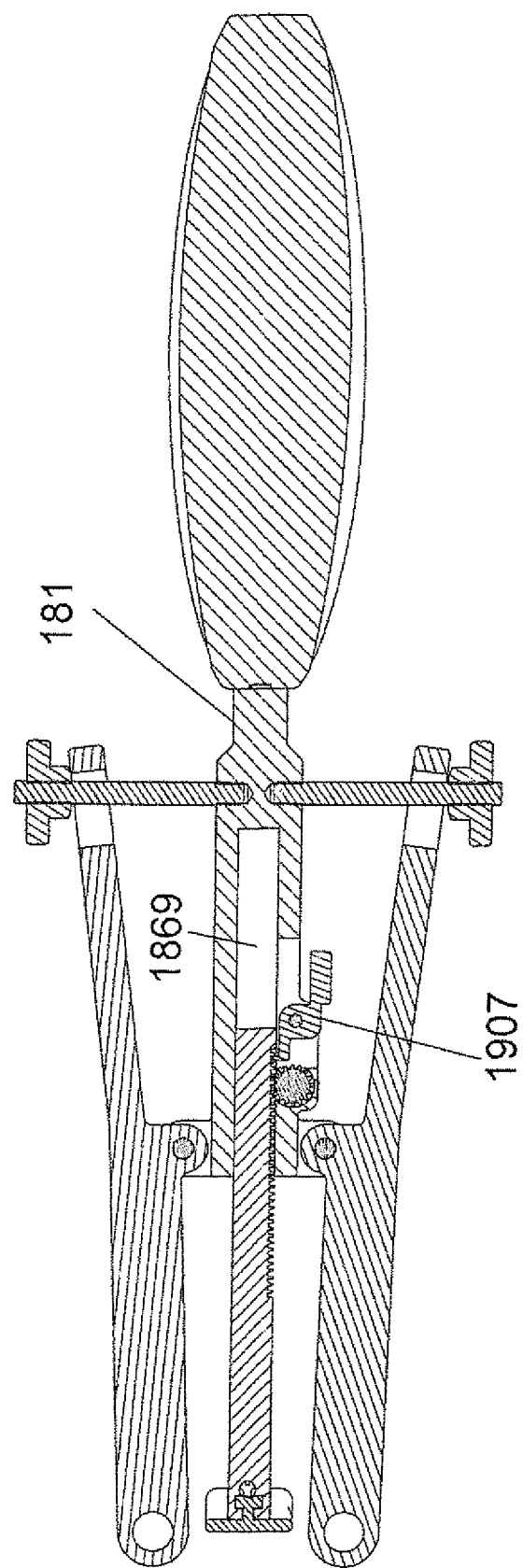

A distraction platform 180 is then attached onto each of the couplers 125/130 (each coupler being attached to a screw assembly 105), wherein the distraction platform is preferably, but not necessarily, adapted to distract the couplers towards or away from one another. An embodiment of a distraction platform is shown positioned in FIG. 14. Distraction platform 180 is an example of a platform that may be used and those of ordinary skill in the art will appreciate that any appropriate distraction platform may be alternatively used in the illustrated method. (An example of a distractor platform is disclosed in U.S. Pat. No. 7,819,801. The text is included by reference in its entirety). In the preferred embodiment, the distractor has members adapted to interact with the coupler 125/130 and at least one additional member adapted to retract soft tissues (such as muscle, fat and the like) away from the screw 105/coupler 125/130 assemblies. A perspective view of the platform is shown in FIG. 15 A and multiple orthogonal views are shown in FIG. 16. An exploded view is shown in FIG. 17 and section views are shown in FIGS. 18 and 19.

The distraction platform 180 has handle 182 and central body member 186 that are interconnected by cylindrical region 181. Each of distraction arms 190 have an elongated member 192 that contains internal bore 1922, wherein bore 1922 extends the full length of the member 192. In a preferred embodiment, the internal bore 1922 of elongated member has a proximal (upper) opening 19226 and distal (lower) opening 19224, wherein the proximal opening is smaller than the distal opening. A section view through elongated members 192 is shown in FIG. 15B. Preferably, the external surface of elongated member 192 has markings that are labeled with numbers, letters, or other designation. In use, bore 1922 contains the proximal segment of coupler 125/130, wherein a segment of 1302 of member 130 emerges from the proximal (upper) opening 19226 of bore 1922. The smaller bore of opening 19226 permits segment 1302 of member 130 to exit bore 1922 but segment 1258 of member 125 is retained within member 192 (see FIG. 15C). A locking nut 1107 can be used to engage the threaded portion of segment 1302 that rests outside of member 192 and to lock the assembly of members 105, 125 and 130 relative to member 192 of distraction platform 180. When platform 180 engages couplers 125/130 and screw assembly 105, the skin rests at or between markings of the external surface of elongated member 192. In this way, the distance from skin to the bone fastener 105 can be easily read directly off of the external markings of member 192.

Distraction arm 190 articulates with body 186. Arm 190 has slot 1902 that is adapted to accept threaded post 1862 (threads not shown). Thumb wheel 194 has internal threads that threadedly interacted with threaded post 1862 and produce a compressive force onto the end of arm 190 that contains slot 1902. With advancement of wheel 194, the segment of distraction arm 190 that contains slot 1902 is urged towards body 186, and the segment of distraction arm 190 that contains member 192 is rotated outwardly and away from body 186. After platform 180 is attached to couplers 125/130 and screw assembly 105, thumb wheel(s) 194 may be actuated to impose a distractive force onto one or the other of the vertebral bones (or both). In this way, the vertebral bones may be moved away from one another in the vertical plane. Bony distraction may be performed before or after facet resection (or not at all). In a preferred embodiment, no distraction is performed prior to facet resection. In another preferred embodiment, distraction is performed prior to facet resection.

Arm 196 has side serrations 198. An end of arm 196 rests within bore 1869 of body 186. A spring-loaded (spring not shown) pawl 1907 and member 199 interact with serrations 198 of arm and serve as a mechanism to move arm into and out of bore 1869 of body 186. A removable tissue retractor 202 rests at the distal end of arm 196. Arm 202 has at least one distal extension 2029 that interact with the retracted tissue.

Figure 20:
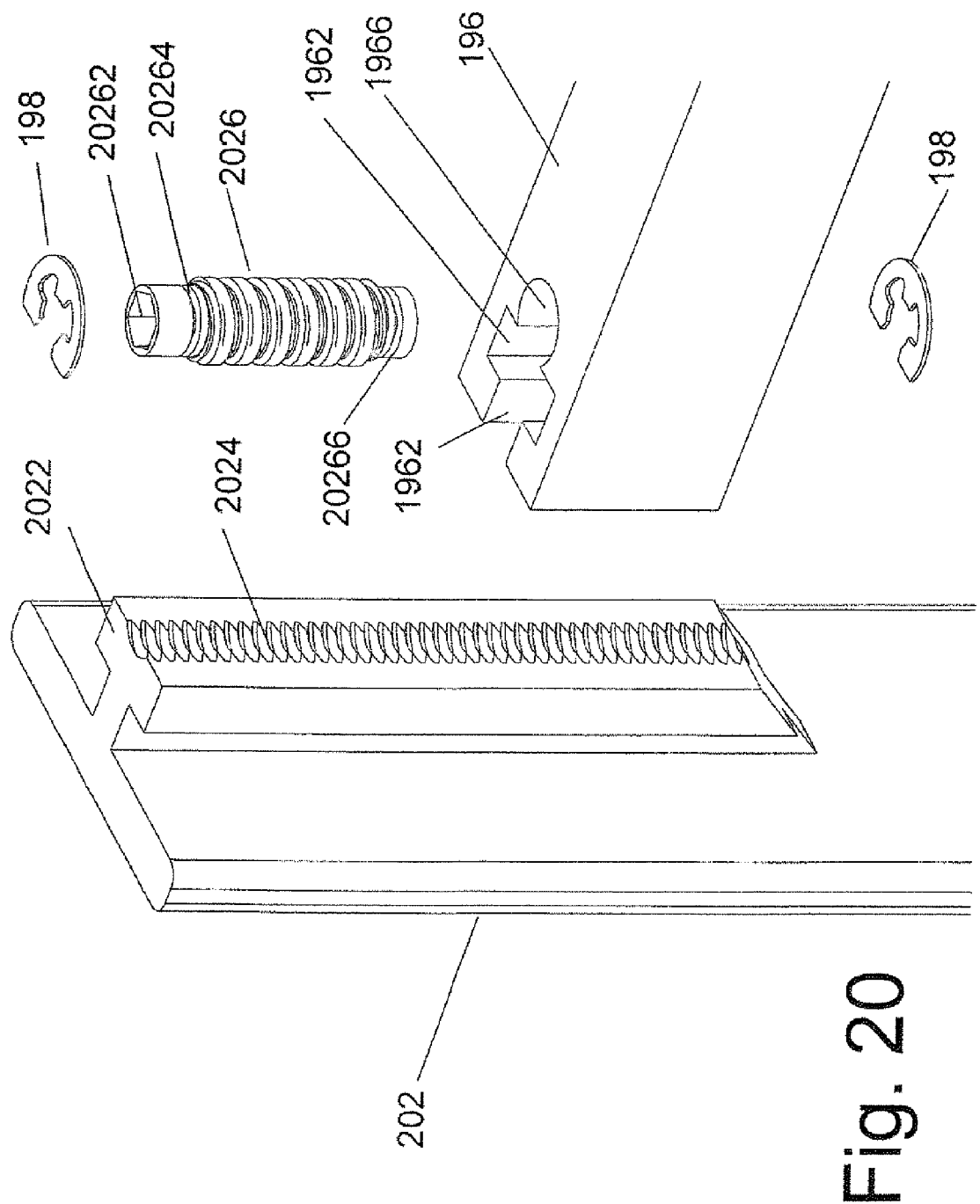
FIGS. 20-22 show close-up views of the proximal end of removable tissue distraction arm.
Figure 21:
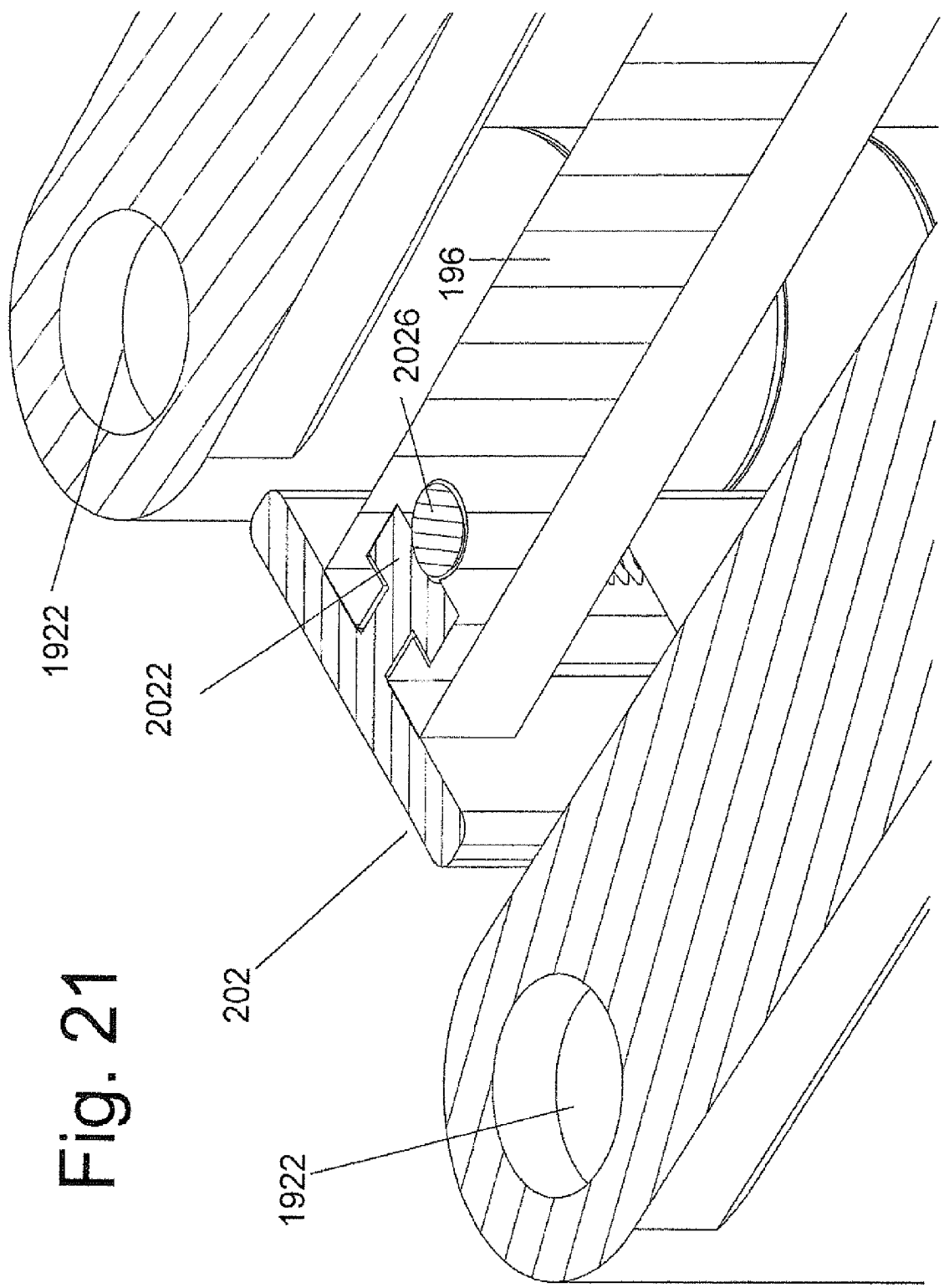
Figure 22:
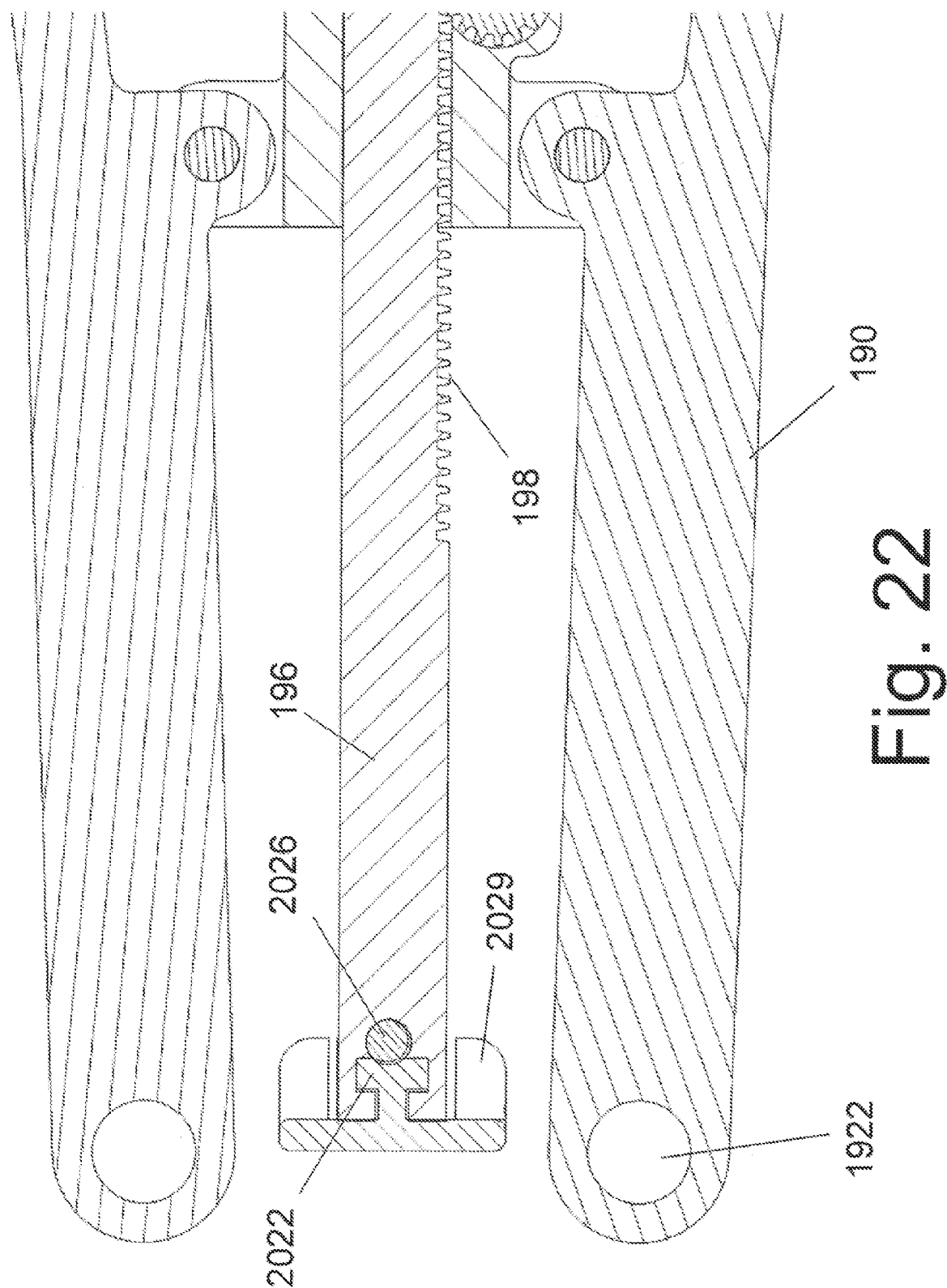

A close-up view of the proximal end of removable tissue distraction arm is shown in FIG. 20. Tissue distraction arm 202 has a protrusion 2022 with surface 2024 that contains partial threads (adapted to interact with threads of screw 2026). Protrusion 2022 rests within cut-out 1962 of arm 196. A threaded screw 2026 resides within bore 1966 of arm 196. A clip member 198 is adapted to rest within each of an upper channel 20264 and lower channel 20266 that rest on each side of the threads of screw 2026. The clip members 198 function to retain threaded screw 2026 within bore 1966. Screw 2026 has a hex-shaped cut out 20262 that is adapted to accept a complementary hex-drive screw driver.

As noted, distraction arm 202 is preferably removable in that the arm can be removed from cut-out 1962 of arm 196 by the surgeon at the time of surgery. Rotation of screw 2026 (through the action of a hex-drive positioned within cutout 20262) within bore 1966 will necessarily produce the interaction and movement of the threads of screw 2026 and the threads of surface 2024 of arm 202. Rotation of screw 2026 in a first direction will cause upward movement of arm 202, whereas rotation of screw 2026 in the opposite direction will produce downward movement of arm 202. With continued rotation of screw 2026 in one direction, the surgeon can produce sufficient movement of arm 202 such that protrusion 2022 exits cut-out 1962 of arm 196 and distraction arm 202 detaches from distraction platform 180. In this way, arm 202 is reversibly detachable (and mountable) relative to platform 180.

In the preferred embodiment, screw 2026 can be used to adjust the distance from arm 196 to protrusions 2029 of distraction arm 202. This is an important and notable feature of the preferred distraction platform. That is, in the preferred embodiment, distraction arm 202 is reversibly removable from distraction platform 180 and, when attached to the platform, the vertical distance from a horizontal surface of member 196 of platform 180 to the distal end (protrusions 2029) of arm 202 that engage the soft tissues may be varied by the operating surgeon. (While the variation in distance from platform 180 to protrusions 2029 of arm 202 may be accomplished by the movement of an end of a fixed length arm 202 relative to the platform, as illustrated, it may be alternatively accomplished my attachment of a variable length distraction arm 202 which is stationary relative to the platform 180 at the point of mutual attachment.).

Distraction arm 202 functions to retract muscle segment M1 (FIG. 4) medially towards spinous process SP and uncover the posterior aspect of the facet joint to be resected. After muscle retraction by arm 202, corridor K is expanded medially from that shown in Figure to approximately that represented by the schematic drawing of FIG. 25B. In the preferred embodiment, the distraction platform 180 is coupled to the coupler 125/130 and bone screw as shown in FIG. 14.

The surgeon may elect to use locking nuts 1107 to rigidly lock one or more of the couplers 125/130 to platform 180. In addition, the platform 180 may be further immobilized relative to the spine and the patient by applying an articulated frame, wherein the frame is adapted to rigidly couple to platform 180 on a first end and to rigidly attach to the operating table at a second end. The frame further contains multiple segments that are adapted to reversibly transition from a first state, wherein there are relative movements between the segments, to a second state, wherein the segments are rigidly affixed to each other. Finally, the surgeon may elect not to lock the frame to the couplers or to the operating table.

Frame devices that anchor surgical retractors to the operating table are well known in the art. In the illustrated device (FIG. 25D), articulated frame 905 has member 9052 that reversibly attaches to the operating table onto which the patient is positioned. Member 9056 is adapted to reversibly and rigidly clamp onto a segment of platform 180. An end of member 9056 is adapted to clamp onto, for example, cylindrical segment 181 of platform 180, wherein locking member 9058 locks end segment 9056 after the latter is positioned onto segment 181. Member 9054 is adapted to reversibly transition the frame 905 from the first state (movably articulating frame segments) to the second state (articulated frame segments are rigidly locked to one another). While an example of an articulated frame 905 is illustrated, it is understood that any other applicable such device may be alternatively used. (For example, U.S. Pat. No. 4,254,763, U.S. Pat. No. 5,908,382, U.S. Pat. No. 6,302,843, U.S. Pat. No. 6,709,389, U.S. Pat. No. 7,156,806 and many other are known to disclose surgical retractor systems that anchor to the operating table. Each citation is hereby incorporated by reference in its entirety.)

In use, the distal tip of the tissue distraction must rest immediately posterior to the facet joint that will be resected. In selection of the proper distraction arm 202 to attach to the platform 180, the surgeon will need to know the distance from the skin edge of the incision to the posterior aspect of the facet joint. This distance can be measured directly with a ruler. Alternatively, the distance from the skin edge to the top of screw assembly 105 can be read directly off of the external surface markings of elongated member 192. In most patients, the distance form the skin edge to the posterior aspect of the facet joint is close to the distance from skin edge to the top of screw assembly 105 (of the inferior vertebral bone). The distance between the skin edge to the top of screw assembly 105 can be used a convenient approximation to the distance from skin to the posterior aspect of the facet joint. Since distraction arm 202 is movable relative to arm 196, any difference between the distance from skin edge to the top of screw assembly 105 and the distance from the skin edge to the posterior aspect of the facet joint can be easily corrected by the movement of distraction arm 202 relative to member 196 after attachment. However, if a distraction platform is used wherein the distraction arm is stationary relative to the attachment region of the platform, then the distance from skin to the posterior aspect of the facet joint is preferably measured directly with a ruler.

Figure 23:
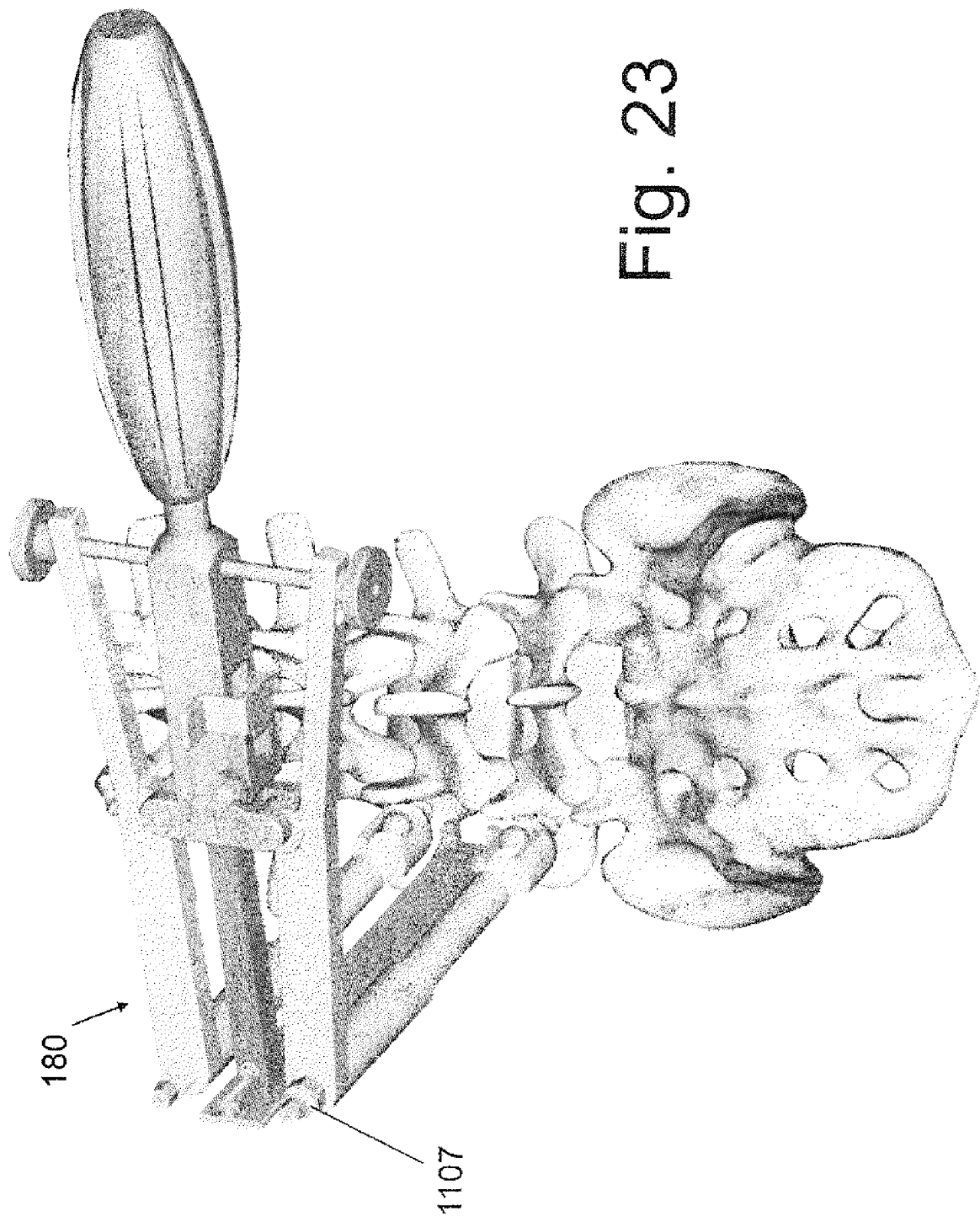

With the appropriate length tissue distraction arm 202 selected and positioned within the incision between each of the fastener coupler members—as shown in FIG. 23, a lateral X-ray is obtained. The distal end of the tissue distraction atm 202 is moved anterior/posteriorly by rotating screw 2026 until the distal end of arm 202 rests immediately in back of (i.e., posterior to) the facet joint 814 as shown in FIG. 24. The tissue distraction atm is moved medially by the rotation of member 199 and arm 202 retracts muscle segment M1 towards the spinous processes SP of the superior and inferior vertebral bones (FIG. 25A). In this way, a working corridor WC is formed between each of the coupler engagement members and tissue distraction arm of the distraction platform, wherein the posterior surface of the facet joint 814 is exposed and accessible within working corridor WC.

Figure 25C:
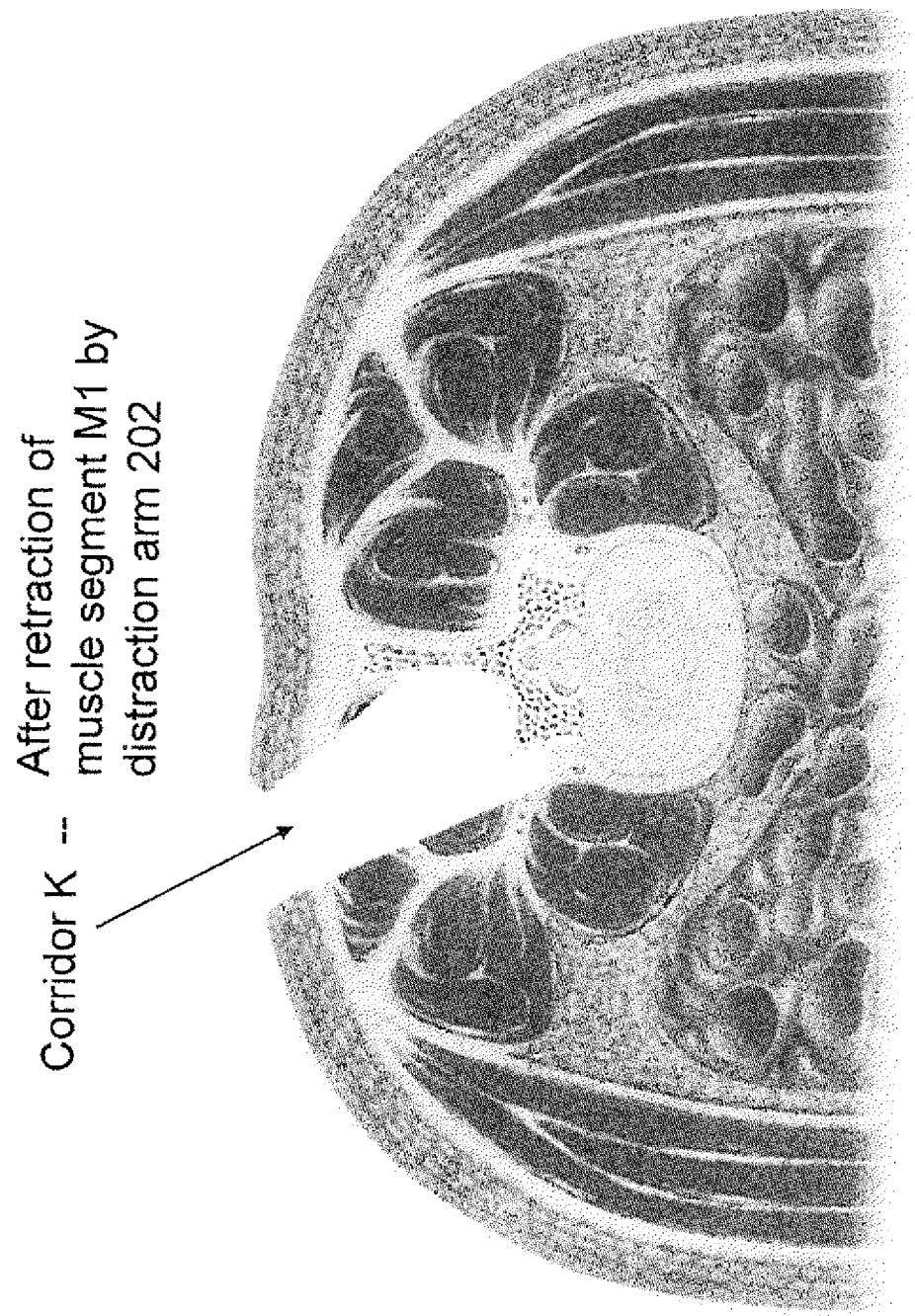

The working corridor is seen in a different perspective in FIG. 25B. Note that the distraction arm 202 rests in proximity to the spinous process and permits access, through the working channel, to the facet joint as well as the lamina portion of the vertebral bones. FIG. 25C illustrates an approximation of the soft tissue corridor K (first shown in FIG. 4) after placement of the distraction platform the medical retraction of distraction arm 202. (Note that corridor K is approximately equivalent to the working corridor WC. For clarity of illustration, the contents of the torso in FIG. 25C are represented schematically and those skilled in the art will appreciate that an actual cross section of the human torso may include anatomical details not shown in the illustration.)

After exposure of the facet joint, bone removing instruments are used to cut at least a segment of facet joint 814 and reveal the posterior aspect of the disc space that is immediately anterior to it. Preferably, the removed portion of the facet joint would include the lateral surface of the facet joint. The exposed portion of the disc space includes the segment of the posterior disc surface that rests immediately anterior to the neural foramen of the nerve root that exits the spinal canal beneath the pedicle portion of the superior vertebral bone. That is, at least a portion of the exposed posterior disc surface rests, in the superior/inferior plane, between the inferior aspect of the nerve root that exits the spinal canal beneath the pedicle of the superior vertebral bone and the superior aspect of the pedicle of the inferior vertebral bone of the targeted FSU. The exposed portion of the disc space is bordered medially by the lateral aspect of the nerve root that exits the spinal canal beneath the pedicle of the inferior vertebral bone of the targeted FSU.

While any instrument that is adapted to remove a portion of the facet joint may be used, the removal is preferably made with one or more instruments that collectively drill away a portion of the bone and rongeur away other joint fragments. In an embodiment, an instrument that is adapted to perform both the drill and rongeur function is shown in FIGS. 26 to 30. It is understood that the illustrated instrument is not restrictive in any way and any other instrument or combination of instruments that may remove bone by drilling and cutting the joint may be alternatively used.

Figure 26:
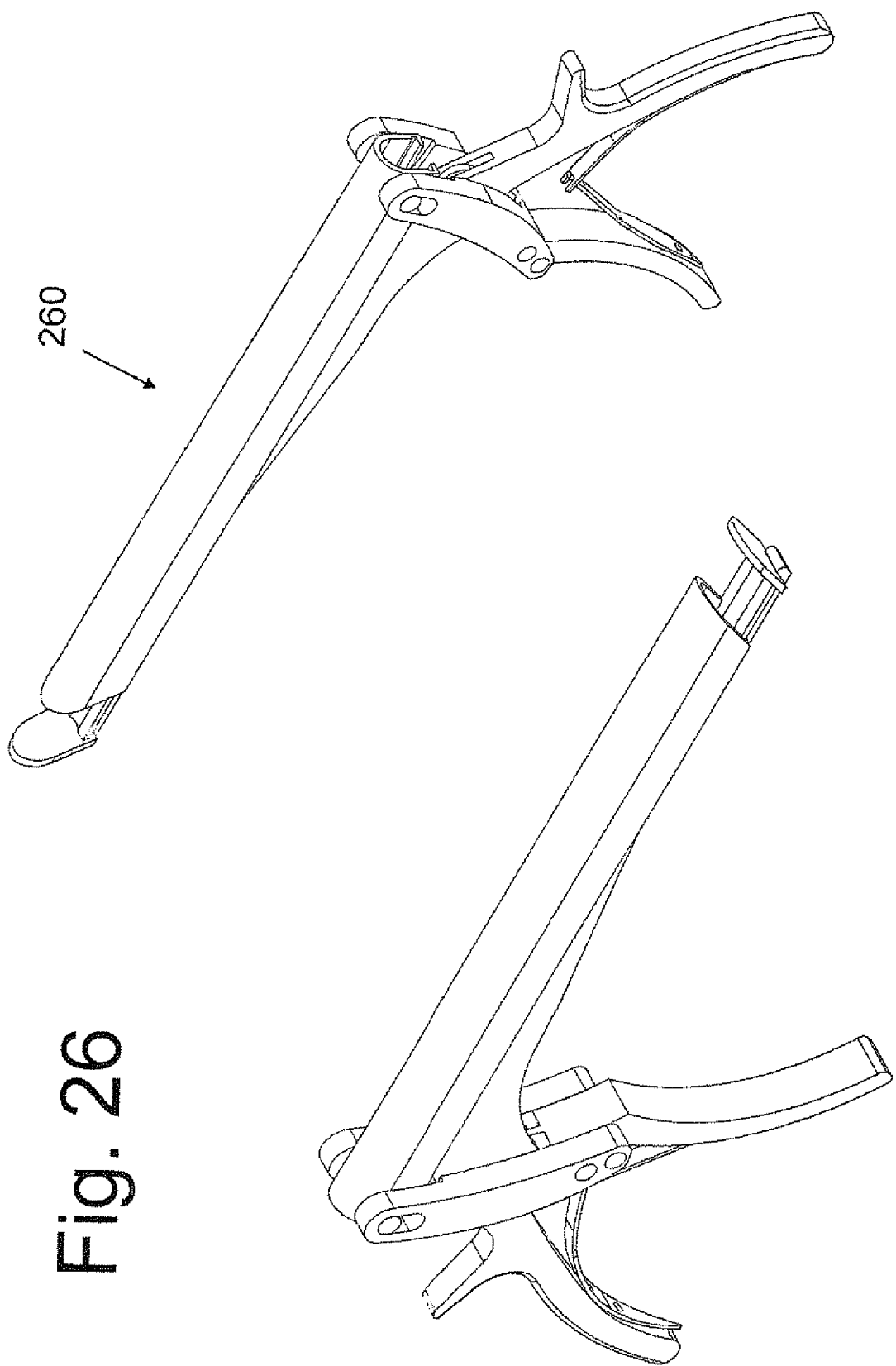
FIG. 26 shows an embodiment of an instrument adapted to perform both the drill and rongeur function.
Figure 27:
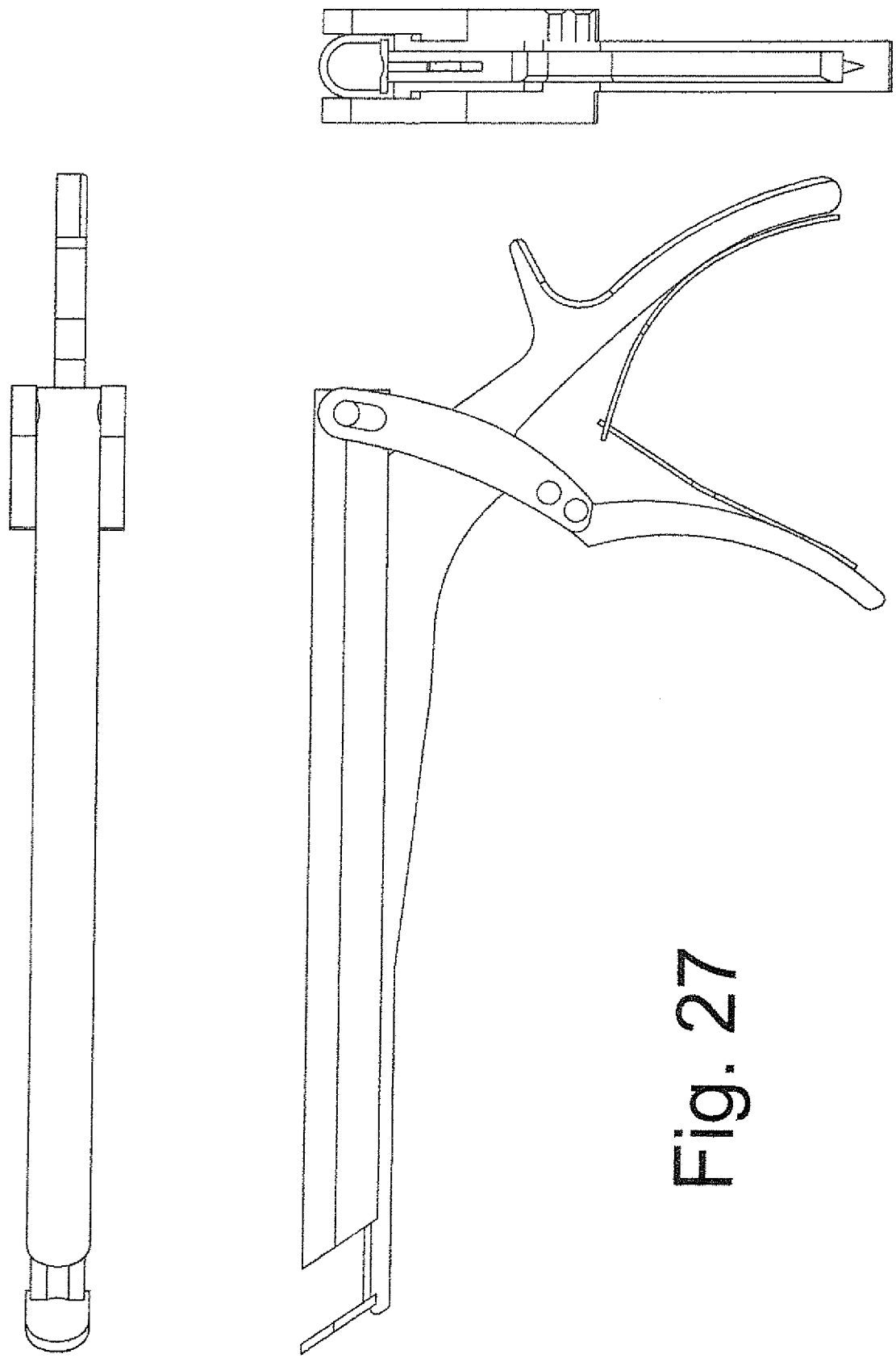
FIG. 27 shows another view of the instrument.
Figure 28:
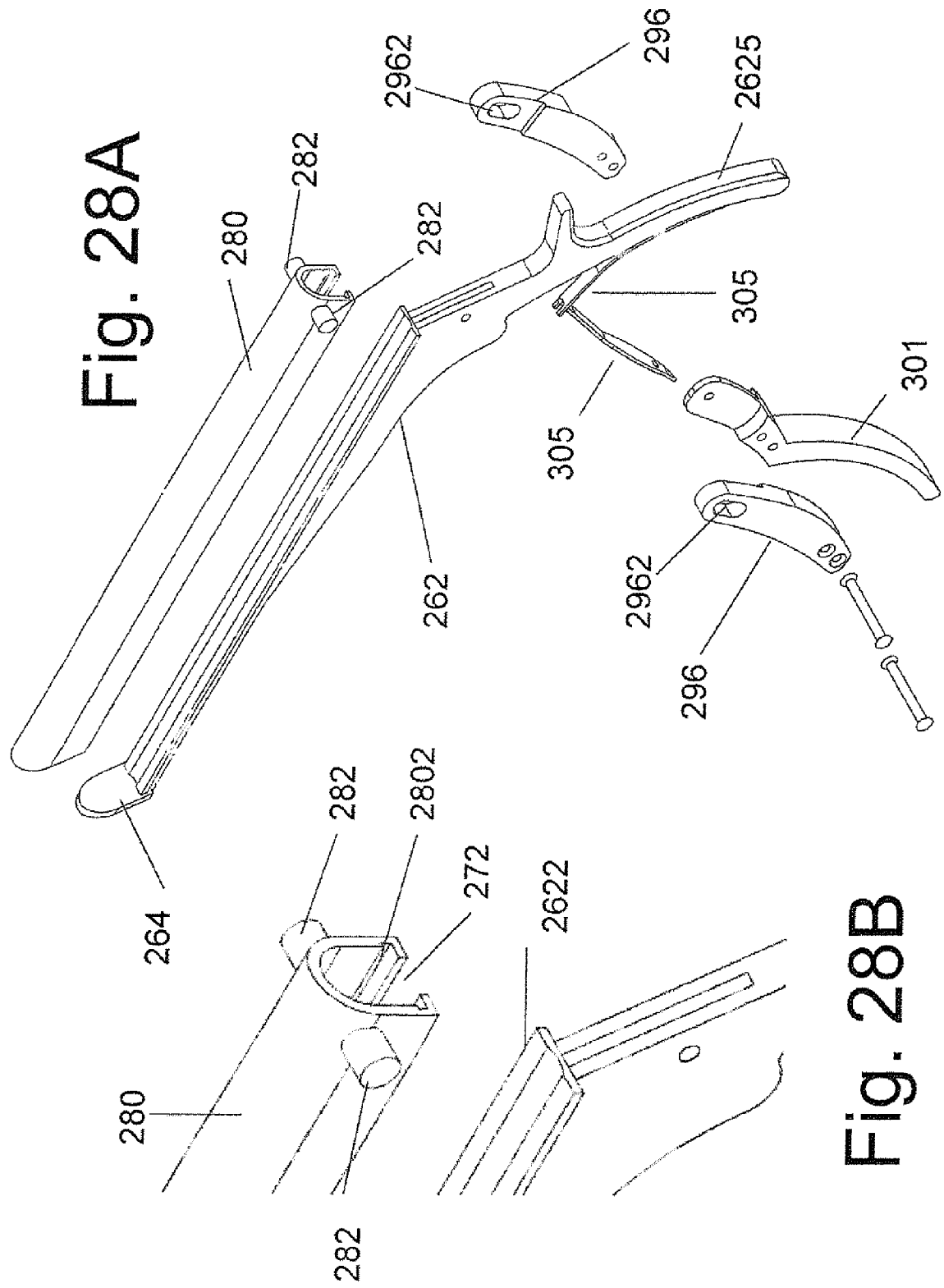
FIGS. 28A-28B show exploded views of the instrument.
Figure 29:
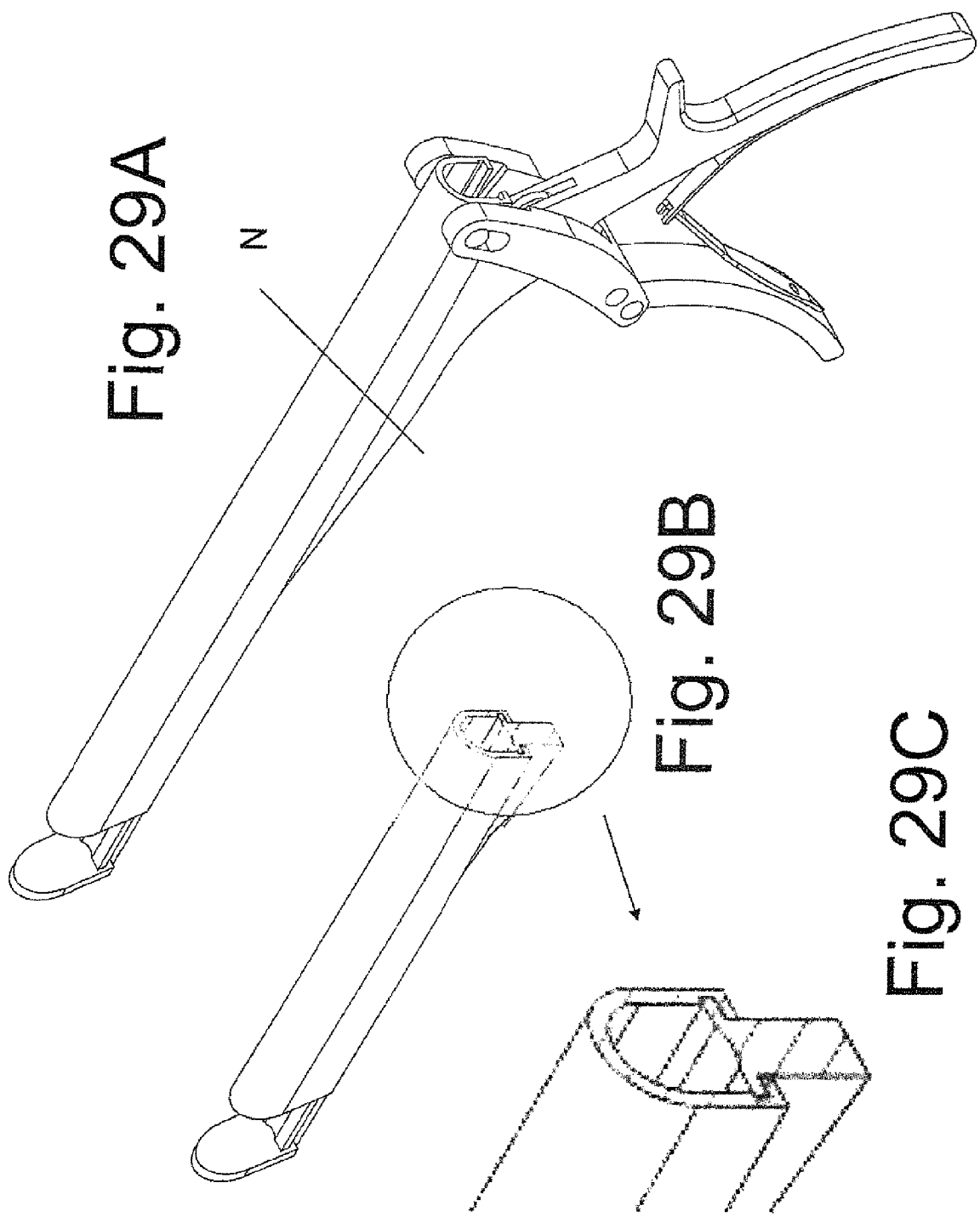
FIGS. 29A-29C show various section views of the instrument.
Figure 30:
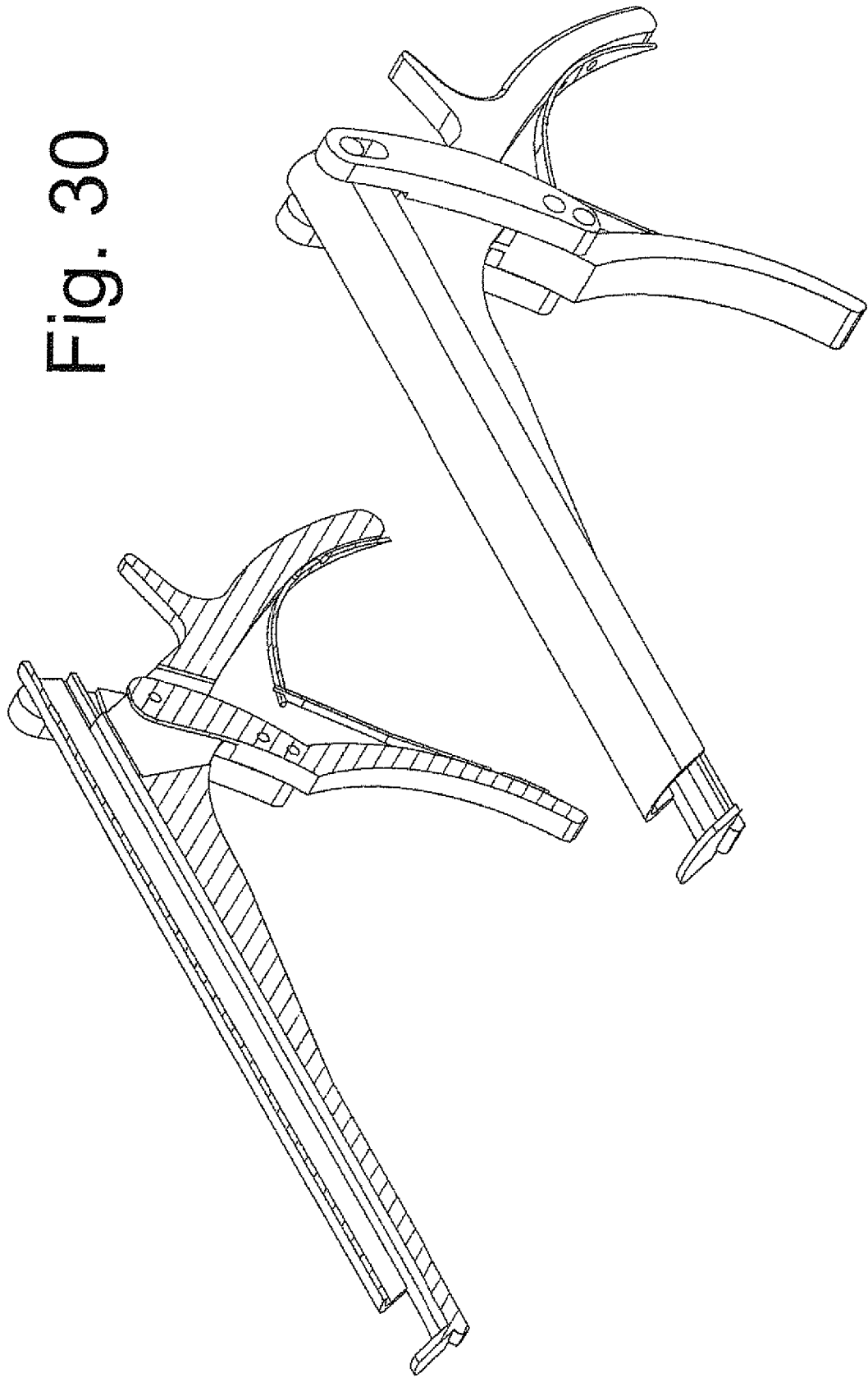
FIG. 30 shows a section view of the instrument.

Instrument 260 is shown in multiple orthogonal views in FIG. 27 and in oblique views in FIG. 26. An exploded view is shown in FIG. 28. Section views are shown in FIGS. 29 and 30. A section view of the device at about plane N is shown in FIG. 29B, wherein a close-up view of the section is shown in FIG. 29C.

A main body 262 has a foot segment 264. While not shown, the foot segment preferably has a sharpened edge about at least a portion of the circumference. wherein the sharpened edge is adapted to cut bone. A movable elongated member 280 has protrusions 282 that are adapted to engage members 296. Member 280 has cut outs 2802 adapted to engage edge 2622 of member 262 so that member 280 can move along the long axis of body member 262. The distal end of member 280 is adapted to forcibly abut the foot segment 264 of body 262. wherein the distal end of member 280 preferably has a sharpened circumferential edge that is adapted to cut bone.

In the assembled device. a central channel 272 is formed between member 262 and 280. A movable handle member 301 is attached to body member 262 using member 296 as shown in the illustrations. Cut out 2962 of member 296 is adapted to engage protrusions 282 of member 280. In use. forcible hand actuation of the handle 301 towards the handle portion 2625 of body 262 produces movement of member 280 relative to body 262 and advances the sharpened distal end of member 280 towards the sharpened foot segment 264. In this way, the intervening bone is cut and instrument 260 functions like a rongeur. Spring members 305 are adapted to return the handle 301 to the pre-actuation position (i.e., the position shown in FIG. 30) after the pressure placed by the surgeon's hand on member 301 has been released.

Figure 31:
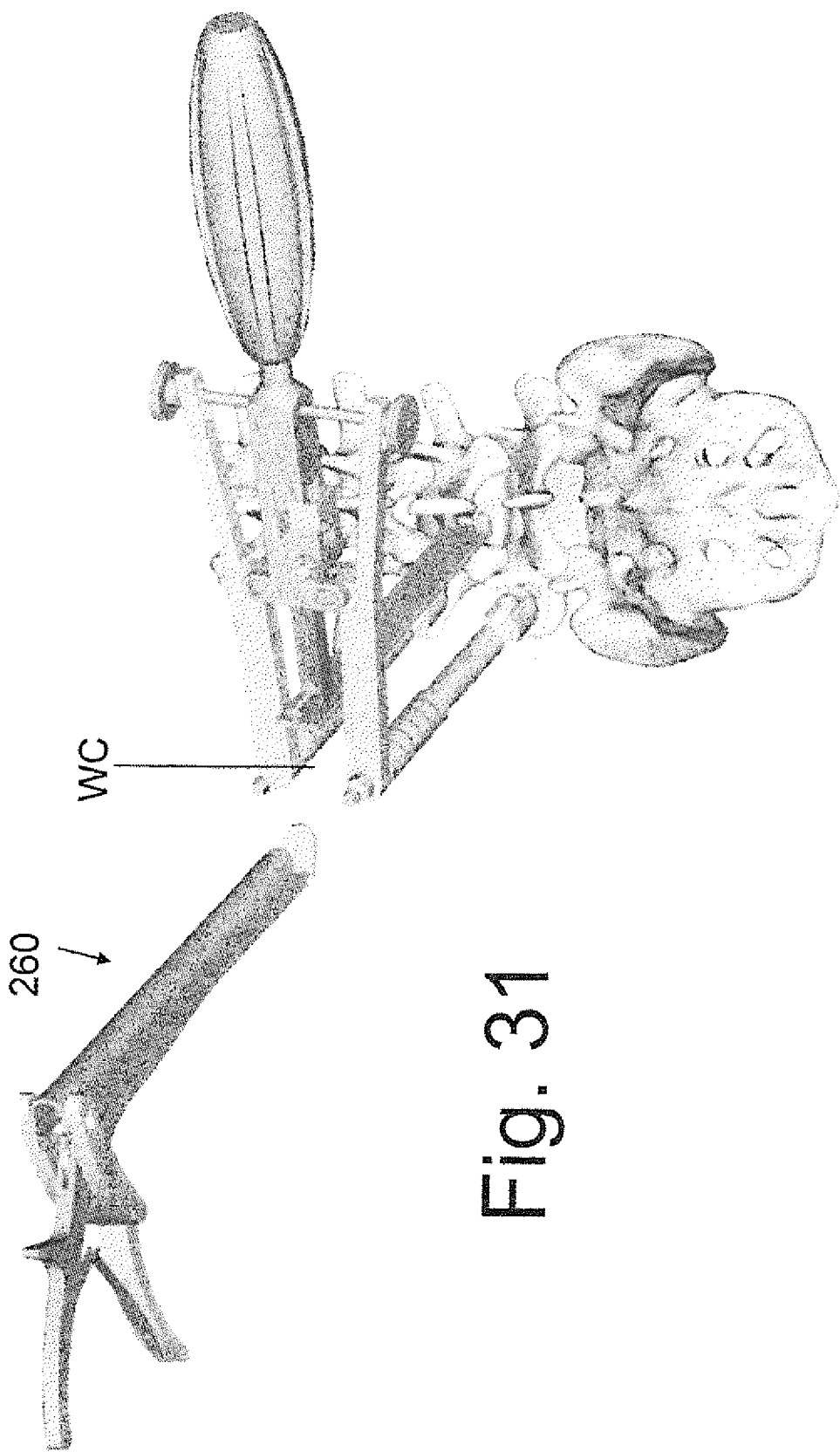
FIG. 31 shows an instrument positioned to be advanced through the working corridor.
Figure 32:
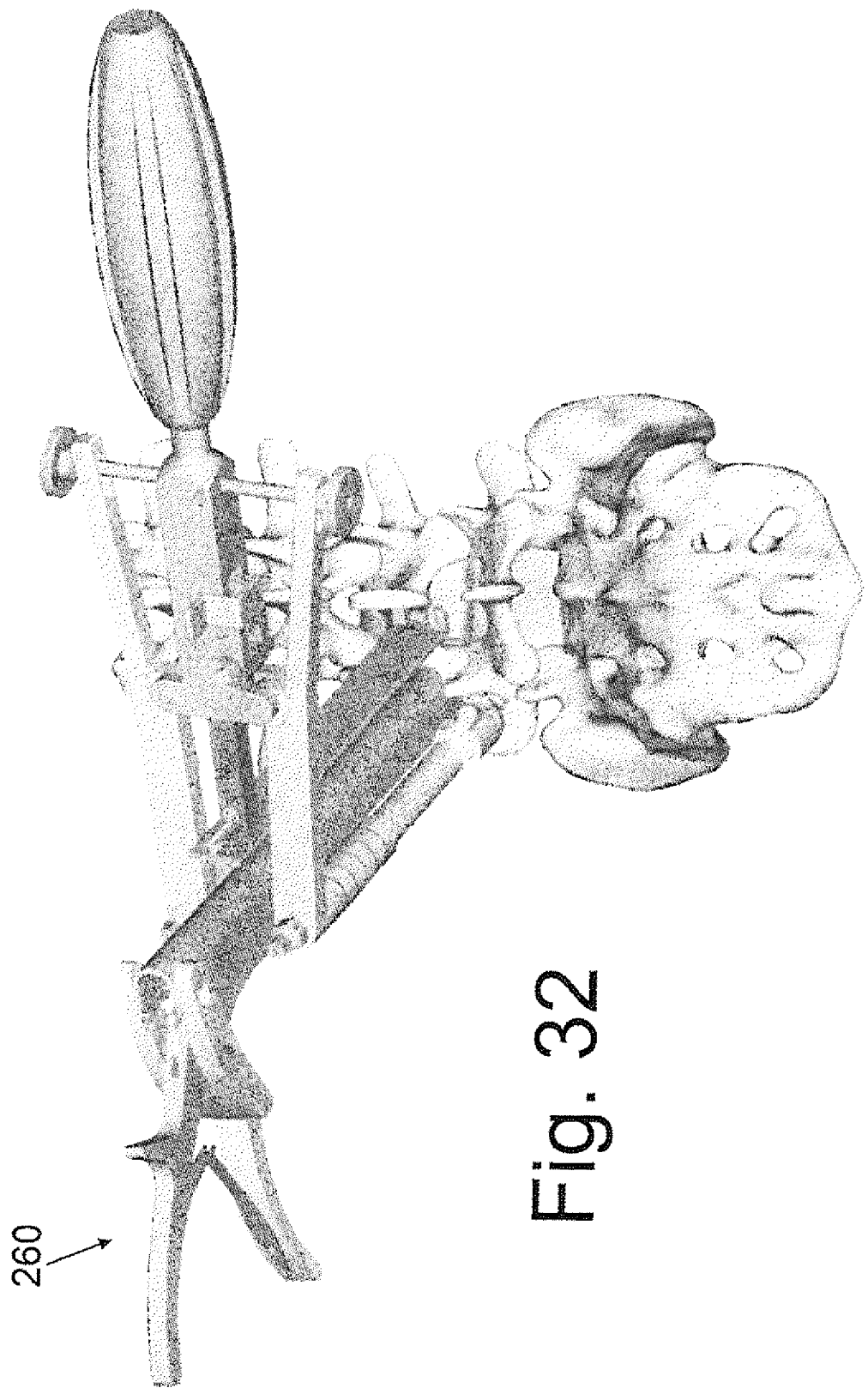
FIG. 32 shows the instrument fully advanced onto the facet joint.
Figure 33:
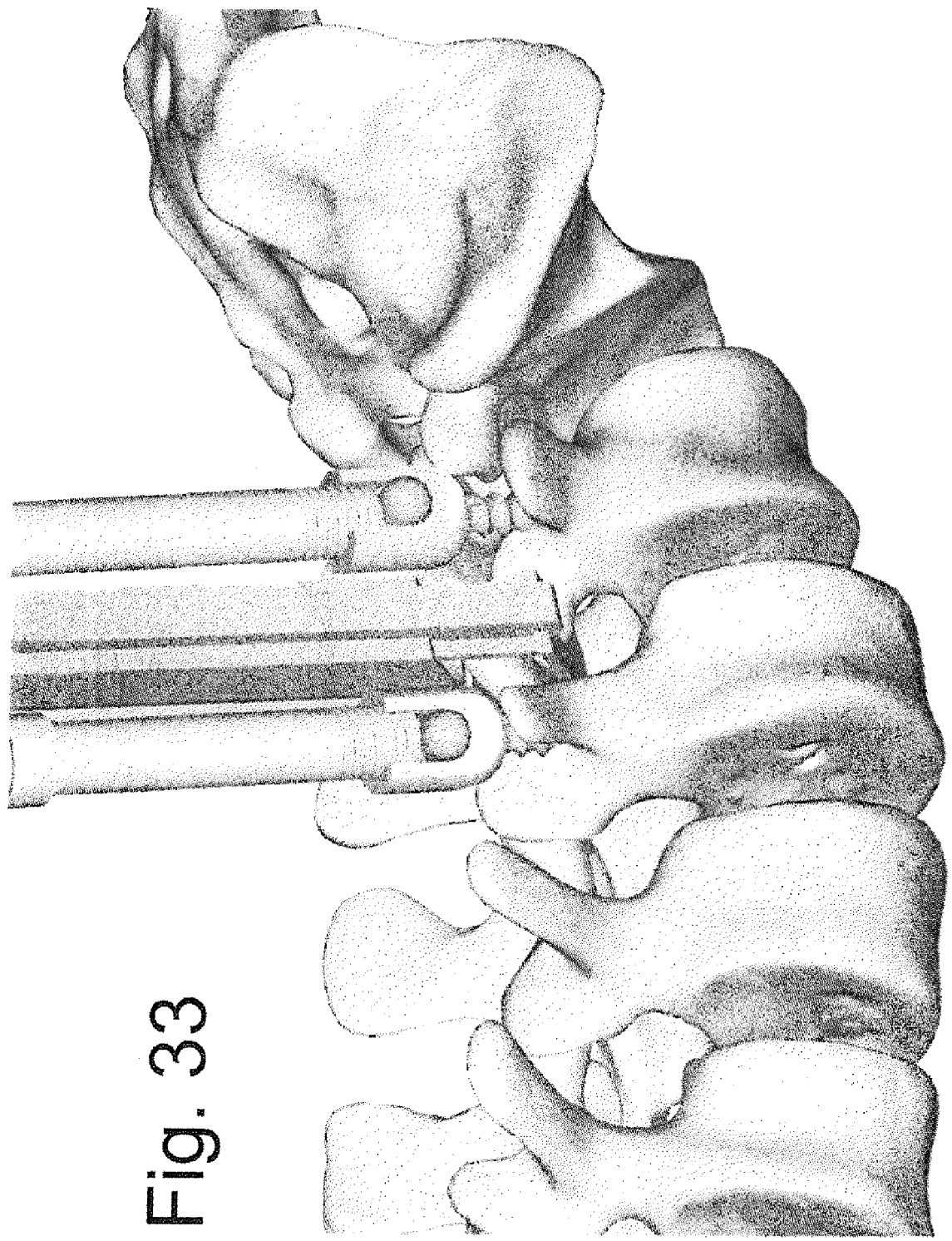
FIG. 33 shows the facet joint positioned between each foot and distal aspect of member of instrument.
Figure 34:
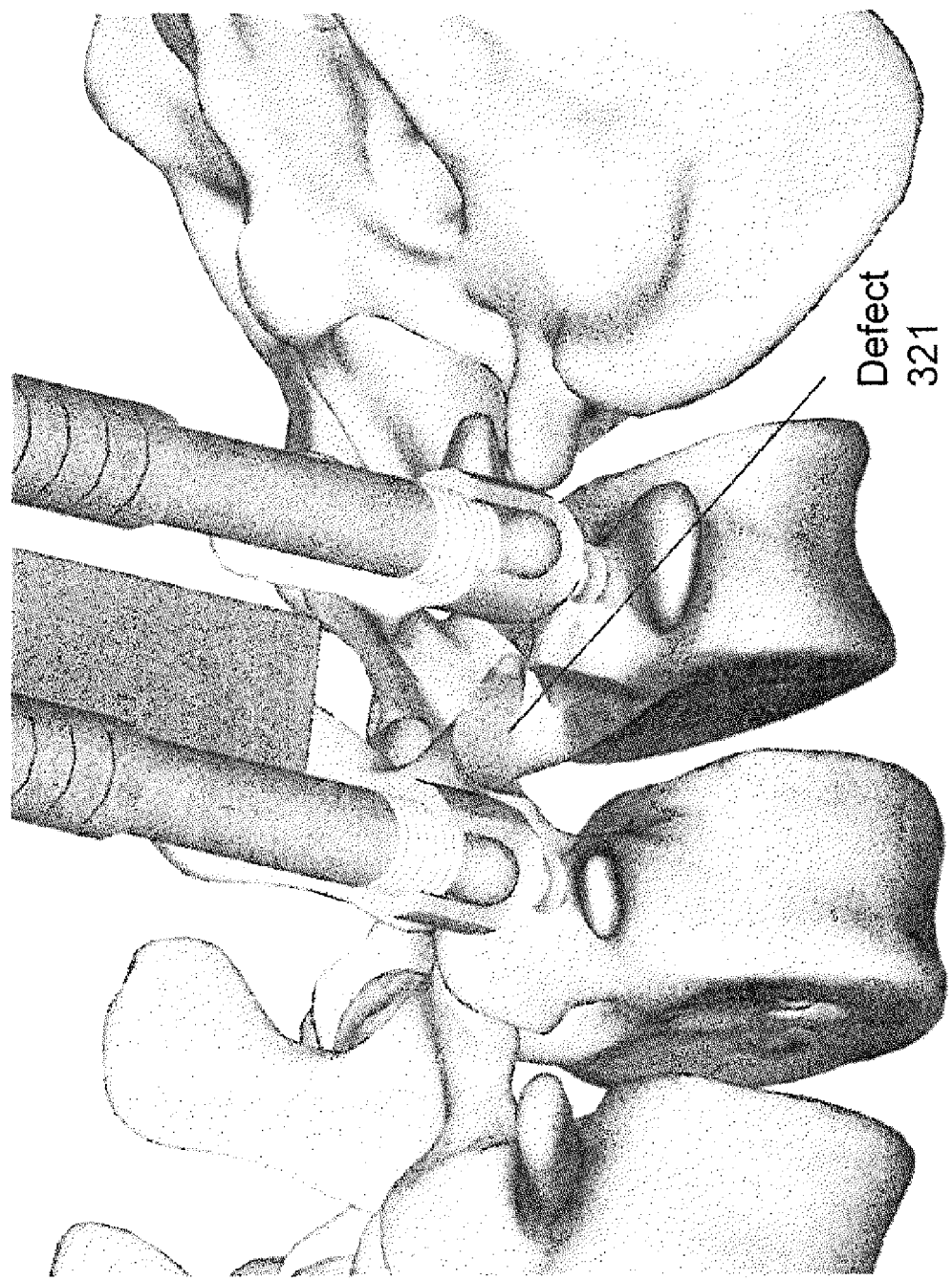
FIG. 34 shows the bone defect formed by instrument with the instrument partially removed.

FIG. 31 shows instrument 260 positioned to be advanced through working corridor WC while FIG. 32 shown the instrument fully advanced onto the facet joint 814. Foot segment 264 of instrument 260 is passed lateral to joint 814 and then moved medially so that the foot segment rests immediately anterior to facet joint 814 (that is, the foot segment 264 resets within the neural foramina of the exiting nerve). The sharpened distal end of member 280 rests posterior to facet joint 814. In this way, the facet joint is positioned between each of foot 264 and distal aspect of member 280 of instrument 260. This is shown in FIG. 33. A drill bit is placed through the central channel 272 of instrument 260 and the facet joint 814 is drilled away until the free end of the drill bit abuts foot member 264. After drilling the facet joint, only a small rim of bone is left between foot 264 and distal aspect of member 280. Hand actuation of handle 301 then cleaves the residual rim of bone. The bone defect 321 formed by instrument 260 is shown in FIG. 34, with the instrument 260 partially removed.

After removal of instrument 260, the surgeon may further remove additional segments of the facet joint with burr, drill, bone rongeur, and the like. If desired, the spinal canal may be also decompressed through the working corridor WC. Removal of at least a portion of the lamina of the superior vertebral bone and at least a portion of the lamina of the inferior vertebral bone permits access to the spinal canal and decompression of both sides of the dural sac and nerve elements. This is schematically shown in FIG. 35, wherein the dural sac (DS) and contained nerve elements are shown decompressed on the posterior and lateral aspects. (For clarity of illustration, the contents of FIG. 35 are represented schematically and those skilled in the art will appreciate that an actual cross section of the human torso may include anatomical details not shown in the illustration.)

After resection of the fact joint, the working corridor WC provides direct access to the posterior aspect of the disc space. The posterior disc space is accessed through a trans-foraminal corridor that extends, in the superior/inferior direction, between the nerve root that exits the spinal canal beneath the pedicle of the superior vertebral bone (L4 vertebra in the illustration) and the pedicle of the inferior vertebral bone (L5 vertebra in the illustration). If vertebral fusion is desired, then at least partial removal of the disc material is performed and a segment of the bony endplate of each of the inferior surface of the superior vertebral bone (L4) and superior surface of the inferior vertebral bone (L5) is striped of cartilage material and then decorticated. Preparation of the disc space is well known in the art and will not be described further.

If vertebral fusion is desired, then bone forming material is positioned into the evacuated portion of the disc space. Preferably, but not necessarily, an implant is concurrently implanted into the disc space that can bear at least some of the load transmitted across the disc space and maintain the superior and inferior vertebral bones separated by a desired distance. While embodiments of disc space implants are shown, it is understood that any device adapted for implantation into the disc space (including those adapted to produce vertebral fusion and those intended to preserve vertebral motion, such as, for example, an artificial disc) may be used.

An embodiment of a disc implant 505 is shown in FIGS. 36A-37. The device is preferably curvilinear. The implant may be solid, as shown in FIGS. 36A-36B, or it may contain a cavity adapted to house bone graft material, wherein the material is adapted to fuse with one or both of the vertebral bones. The implant may be made of allograft bone, PEEK, or any other material that is appropriate for human or animal implantation. Preferably, the implant has a curvature K with center line L. Further, the implant may contain at least one cavity 507 that permits communication from one side of the implant body to the other—as shown in FIG. 37. The cavity permits formation of a bony connection between a fusion mass on one side of the implant body and a fusion mass on the other side of the implant body.

Figure 38B:
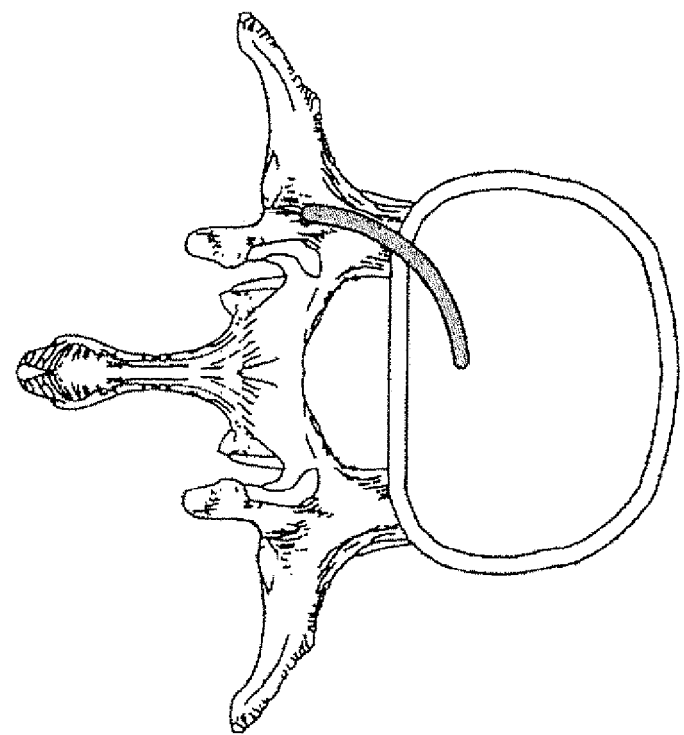
FIGS. 38A-38B show implant positioned at the defect place din the posterior aspect of the annulus fibrosis of the disc space during disc preparation.
Figure 38A:
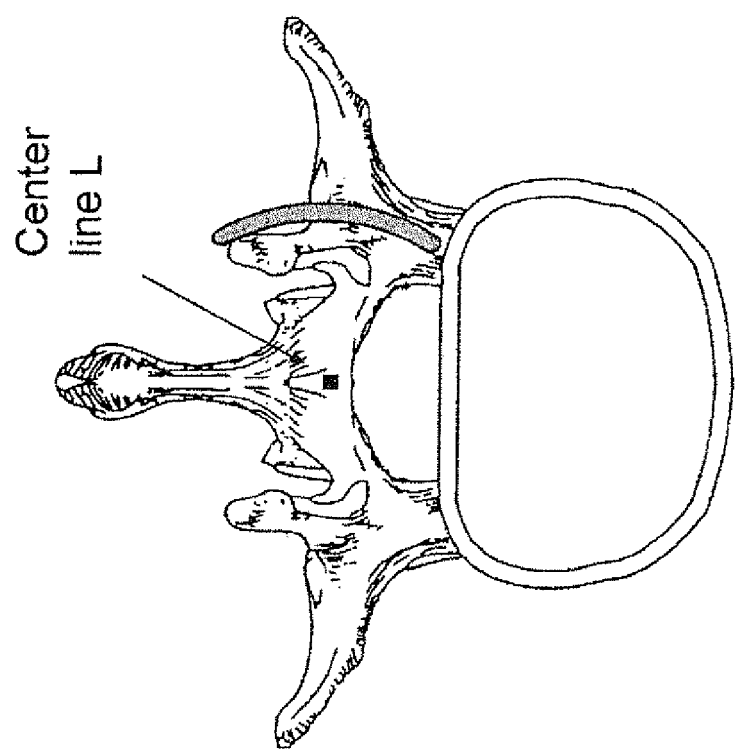
Figure 39:
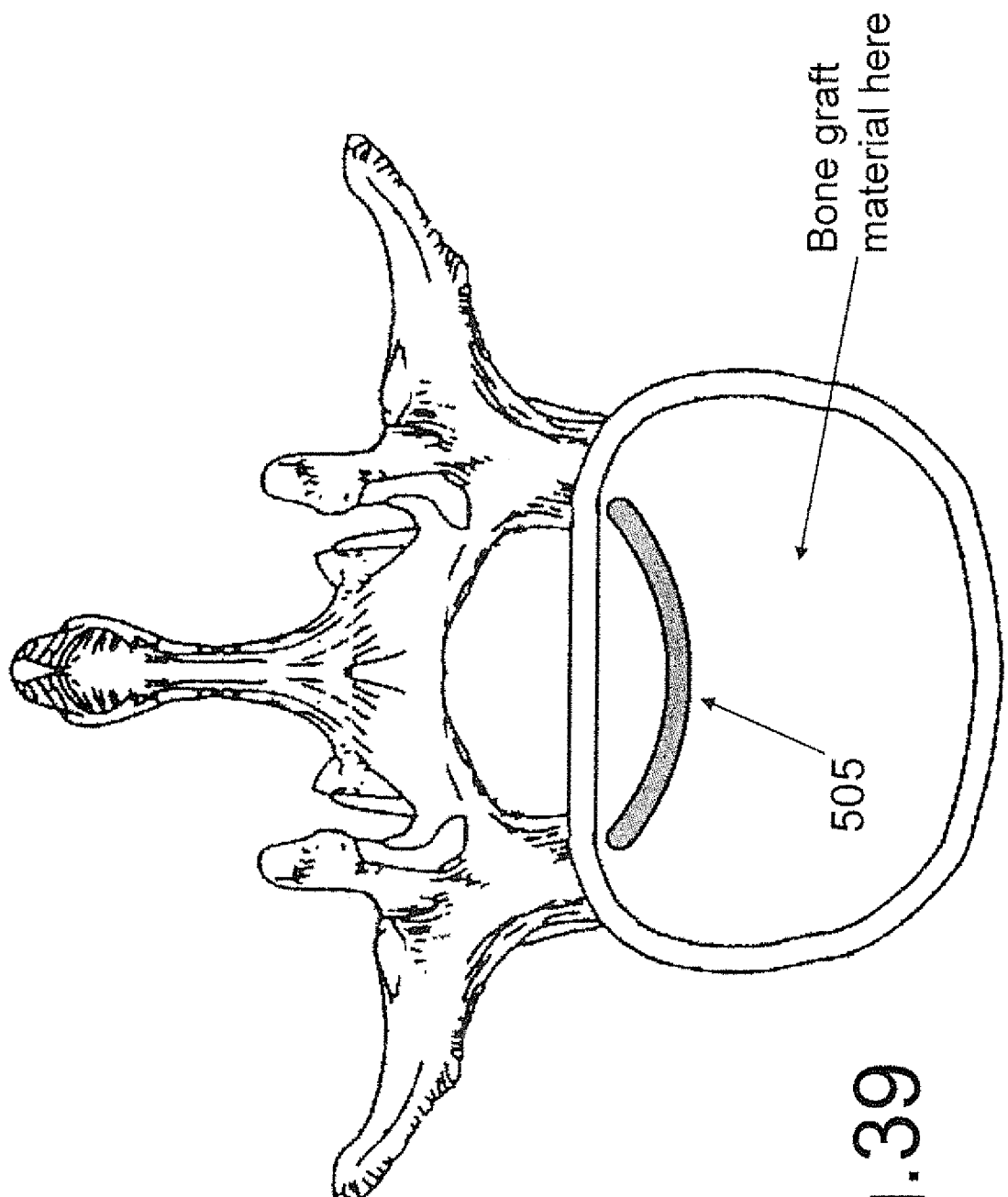
FIG. 39 shows bone graft material placed into the disc space adjacent the implant.
Figure 40A:
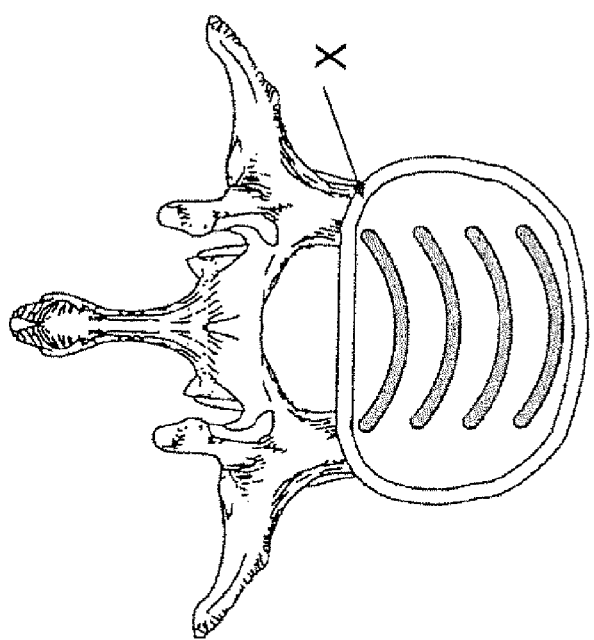
FIGS. 40A-40B show additional embodiments of implant positioning.
Figure 40B:
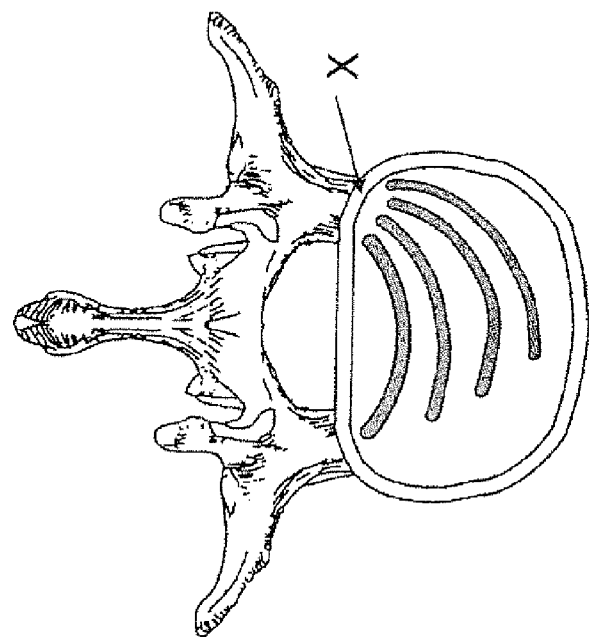

At implantation, the implant 505 is preferably positioned at the defect formed in the posterior aspect of the Annulus Fibrosis of the disc space during disc preparation (see FIG. 38A.) The implant is then rotated along an arc that is centered at the implant's center line L (note that center line L goes in and out of the page). Thus only a point is shown FIG. 38A by an implantation 32 instrument (implantation instrument is not shown). The implant is advanced as shown in FIG. 38B until it rests in the position shown in FIG. 39. Bone graft material is then placed into the disc space adjacent to the implant (see FIG. 39). The bone graft material can be placed into the disc space after implant placement (through the space lateral to the implant) or the bone graft material can be placed before implant placement. Further, more than one implant may be advanced into the disc space. FIGS. 40A and 40B illustrate two potential embodiments of implant positioning, wherein the implants are preferably, but not necessarily, placed through a single disc space entry point "X") within the Annulus Fibrosis.

After implantation of the disc space, the distraction platform is removed. If the surgeon elects to add a fusion mass between the ipsilateral transverse processes of the superior and inferior vertebral bones, then the transverse process of each of the superior and inferior vertebral bones is stripped of the attached muscle and decorticated. A column of bone forming material is then positioned in contact with the transverse process of each of the superior and inferior vertebral bones, wherein the bone forming material also spans the space between the transverse processes. With time, a solid column of mineralized bone should form between the two transverse processes and serve as the fusion mass.

An inter-connecting member (for example, a rod) is used to interconnect each of the superior and inferior bone fasteners 105. A locking element 116 of each bone fastener 105 is then deployed so that each of the bone fasteners is rigidly attached to the interconnecting member. In this way, the fasteners and interconnecting rod member will rigidly interconnect the superior and inferior vertebral bones that abut the implanted disc space and immobilize the FSU containing the target disc space. The sequence is schematically shown in FIGS. 41A-41B.

Additional immobilization may be produced by the implantation of fasteners/interconnecting member into the contra-lateral vertebral pedicles (i.e., on the contra-lateral side of the vertebral midline). A fusion mass may be also positioned, if desired, between the contra-lateral transverse processes of the superior and inferior vertebral bones. Alternatively, or additionally, a spinous process fastener that is adapted to rigidly affix to the spinous process of each of the superior and inferior vertebral bones and rigidly immobilize the FSU may be used as an additional fixation implant. Preferably, the spinous process fastener is placed through the same ipsilateral skin incision used to perform the disc space implantation of the TLIF approach.

Figure 42B:
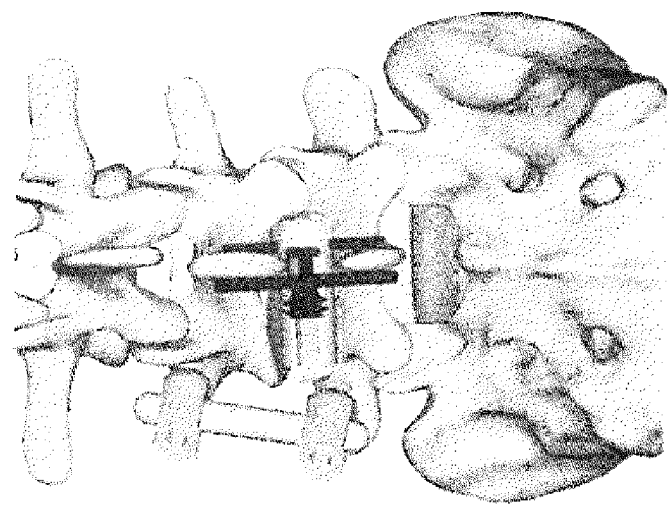
FIGS. 42A-42B show an embodiment of a spinous process device being implanted.
Figure 42A:
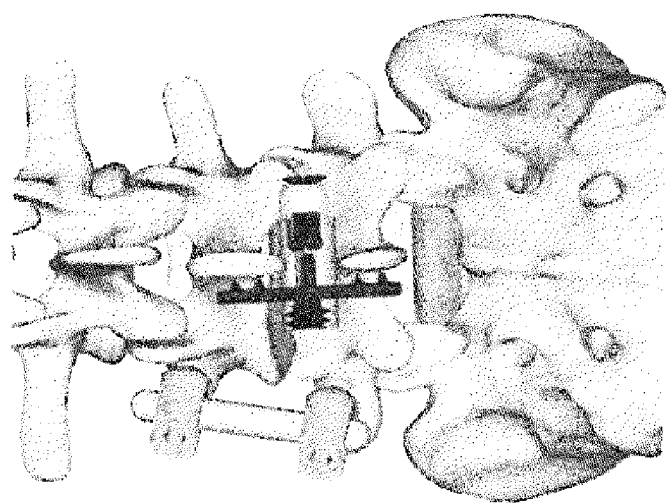

An embodiment of a spinous process device is shown being implanted in FIGS. 42A-42B. The illustrated implant is more fully disclosed in U.S. application Ser. No. 12/940,960, filed by Abdou, Nov. 5, 2010. The application is hereby incorporated by reference in its entirety.

In some patients, the distance between the pedicles of the superior and inferior vertebral bones of an FSU may be small. Under those circumstances, the positioning of a bone anchor assembly 105 into the pedicles each of the superior and inferior vertebral bones may significantly limit the space of the working corridor WC. Thus, it is contemplated that bone screw 107 may be used alone as a bone attachment for the distractor platform—without being attached to housing 110 or the other members of the bone anchor assembly 105.

For example, a bone screw 107 may be attached to a coupler and then advanced into the ipsilateral pedicle portion of at least one of the superior or inferior vertebral bones. As previously described with bone screw assembly 105, a distractor platform is coupled to each of the two screws 107/coupler and a third retractor blade (preferably, a removable tissue distractor blade) is used to retract the soft tissues medially and expose the facet joint. The facet resection and disc implantation is preferably preformed as previously described—but may be alternatively performed using any specific instruments and techniques that the surgeon desires. After disc space preparation and device implantation (previously described), the distractor platform and couplers are removed. The bone screws 107 are left implanted into the pedicle portions of the vertebral bones. If desired. a bone forming material may be used to interconnect the ipsilateral transverse processes of the vertebral bones that border the implanted disc space—as previously described. With time, a bone fusion mass will develop between the transverse processes.

A housing 610 and other member of the complete bone screw assembly may be attached to the bone screw 107 in order to reconstitute a bone screw assembly that can reversibly accept an interconnecting rod. Bone screw assemblies that permit reversible coupling of the housing member to the bone screw 107 are known in the art. U.S. Pat. No. 6,248,105, U.S. Pat. No. 6,371,957 and others disclose bone screw assemblies wherein the housing and the bone screw 107 may be reversibly detached by the surgeon at the time of surgery. (Each citation is hereby incorporated by reference in its entirety.) These devices are designed to permit advancement of the bone screw into bone without an attached housing member. After the bone work is done (or at any time the surgeon chooses), the housing member may be attached to the bone screw so that the assembly is reconstituted and ready to accept an interconnecting rod. After attachment of a housing member to each screw 107, an interconnecting rod and a locking feature (may be a locking screw/nut or a feature built into the housing) is used to lock the interconnecting rod within the bone screw assembly.

FIGS. 43A-43C briefly illustrate an example of a device adapted to perform the method. The assembly of coupler member 630 and screw 107 is shown in an exploded view in FIG. 43A and in the assembled view in FIG. 43B. Sectional views are shown in FIG. 43C. Bone screw 107 has a head 1074 and an internal bore 1076, wherein the internal bore has a threaded portion 1078. A hex-shaped receptacle 1079 resides within head 1074. Receptacle 1079 is adapted to accept a screw driver (with, for example, a hex-shaped tip).

wherein the driver can deliver a rotational force to screw 107 and drive the threaded shaft into bone.

Coupler member 630 has an elongated body with a proximal threaded segment 6302. Member 630 has a central bore 6304 that extends there through from the top to the bottom surface of member 630. A hex-shaped protrusion 6306 projects distally, wherein hex-shaped protrusion 6306 is adapted to snuggly rest within hex-shaped cut out 1079 of screw 107 such that rotation of member 630 produces rotation of screw 107. An additional hex-shaped protrusion 6308 is located at the top of member 630 (i.e., proximal aspect of member 630).

Member 640 has an elongated body with a proximal head 6402 and distal threads 6404. Head 6402 has an indentation (or protrusion) that is adopted to mate and interact a screw driver (not shown) with complimentary protrusion (or indentation), so that rotation of the driver produces rotation of member 640. An internal bore 6409 extends throughout member 640 so that guide wire 102 (FIG. 10) may be passed freely through member 640, entering at a distal end and exiting at a proximal end of 640. In use, threads 6404 are adapted to cooperatively mate with threaded portion 1078 of screw 107. In this way, the assembly of coupler member 630 and screw 107 is rigidly held in the assembled state by member 640 and the assembly is allowed to function as a unitary device.

At surgery, the assembly of member 630 and screw 107 is passed over guide wire 102 to indentation 811 of the targeted vertebral bone. Screw 107 is advanced into bone by applying a rotational force to segment 6308 of member 630. After advancement into bone, the assembly is attached to the distraction platform as previously described. If desired, nut 1107 mates with threads 6302 of member 130 and permits rigid fixation of the assembly onto the distractor platform. These steps are schematically shown in FIGS. 44A-44B.

After the bone work is done (or at any point of the surgeon's choosing), member 630 is detached from bone screw 107. Housing members 610 are then attached to the bone screws 107. This is schematically shown in FIGS. 45A-45B. The screw assemblies are then ready to accept an interconnecting rod. The rod/locking screw may be then inserted and used to interconnect the bone screw assemblies as previously described (see FIGS. 41A-41B).

Note that this methods of use differs from the previously illustrated embodiment only in that the screw assembly 105 my be reversibly subdivided at the time of surgery into the bone screw 107 and housing portion. That is, the screw assembly 105 need not be used as a unitary device through out the procedure, but the screw 107 may be used independently for a first portion of the procedure and then coupled to the housing for use as an assembly at a second portion of the operation. Further, it is understood that the preceding method of use may be alternatively employed in any patient group, regardless of the distance between the pedicles of the superior and inferior vertebral bones.

Figure 45C:
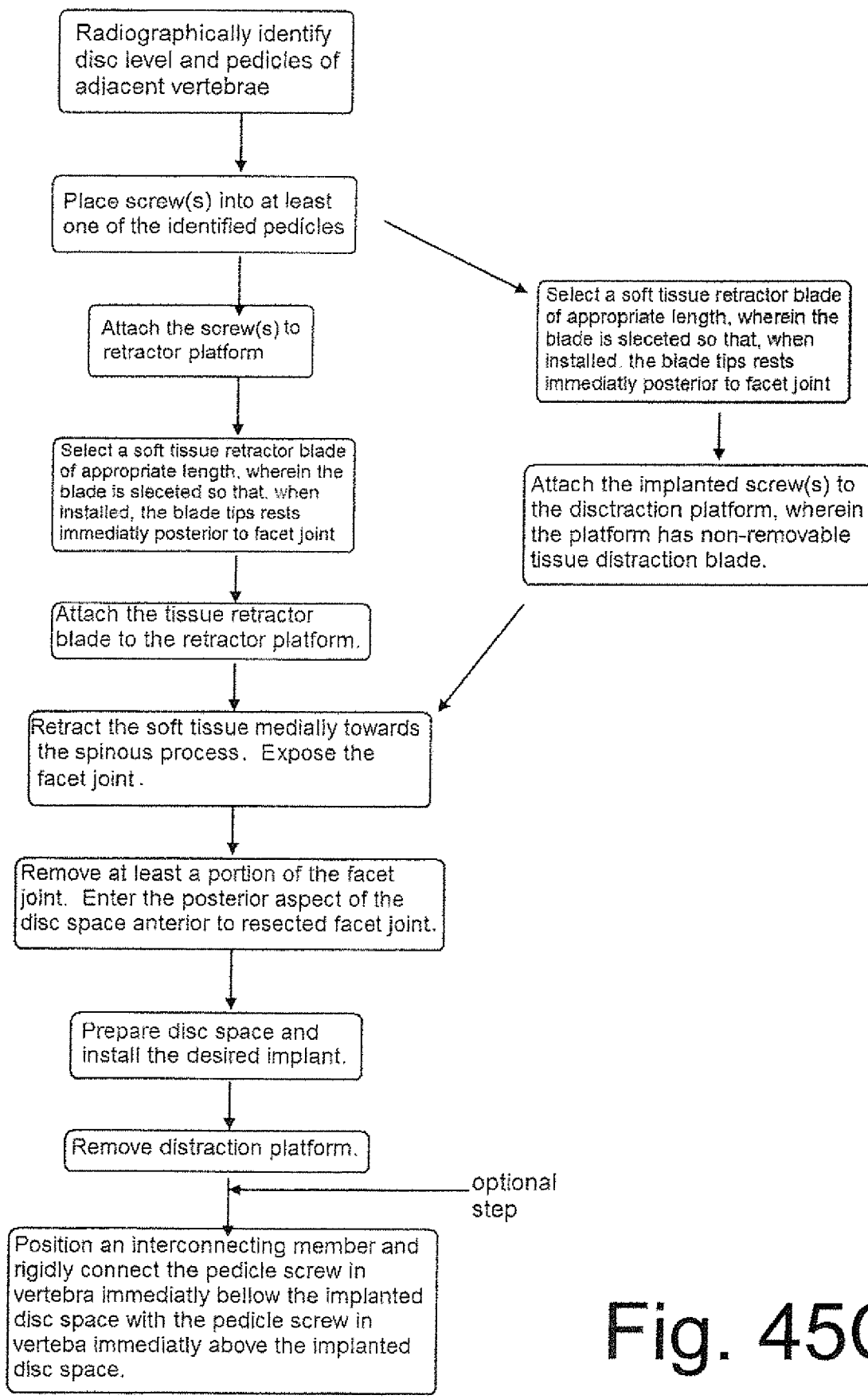
FIG. 45C is a flow diagram summarizing the disclosed methods.

In a modification of the immediately previous method, assembly 630 and screw 107 are left attached after disc space implantation. Instead, the complete 630/107 assembly is removed for the vertebral bone, leaving an evacuated bone screw hole. A separate bone screw assembly 105 (of any applicable design) is then advanced into the pedicles that have been evacuated by the removed coupler member 630/screw 107 assembly. That is, in this method, member 630/screw 107 are used as a temporary distraction screw and coupling platform for distractor 180. After completion of the disc space implantation, the temporary distraction screw (consisting of member 630 and screw 107) is removed and a bone screw assembly 105 is advanced into the evacuated pedicle portion of the vertebral bone. The implanted bone screw assemblies 105 may be then interconnected with a rod—as previously described (see FIGS. 41A-41B). A flow chart summarizing the disclosed methods is shown in FIG. 45C.

In an additional embodiment, threaded screw member 730 is used to anchor a distraction platform to the pedicle portion of the vertebral bone. Screw 730 has a threaded portion 7310 and elongated body 7300 (FIGS. 47A and 47B). Body 7300 has proximal threaded segment 7302. A hex-shaped protrusion 7308 is located at the top of member 730 (i.e., proximal aspect of member 730). Member 730 has a central bore 7304 that extends there through from the top to the bottom surface so that guide wire 102 (FIG. 10) may be passed freely through member 730.

As previously described, at least one guide wire 102 is radiographically guided into the pedicle portion of at least one vertebral bone. Member 730 is passed over guide wire 102 (wire 102 traverses central bore 7304) and threaded portion 7310 is advanced into the pedicle portion of the vertebral—as shown in FIGS. 47A and 47B. Retractor platform 745 is shown in FIGS. 48A-48C. The retractor is known in the art and similar platforms have been disclosed in U.S. Pat. No. 5,795,291, US publications 2005/0021040, 2006/0149278, 2009/0171394 and others. (Each citation is hereby incorporated by reference in its entirety.) Any of these retraction platforms may be alternatively used.

The retractor platform 745 has at least two curvilinear blades 7452 and 7453. Blade 7452 is rigidly connected to bar 7455, while blade 7453 is movable along bar 7455. Thumb wheel 7458 is connected to a screw which threadedly engages threaded bore of blade 7453 (mechanism is not shown). In this way, rotation of thumb wheel 7458 produces translational movement of blade 7453 along bar 7455. Each blade contains at least one bore 7451, wherein the bore 7451 is adapted to accept member 730.

While briefly described above, it is understood that retractor 745 and similar retractor platforms are known in the art and have been disclosed in U.S. Pat. No. 5,795,291, US publications 2005/0021040, 2006/0149278, 2009/0171394 and others. (Each citation is hereby incorporated by reference in its entirety.) Any applicable retractor platforms may be alternatively used to accomplish the illustrated method of exposing the facet joint.

Figure 49:
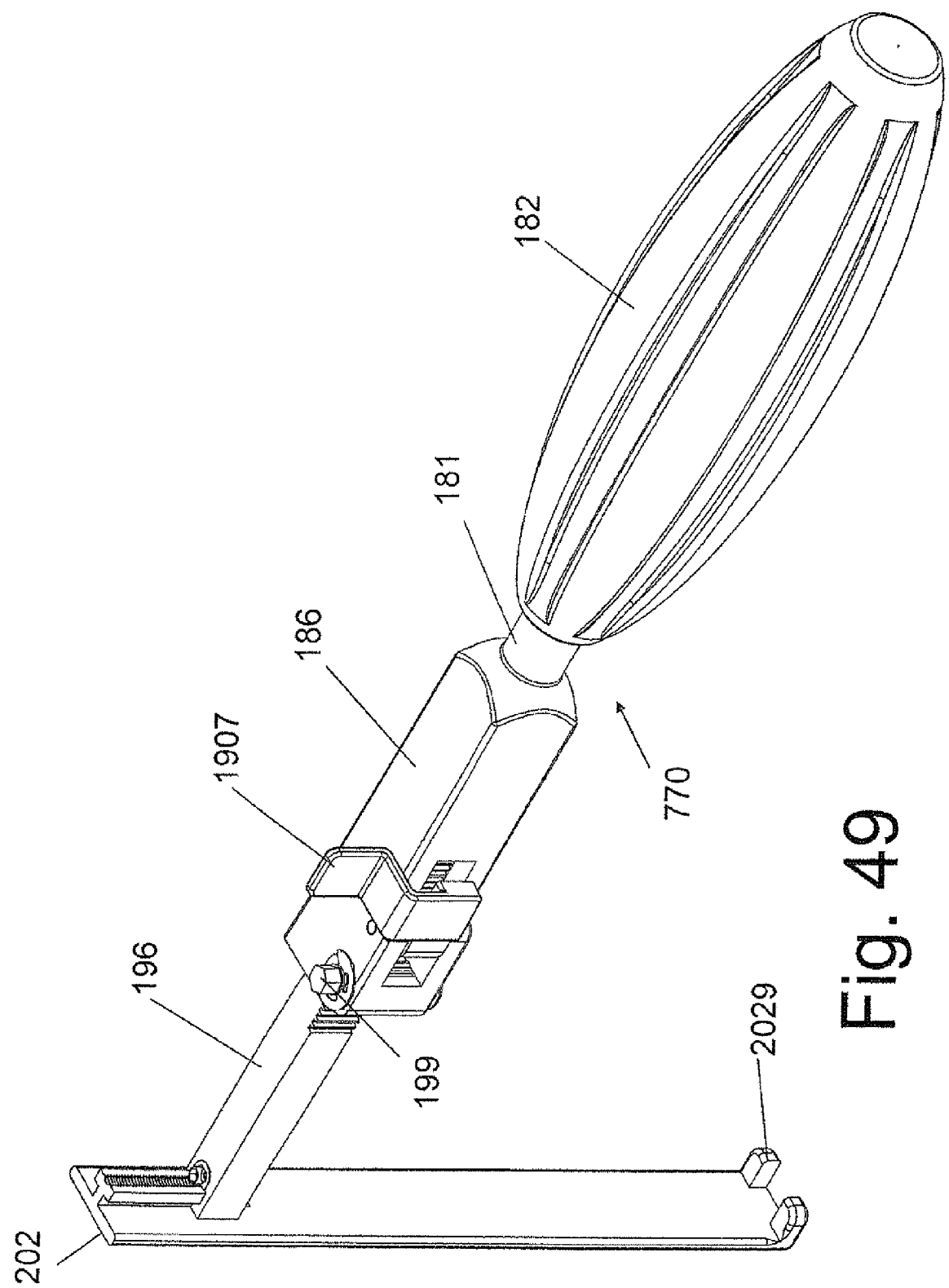
FIG. 49 shows a retractor used to retract the muscle segment medially towards the spinous process.

After advancement of threaded portion 7310 into the pedicle portion of the vertebral bone, the retractor 745 is advanced over member 730 to the correct position and coupled to the underling bone through member 730 (see FIGS. 4813 and 48C). A retractor 770 (FIG. 49) is used to retract the muscle segment M1 medially towards the spinous process—as shown in FIG. 48B. Retractor 770 is similar to distractor 180 but lacks side retractor members 190. That is, retractor 770 contains handle 182, central body member 186 and interconnecting cylindrical region 181. Arm 196 rests within a cavity of central body 186 and is movable therein. A spring-loaded (spring not shown) pawl 1907 and member 199 interact with serrations 198 of arm and serve as a mechanism to move arm into and out of bore 1869 of body 186. A removable tissue retractor 202 rests at the distal end of arm 196. Arm 202 has at least one distal extension 2029 that interact with the retracted tissue. A more full description of the distractor is provided above.

Retractors 745 and 770 are preferably connected to a frame device that anchors to the operating table (such as, for example that shown 25D). Preferably, the frame device attaches to segment 181 of retractor 770 and to the region of bore 7459 of retractor platform 745. After the frame device is locked and made rigid, the attached retractor platforms 745 and 770 are held in desired positions as shown in FIG. 48C. In this way, a working corridor leading to the facet joint is created wherein two of the retractor blades are connected to a retractor platform which may (or may not) be subsequently connected to a frame device that is attached to the operating table. The third retractor is independently attached to the frame device.

An alternative embodiment is shown in FIG. 50. In this embodiment, both bar 7455 is a member of the frame device that is attached to the operating room table. Each blade member 7453 may be guided to the pedicle by anchored member 730 and then reversibly mountable onto bar 7455. (The blades may be radiographically guided to the pedicle position without prior placement of member 730. In order to illustrate this option, a first blade 7453 is shown attached to screw 730 in FIG. 50 while a second blade 7453 is not.) After moving the blade member into the desired position relative to bar 7455, a locking mechanism (set screw 792 here) is actuated to immobilize the blade member relative to bar 7455. As before, retractor platform 770 is also attached to the frame device. In this way, each of the three retractor blades that form and border the working corridor are independently attached to the frame device that attaches to the operating table.

In an alternative embodiment, at least a first vertebral bone of the first and second vertebral bones that must be fused is radiographically identified. A first facet joint is also radiographically identified, wherein the first facet joint forms an articulation between the first and second vertebral bones. A marker is radiographically guided directly into the facet joint and the retractor platform is then advanced over the marker to the facet joint. In the preferred embodiment, a first threaded segment of a first bone fastener is threadedly advanced into the identified first facet joint under radiographic guidance prior to retractor platform placement. The anchored first bone fastener is used to guide and position the retraction platform relative to the first facet joint.

Figure 46B:
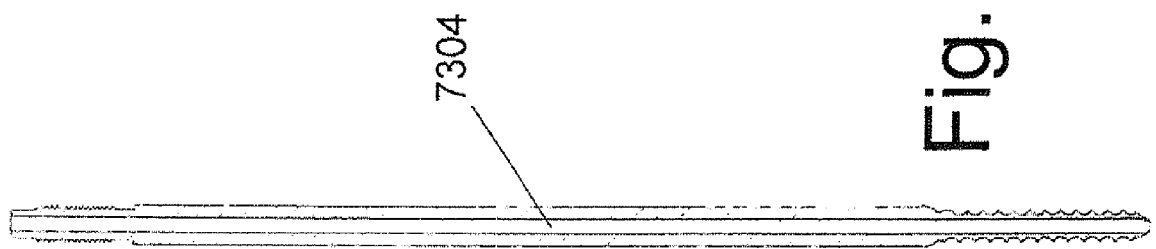
FIGS. 46A-46B show embodiment of a screw member.
Figure 46A:
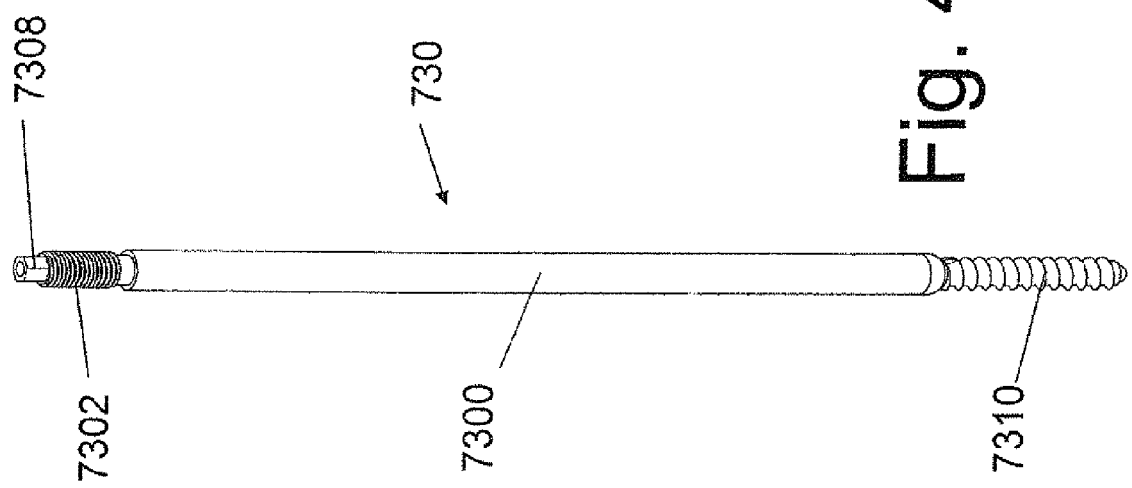
Figure 51A:
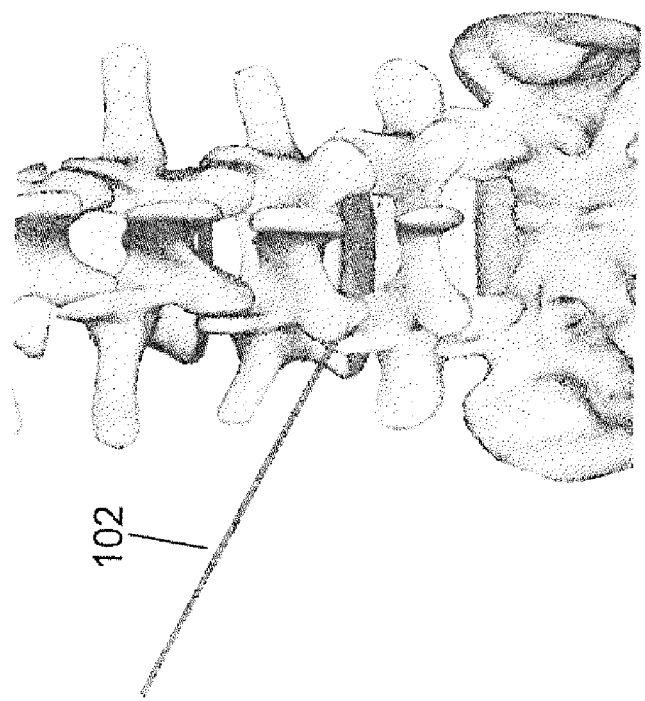
FIGS. 51A-51C show placement of guide wire directly into facet joint space between the IAP of the superior vertebral bone and SAP of the interior vertebral bone.
Figure 51B:
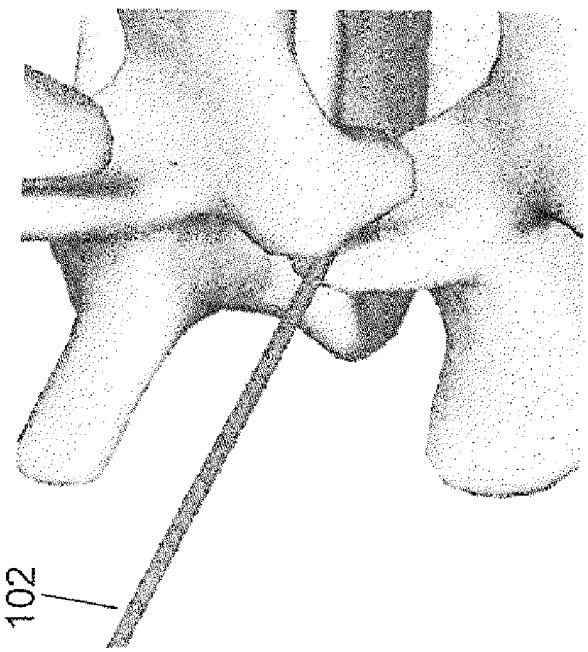
Figure 51C:
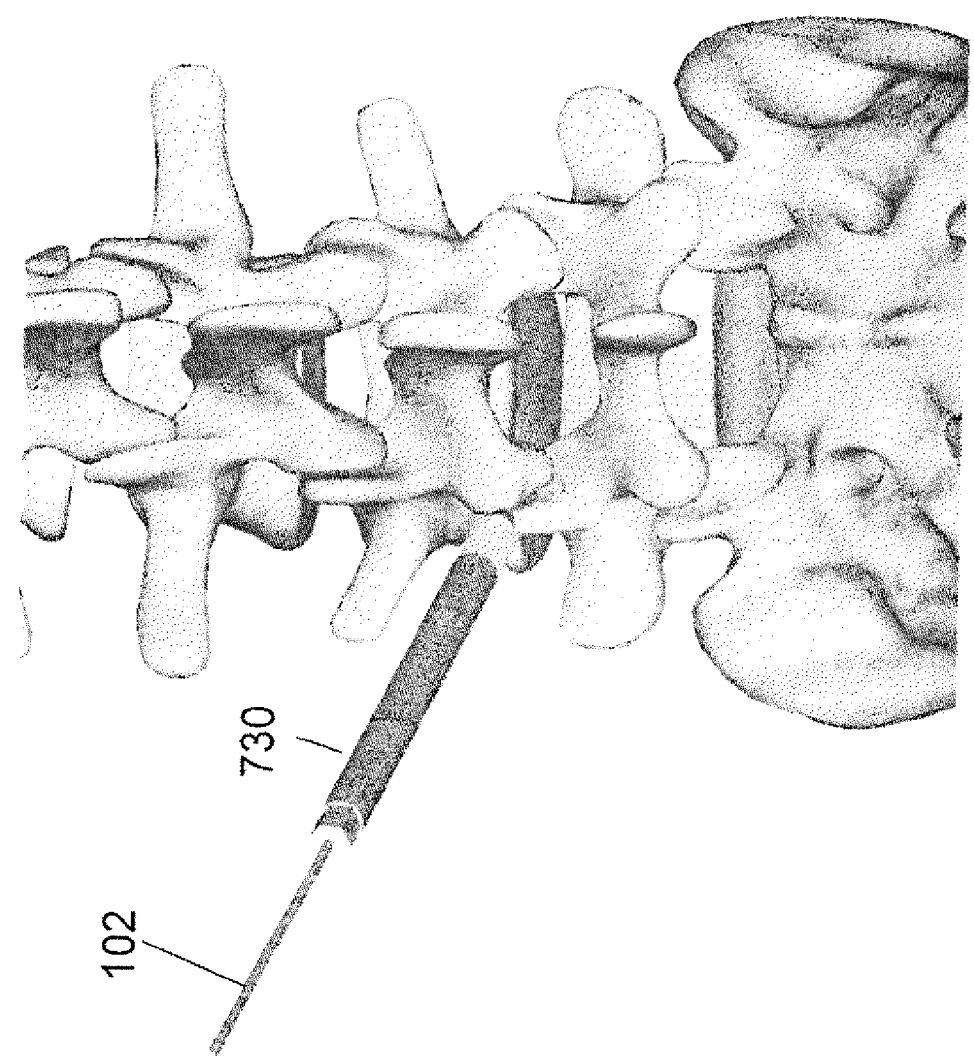

FIGS. 51A and 51B show placement of guide wire 102 directly into the facet joint space between the IAP of the superior vertebral bone and SAP of the interior vertebral bone. (As in prior embodiments, this step is performed under radiographic guidance and prior to direct surgical exposure of the facet joint.) A screw member, such as, for example, member 730 (FIG. 46A-46B) is advanced over the guide wire 102 under radiographic visualization. Threaded segment 7310 is driven into the facet joint so that the threads engage the IAP (superior vertebra) medially and the SAP (inferior vertebra) laterally (FIG. 51C).

Figure 52A:
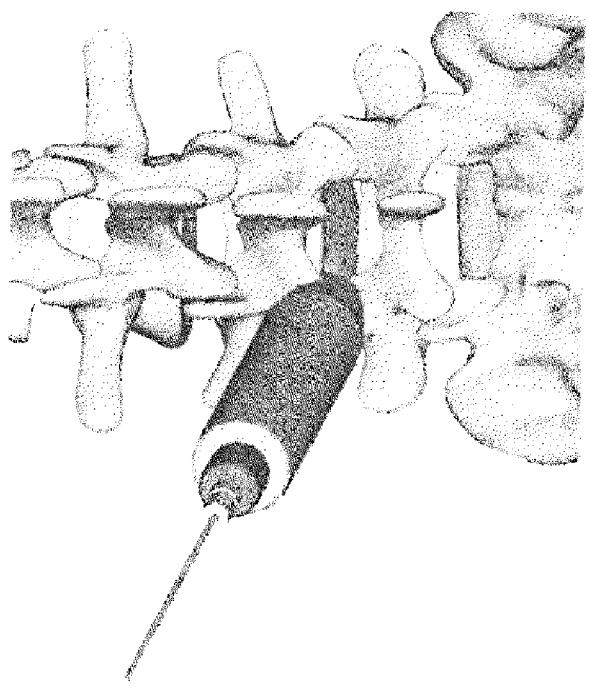
FIGS. 52A-52B show cylindrical tubes of progressively greater diameter sequentially passed over member to dilate surrounding soft tissue and advancement of retractor platform . . . .
Figure 52B:
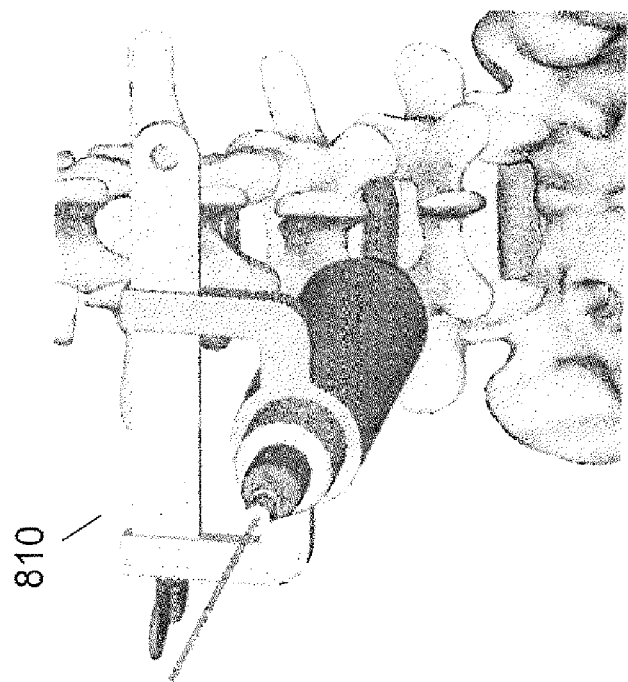

Cylindrical tubes of progressively greater diameter are sequentially passed over member 730 in order to dilate the surrounding soft tissue (FIG. 52A). This method of serial advancement of cylindrical tubes is well known to those of ordinary skill in the art. A retractor platform 810 is then advanced over the cylindrical tubes—as shown in FIG. 52B. While the blades are configured differently, the retractor platform 810 is similar to retractor 745 and description of the retractor will not be repeated. The semicircular tissue retraction retractor blades of retractor 810 are preferably, but not necessarily, devoid of bore 7451.

After advancement of retractor platform 810, the cylindrical tubes and member 730 are removed leaving a working corridor within the central aspect of the semi-cylindrical retractor blades (FIG. 53A). The blades may be separated further by actuating thumb wheel 7458 in order to provide a larger working corridor (FIG. 53B). If desired, the platform 810 may be attached to a frame device (similar to FIG. 25D) that is anchored to the operating table. The frame device may attach to the region of bore 7459 of retractor platform 810.

Figure 25D:
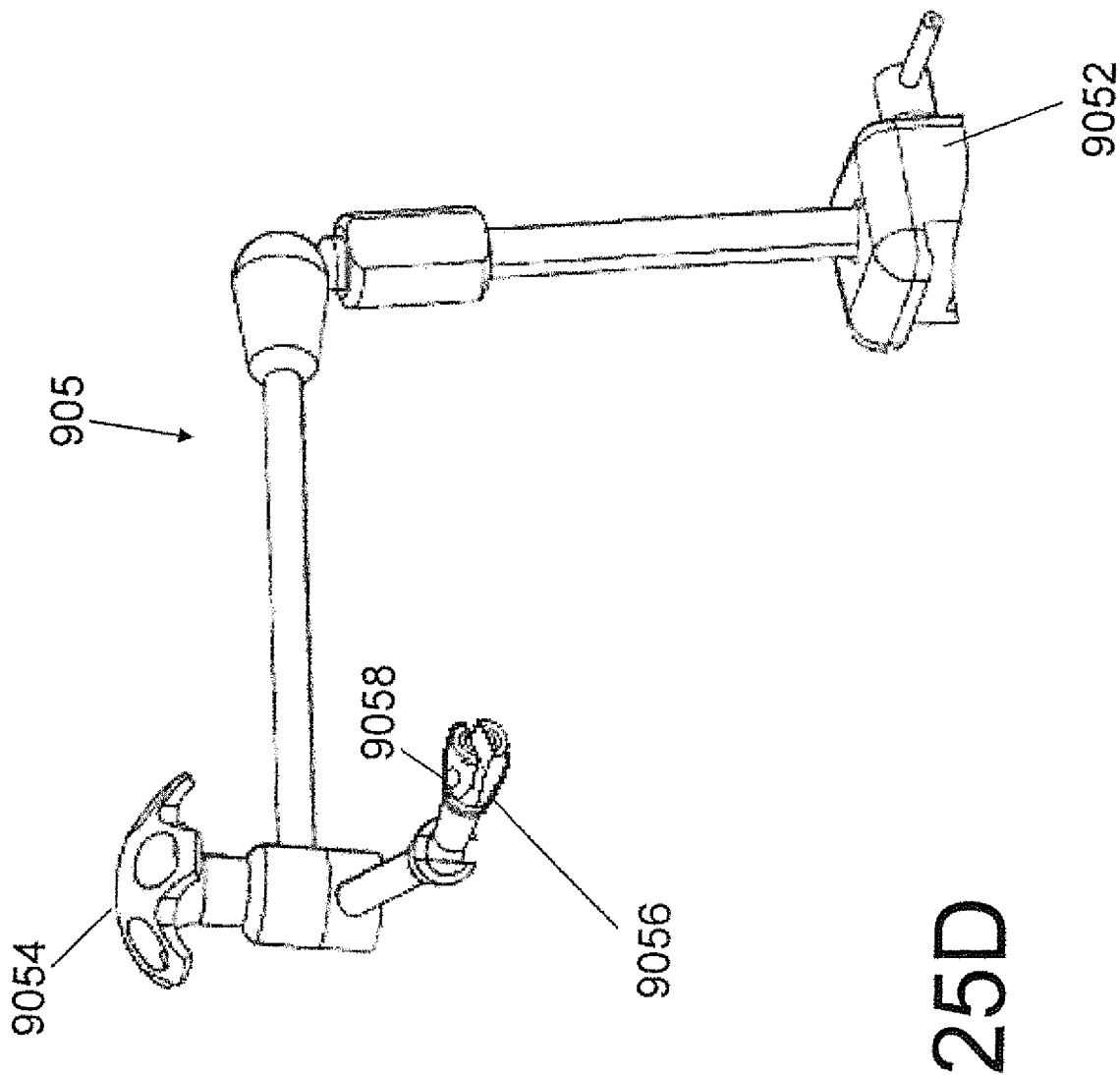
Figure 54:
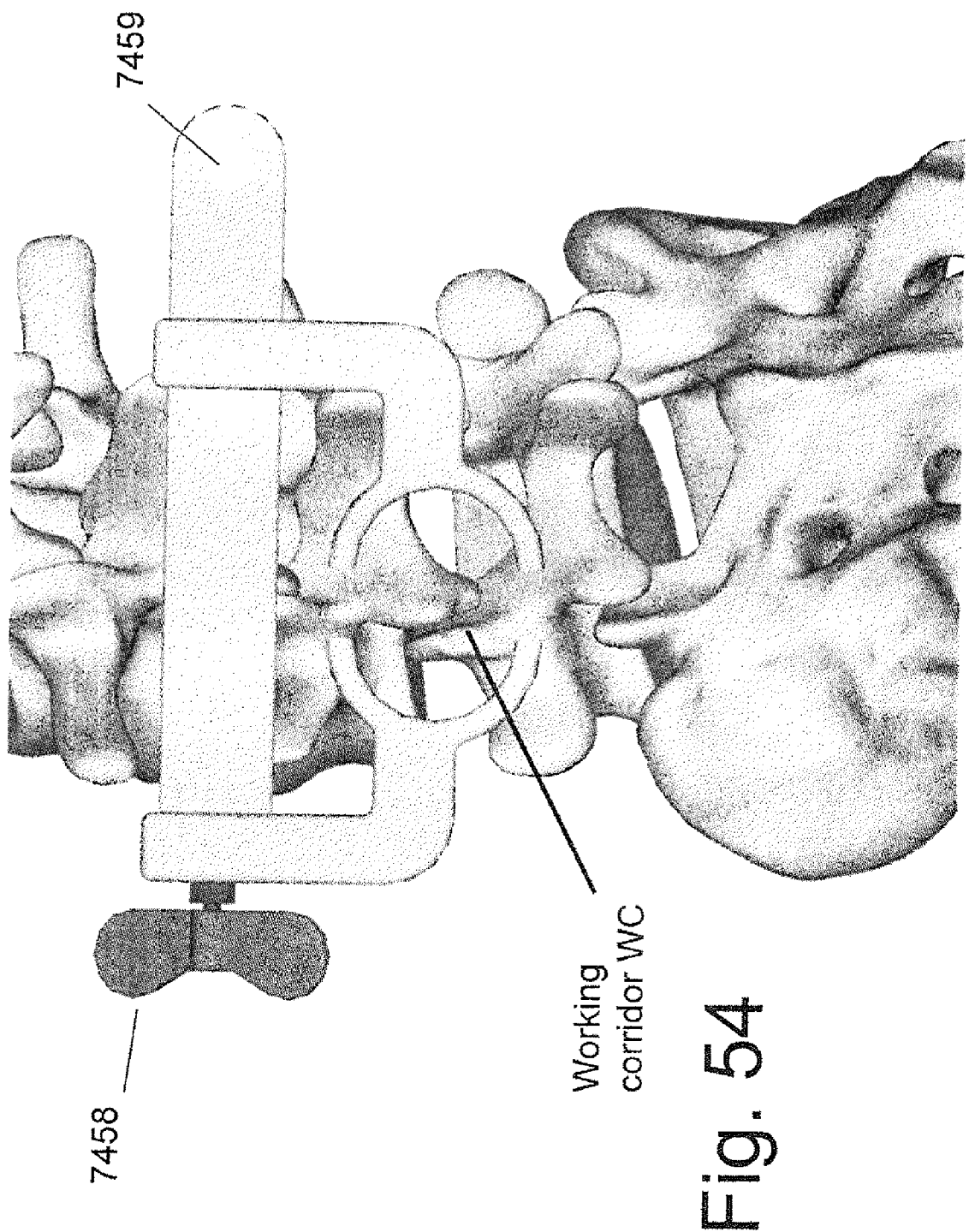
FIG. 54 illustrates a schematic view down the working corridor.

FIG. 54 illustrates a schematic view down the working corridor. Note that the facet joint necessarily rests at the bottom of the working corridor since placement of the retractor 810 was guided by member 730. That is, member 730 was anchored to the facet joint as an initial step in the operation and the anchor was then used to define the trajectory of the surgical corridor to the facet joint. The positioned retraction platform 810 may be further coupled to a frame device that anchors to the operating table (FIG. 25D).

After removal of member 730 and the cylindrical tubes, a surgical corridor is left between the tissue retractor blades through which the posterior aspect of the first facet may be accessed. The surgeon visually identifies and verifies that the posterior aspect of the first facet joint is at the distal end of the surgical corridor. Any soft tissue remaining over the posterior aspect of the facet joint is removed. The facet joint is then at least partially removed as described previously in detail. Preferably, at least a portion of the lateral surface of the SAP of inferior vertebral bone is removed with facet joint resection. The posterior aspect of the disc space that is immediately anterior to resected facet joint (and neural foramen) is exposed. The disc space is entered and at least partially evacuated and an orthopedic implant is positioned within the disc space as discussed in detail above.

In specific, the exposed disc entered through a transforaminal corridor, wherein the entry point of the posterior disc is at least partially in between the nerve root that exits the spinal canal beneath the pedicle of the superior vertebral bone and the pedicle of the inferior vertebral bone and lateral to the nerve that exits immediately beneath the pedicle of the inferior vertebral bone. An orthopedic implant is positioned into the disc space, wherein the implant can bear at least some of the load transmitted across the disc space and maintain the superior and inferior vertebral bones separated by a desired distance. Bone forming material is preferably positioned in the disc space if a fusion is desired. The retraction platform is removed.

If desired, prior to retraction platform removal, an additional bone fusion mass may be used to connect the transverse processes adjacent to removed facet joint—as discussed previously. In addition, a first bone screw assembly is anchored into the first pedicle of the superior vertebral bone and a second bone screw assembly is anchored into the ipsilateral pedicle of the inferior vertebral bone. The bone screw assemblies are then rigidly interconnected by a rod member.

Figure 55:
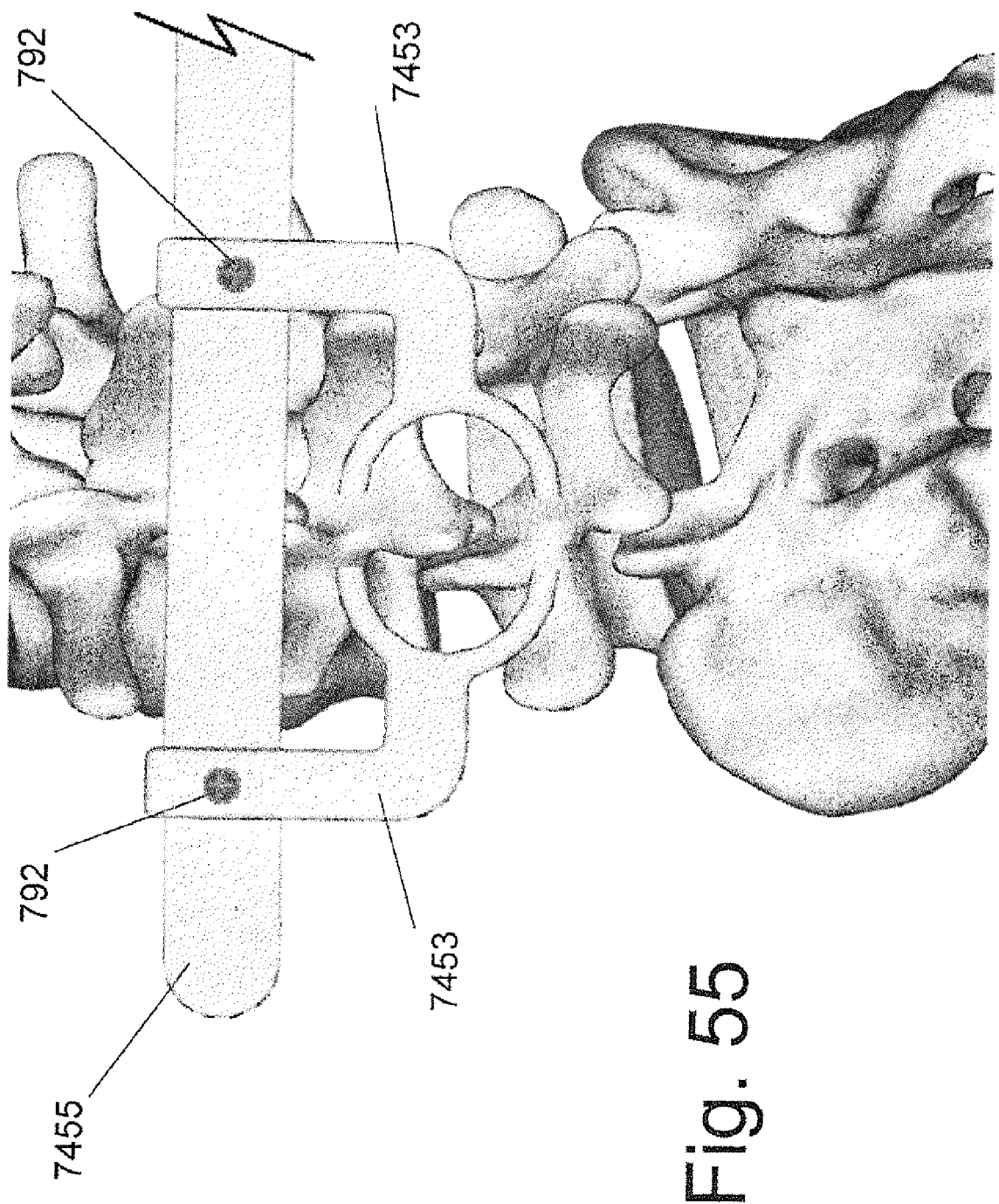
FIG. 55 illustrates an alternative embodiment of the retractor.

A modification of the previous embodiment is shown in FIG. 55. In this embodiment, both bar 7455 is a member of the frame device that is attached to the operating room table. Each blade member 7453 may be guided to the facet joint by anchored member 730 (as shown in the last embodiment) and then reversibly mounted onto bar 7455. (Further, the blades may be radiographically guided to the facet joint over guide wire 102 and cylindrical tubes without threaded advancement of member 730 into the facet joint. However, use of threaded member 730 provides less movement (and potential error) during retractor advancement). After moving the blade member into the desired position relative to bar 7455, a locking mechanism (set screw 792 here) is actuated to immobilize the blade member relative to bar 7455. As before, retractor platform 770 is also attached to the frame device. In this way, each of the two retractor blades that form and border the working corridor are independently attached to the frame device that anchors to the operating table.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A method for stabilization of a spinal segment having a first vertebral bone, a second vertebral bone, and an intervening intervertebral disc space, comprising:
   approaching a posterior aspect of said intervertebral disc space;
   creating an opening in a posterior aspect of an annulus fibrosis of said intervertebral disc space;
   advancing an anterior surface of an orthopedic implant through said opening in said annulus fibrosis; and
   advancing a remainder of said orthopedic implant into said intervertebral disc space, said orthopedic implant following a circular trajectory that is centered at an axis of rotation positioned outside of said orthopedic implant;
   wherein said orthopedic implant is configured to extend from said anterior surface to a posterior surface along an at least partially curvilinear axis, and comprises a first side surface and an opposing side surface, each configured to comprise a curvilinear segment that extends from said anterior to said posterior surfaces along a curvilinear trajectory and has a center of curvature positioned outside of said implant, said axis of rotation and said center of curvature of said implant being located on a same side of said implant.

2. The method of claim 1, wherein said orthopedic implant is substantially concave with respect to said axis of rotation.

3. The method of claim 1, further comprising identifying said posterior aspect of said intervertebral disc space with a radiographic imaging modality.

4. The method of claim 1, further comprising utilizing at least a distraction platform to displace a tissue retractor member thereby creating an operative corridor.

5. The method of claim 4, further comprising accessing a facet joint via said operative corridor and removing at least a portion thereof to expose said intervertebral disc space.

6. The method of claim 1, further comprising implanting a bone forming material within said disc space.

7. A method for spinal segment stabilization of a subject, comprising:
   creating an opening in a posterior aspect of an annulus fibrosis of an intervertebral disc space of said subject;
   advancing a first portion of an orthopedic implant through said opening, said orthopedic implant configured to extend along an at least partially curvilinear axis, and comprising a center of curvature positioned outside of said orthopedic implant; and
   advancing said orthopedic implant through a circular trajectory having a center that is outside of said orthopedic implant;
   wherein said advancement of said curvilinear orthopedic implant causes said implant to be positioned within said intervertebral disc space of said subject; and
   wherein said center of said circular trajectory and said center of curvature of said orthopedic implant are located on a same side of said implant.

8. The method of claim 7, further comprising:
   identifying a first pedicle of the first vertebral bone and an ipsilateral pedicle of the second vertebral bone with a radiographic imaging modality;
   using at least a tissue retractor member and a distraction platform to form an operative corridor;
   identifying a facet joint within said operative corridor; and
   removing at least a segment of said facet joint to expose said intervertebral disc space.

9. The method of claim 7, further comprising implanting a bone forming material within said intervertebral disc space.

10. The method of claim 7, further comprising substantially immobilizing said orthopedic implant within said disc space using at least one of:
   (i) a spinous process fastener;
   (ii) a fusion mass; and
   (iii) a fixation assembly.

11. The method of claim 7, wherein said orthopedic implant is substantially concave with respect to said center of said circular trajectory.

12. The method of claim 7, further comprising causing formation of a bony connection of a fusion mass on said ipsilateral side of said orthopedic implant and a fusion mass on an opposing contra-lateral side of said orthopedic implant via at least one cavity of said orthopedic implant.

13. The method of claim 7, wherein said act of advancing said first portion of said curvilinear orthopedic implant through said opening occurs via at least one implantation instrument.

14. A method for spinal segment stabilization of a subject, comprising:
   creating an opening in a posterior aspect of an annulus fibrosis of an intervertebral disc space of said subject;
   advancing a first portion of a curvilinear orthopedic implant through said opening, said curvilinear orthopedic implant comprising a center of curvature positioned outside of said orthopedic implant; and advancing a remainder of said curvilinear orthopedic implant into said intervertebral disc space via a circular trajectory having a center that is outside of said curvilinear orthopedic implant, said center of said circular trajectory and said center of curvature of said orthopedic implant being located on a same side of said implant.

15. The method of claim 14, further comprising displacing a tissue retractor member utilizing at least a distraction platform and thereby creating an operative corridor.

16. The method of claim 15, further comprising accessing a facet joint via said operative corridor and removing at least a portion thereof to expose said intervertebral disc space.

17. The method of claim 14, further comprising implanting a bone forming material within said intervertebral disc space.

18. The method of claim 14, further comprising substantially immobilizing said curvilinear orthopedic implant within said intervertebral disc space using at least one of:
   (i) a spinous process fastener;
   (ii) a fusion mass; and
   (iii) a fixation assembly.

\* \* \* \* \*